(12) United States Patent
Atherfold et al.

(10) Patent No.: US 11,220,547 B2
(45) Date of Patent: Jan. 11, 2022

(54) ANTIBODIES SPECIFIC TO FCRN

(71) Applicant: UCB BIOPHARMA SPRL, Brussels (BE)

(72) Inventors: Paul Alan Atherfold, Slough (GB); Thomas Allen Ceska, Slough (GB); Helene Margaret Finney, Slough (GB); Lara Kevorkian, Slough (GB); Kaushik Sarkar, Slough (GB); Bryan John Smith, Slough (GB); Kerry Louise Tyson, Slough (GB)

(73) Assignee: UCB Biopharma SPRL, Brussels (BE)

( * ) Notice: Subject to any disclaimer, the term of this patent is extended or adjusted under 35 U.S.C. 154(b) by 306 days.

(21) Appl. No.: 16/299,407

(22) Filed: Mar. 12, 2019

(65) Prior Publication Data

US 2019/0270811 A1    Sep. 5, 2019

Related U.S. Application Data

(62) Division of application No. 15/036,209, filed as application No. PCT/EP2014/074409 on Nov. 12, 2014, now Pat. No. 10,273,302.

(30) Foreign Application Priority Data

Nov. 12, 2013   (GB) ..................... 1320066

(51) Int. Cl.
| | | |
|---|---|---|
| *C07H 21/02* | (2006.01) | |
| *C07H 21/04* | (2006.01) | |
| *C12P 21/06* | (2006.01) | |
| *C12P 21/04* | (2006.01) | |
| *C12N 5/00* | (2006.01) | |
| *C12N 5/16* | (2006.01) | |
| *C12N 1/20* | (2006.01) | |
| *C07K 16/28* | (2006.01) | |
| *A61K 47/60* | (2017.01) | |
| *A61K 47/68* | (2017.01) | |
| *C07K 16/00* | (2006.01) | |
| *A61K 39/00* | (2006.01) | |

(52) U.S. Cl.
CPC ......... *C07K 16/283* (2013.01); *A61K 47/60* (2017.08); *A61K 47/6849* (2017.08); *A61K 2039/505* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/55* (2013.01); *C07K 2317/565* (2013.01); *C07K 2317/624* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez | |
| 5,219,996 A | 6/1993 | Bodmer | |
| 5,585,089 A | 12/1996 | Queen | |
| 5,667,425 A | 9/1997 | Pineau | |
| 7,662,928 B2 | 2/2010 | Balthasar | |
| 8,017,739 B2 | 9/2011 | Eichner | |
| 8,163,881 B2 | 4/2012 | Ober | |
| 8,834,871 B2 | 9/2014 | Ober | |
| 10,233,243 B2 | 3/2019 | Finney | |
| 10,273,302 B2 | 4/2019 | Atherfold | |
| 2002/0138863 A1 | 9/2002 | Roopenian | |
| 2007/0092507 A1 | 4/2007 | Balthasar | |
| 2010/0266530 A1 | 10/2010 | Roopenian | |
| 2014/0248287 A1 | 9/2014 | Tenhoor | |
| 2015/0118240 A1 | 4/2015 | Finney | |
| 2016/0264668 A1 | 9/2016 | Atherfold | |

FOREIGN PATENT DOCUMENTS

| | | |
|---|---|---|
| EP | 0392745 | 10/1990 |
| EP | 0948544 | 10/1999 |
| EP | 1090037 | 4/2001 |
| GB | 1320066 | 6/1973 |
| GB | 12083705 | 6/2013 |
| GB | 13200662 | 5/2015 |
| KR | 20130071961 A | 7/2013 |
| WO | 8601533 | 3/1986 |
| WO | 1986001533 | 3/1986 |
| WO | 8900195 | 1/1989 |
| WO | 1989000195 | 1/1989 |
| WO | 8901476 | 2/1989 |
| WO | 1989001476 | 2/1989 |
| WO | 9109967 | 7/1991 |
| WO | 1991009967 | 7/1991 |
| WO | 9202551 | 2/1992 |
| WO | 1992002551 | 2/1992 |
| WO | 9222583 | 12/1992 |
| WO | 1992022583 | 12/1992 |

(Continued)

OTHER PUBLICATIONS

Adair, J.R., et al., "Therapeutic antibodies," Drug Design Reviews—Online, 2005, vol. 2, No. 3, pp. 209-217.

(Continued)

*Primary Examiner* — Chun W Dahle

(74) *Attorney, Agent, or Firm* — Saul Ewing Arnstein & Lehr LLP; Doreen Y. Trujillo

(57) ABSTRACT

The disclosure relates to antibodies specific to FcRn, formulations comprising the same, use of each in therapy, processes for expressing and optionally formulating said antibody, DNA encoding the antibodies and hosts comprising said DNA.

52 Claims, 23 Drawing Sheets

Specification includes a Sequence Listing.

(56) References Cited

FOREIGN PATENT DOCUMENTS

| WO | 9306231 | 4/1993 |
|---|---|---|
| WO | 1993006231 | 4/1993 |
| WO | 9820734 | 5/1998 |
| WO | 9825971 | 6/1998 |
| WO | 1998025971 | 6/1998 |
| WO | 02060919 | 8/2002 |
| WO | 03031581 | 4/2003 |
| WO | 2003031581 | 4/2003 |
| WO | 03048208 | 6/2003 |
| WO | 2003048208 | 6/2003 |
| WO | 2004051268 | 6/2004 |
| WO | 2004106377 | 12/2004 |
| WO | 2005003169 | 1/2005 |
| WO | 2005003170 | 1/2005 |
| WO | 2005003171 | 1/2005 |
| WO | 2005013912 | 2/2005 |
| WO | 05113605 | 12/2005 |
| WO | 05117984 | 12/2005 |
| WO | 2005113605 | 12/2005 |
| WO | 2005117984 | 12/2005 |
| WO | 2006106323 | 10/2006 |
| WO | 2006118772 | 11/2006 |
| WO | 2007024715 | 3/2007 |
| WO | 2007087289 | 8/2007 |
| WO | 2007098420 A2 | 8/2007 |
| WO | 2008038024 | 4/2008 |
| WO | 2008043822 A2 | 4/2008 |
| WO | 2009020867 A2 | 2/2009 |
| WO | 2009040562 | 4/2009 |
| WO | 2009080764 | 7/2009 |
| WO | 2009131702 | 10/2009 |
| WO | 2010014909 A1 | 2/2010 |
| WO | 2010035012 | 4/2010 |
| WO | 2011030107 | 3/2011 |
| WO | 2011061492 | 5/2011 |
| WO | 2011086091 | 7/2011 |
| WO | 2012167039 A1 | 12/2012 |
| WO | 2013068571 | 5/2013 |
| WO | 2014019727 | 2/2014 |
| WO | 2014204280 | 12/2014 |
| WO | 2014204280 A1 | 12/2014 |
| WO | 2015071330 | 5/2015 |

OTHER PUBLICATIONS

Alina Sesarman et al., "The neonatal Fc receptor as therapeutic target in IgG-mediated autoimmune diseases," CMLS Cellular and Molecular Life Sciences, vol. 67, No. 15, Mar. 9, 2010, pp. 2533-2550.
Altschul, S.F. et al., "Basic local alignment search tool," J. Mol. Biol., vol. 215, No. 3, pp. 403-410, 1990.
Altschul, S.F. et al., "Gapped BLAST and PSI-BLAST: a new generation of protein database search programs," Nucleic Acids Res., vol. 25, No. 17, pp. 3389-3402, 1997.
Altshuler, E.P. et al., "Generation of Recombinant Antibodies and Means for Increasing Their Affinity," Biochemistry, Dec. 1, 2010, vol. 75, No. 13, pp. 1584-1605.
Angal, S., et al. "A single amino acid substitution abolishes the heterogeneity of chimeric mouse/human (IgG4) antibody", Molecular Immunology, vol. 30, No. 1, pp. 105-108, 1993.
Babcook, J. S. et al., "A novel strategy for generating monoclonal antibodies from single, isolated lymphocytes producing antibodies of defined specificities (PCR/antibody-forming cells/VH and VL genes/immunoglobulin/plaque assays)", Proceedings of the National Academy of Science, Jul. 1996, pp. 7843-7848, vol. 93, Immunology, USA.
Borvak, J. et al., "Functional expression of the MHC class I-related receptor, FcRn, in endothelial cells of mice," 1998, Int. Immunol., vol. 10, No. 9, pp. 1289-1298.
Burmesiter, et al., "Crystal structure of the complex of rat neonatal Dc receptor with Fc," Nature, vol. 372, Nov. 24, 1994 ,pp. 379-383.

Casset et al., "A peptide mimetic of an anti-CD4 monoclonal antibody by rational design," Biochemical and Biophysical Research Communication, vol. 307 (2003), pp. 198-205.
Cauza, K. et al., "Expression of FcRn, the MHC Class I-Related Receptor for IgG, in Human Keratinocytes," Jan. 2005, J. Invest. Dermatol., vol. 124, No. 1, pp. 132-139.
Chapman, A., 'PEGylated antibodies and antibody fragments for improved therapy: a review', Advanced Drug Delivery Reviews, vol. 54, No. 4, pp. 531-545, 2002.
Chothia, C. and Lesk, A.M., "Canonical Structures for the Hypervariable Regions of Immunoglobulins," J. Mol. Biol., vol. 196, pp. 901-917, 1987.
Chowdhury, P.S. et al., "Improving Antibody Infinite by Mimicking Somatic Hypermutation in Vitro," Nature Biotechnology, vol. 17, Nature Publishing Group, New York, NY, Jun. 1, 1999, pp. 568-572.
Christianson, Gregory J. et al., "Monoclonal antibodies directed against human FcRn and their applications," mAbs, vol. 4, No. 2, Mar. 2012, pp. 208-216.
Claypool et al., "Bidirectional Transepithelial IgG Transport by a Strongly Polarized Basolateral Membrane Fcy-Receptor," Apr. 2004, Mol. Biol. Cell, vol. 15, No. 4, pp. 1746-1759.
Claypool et al., "Functional Reconstitution of Human FcRn in Madin-Darby Canine Kidney Cells Requires Co-expressed Human Beta2-Microglobulin," 2002, Journal of Biological Chemistry, vol. 277, No. 31, pp. 28038-28050.
Co-pending U.S. Appl. No. 15/036,209, filed May 12, 2016, Now Issued U.S. Pat. No. 10,273,302.
Cole, S.P.C., et al., "The EBV-hybridoma technique and its application to human lung cancer," Monoclonal Antibodies and Cancer Therapy, vol. 27, (UCLA Symposia on Molecular and Cellular Biology, New Series, R.A. Reisfeld and S. Sell (eds.)), pp. 77-96, Alan R. Liss, Inc., N.Y, 1985.
Crameri, A., et al., "DNA shuffling of a family of genes from diverse species accelerates directed evolution," Nature, Jan. 15, 1998, vol. 391, pp. 288-291.
Dubowchik, G.M., et al., "Receptor-mediated and enzyme-dependent targeting of cytotoxic anticancer drugs," Pharmacology and Therapeutics, vol. 83, No. 2, pp. 67-123, 1999.
Feng Y. et al., "Design, expression and characterization of a soluble single-chain functional human neonatal Fc receptor," Protein expression and purification, Sep. 2011, vol. 79, No. 1, pp. 66-71.
Firan et al., "The MHC class I-related receptor, FcRn, plays an essential role in the maternofetal transfer of y-globulin in humans," 2001, International Immunology, vol. 13, No. 8, pp. 993-1002.
Getman, Kate, E. et al., "Pharmacokinetic effects of 4C9, an anti-FcRn antibody, in rates: implications for the use of FcRn inhibitors for the treatment of humoral autoimmune conditions," Journal of Pharmaceutical Sciences, vol. 94, No. 4, Apr. 1, 2005, pp. 718-729.
Gish, W., and States, D.M., "Identification of protein coding regions by data base similarity search," Nature Genet., vol. 3, No. 3, pp. 266-272, 1993.
Harris, J.M., and Zalipsky, S., eds., "Poly(ethyleneglycol) Chemistry and Biological Applications", American Chemical Society, Washington DC, 1997.
Harris, R.J., "Processing of C-terminal lysine and arginine residues of proteins isolated from mammalian cell culture," Journal of Chromatography, vol. 705, No. 1, pp. 129-134, 1995.
Hellstrom, K.E. et al., 'Antibodies for drug delivery,' Controlled Drub Delivery, Robinson, et al., eds, Marcel Dekker, Inc., Ed. 2, Chapter 15, pp. 623-653 (1987).
Hieter, P.A., et al., 'Evolution of human immunoglobulin kappa J region genes', J. Biol. Chem., vol. 257, No. 3, pp. 1516-1522, 1982.
Holliger and Hudson, "Engineered antibody fragments and the rise of single domains," Nature Biotechnology, vol. 23, No. 9, pp. 1126-1136, Sep. 2005.
International Search Report dated Feb. 17, 2015 for International Application No. PCT/EP2014/074409.
International Search Report, International Application PCT/EP2013/059802, dated Jan. 2, 2014.
Janeway et al., Immunology Third Edition, Garland Publishing Inc. 1997, Chapters, Structure of the Antibody Molecule and Immunoglobulin Genes, pp. 3:1-3:11.

(56) References Cited

OTHER PUBLICATIONS

Kabat, et al., 'Sequences of Proteins of Immunological Interest', 4th ed., US Department of Health and Human Services, Public Health Service, National Institutes of Health, 1983, pp. xv-xviii.
Kashmiri, S.V.S., et al., 'SDR grafting—a new approach to antibody humanization', Methods, vol. 36, pp. 25-34, 2005.
Kohler & Milstein, "Continuous cultures of fused cells secreting antibody of predefined specificity," Nature, Aug. 7, 1975, pp. 495-497, vol. 256, nature Publishing Group.
Kozbor, D., et al., "The production of monoclonal antibodies from human lymphocytes," Immunology Today, vol. 4, No. 3, pp. 72-79, 1983.
Liu L. et al., "Amelioration of experimental autoimmune myasthenia gravis in rats by neonatal FcR blockade," J Immunol, Apr. 15, 2007, vol. 178, No. 8, pp. 5390-5398.
Low, N. M., et al., 'Mimicking Somatic Hypermutation Affinity Maturation of Antibodies Displayed on Bacteriophage Using a Bacterial Mutator Strain', J. Mol. Biol., vol. 260, No. 3, pp. 359-368, 1996.
Madden, T.L., et al., 'Applications of Network Blast Server', Meth. Enzymol., vol. 266, pp. 131-141, 1996.
Marks, J.D., et al., "By-passing Immunization Human: Building High Affinity Human Antibodies by Chain Shuffling," Bio/Technology, vol. 10, pp. 779-783, 1992.
Ober et al., "Differences in promiscuity for antibody-FcRn interactions across species: implications for therapeutic antibodies," 2001, Int. Immunol. vol. 13, No. 12, pp. 1551-1559.
Ober, RJ, et al., "Visualizing the Site and Dynamics of IgG Salvage by the MHC Class I-Related Receptor, FcRn," 2004, The Journal of Immunology, 172, pp. 2021-2029.
Patten, P., et al., "Applications of DNA shuffling to pharmaceuticals and vaccines," Curr. Opin. Biotechnol., vol. 8, No. 6, pp. 724-733, 1997.
Paul et al, Fundamental Immunology, 3rd ed. 1993, p. 242.
Portolano et al., "Lack of Promiscuity in Autoantigen-Specific H and L Chain Combinations as Revealed by Human H and L Chain Roulette," Journal of Immunology, 1993, vol. 150, pp. 880-887.
Raghavan, M. et al., "Analysis of pH Dependence of the Neonatal Fc Receptor/ Immunoglobulin G Interaction Using Antibody and Receptor Variants," Biochemistry, vol. 34, No. 45, 1995, pp. 14649-14657.
Ravetch, J.V., et al., 'Structure of the human immunoglobulin mu locus: characterization of embryonic and rearranged J and D genes', Cell, vol. 27, No. 3, Pt 2, pp. 583-591, 1981.
Riechmann, et al., 'Reshaping human antibodies for therapy', Nature, vol. 332, pp. 323-327, 1988.
Roopenian and Akilesh, "FcRn: the neonatal Fc receptor comes of age," Nature Reviews Immunology, Sep. 2007, vol. 7, pp. 715-725.
Rudikoff et al., "Single amino acid substitution altering antigen-binding specificity," PNAS, 1982, vol. 79, pp. 1979-1983.
Scatchard et al., "The attractions of proteins for small molecules and ions," Annals New York Academy of Science, vol. 51, pp. 660-672 (1949).
Thompson, J., et al., "Affinity maturation of a high-affinity human monoclonal antibody against the third hypervariable loop of human immunodeficiency virus: use of phage display to improve affinity and broaden strain reactivity," J. Mol. Biol., vol. 256, No. 1, pp. 77-88, 1996.
Thorpe, P.E., et al., 'The preparation and cytotoxic properties of antibody-toxin conjugates', Immunol. Rev, vol. 62, pp. 119-158, 1982.
Vaccaro C. et al., "Engineering the Fc region of immunoglobulin G to modulate in vivo antibody levels," Nature Biotechnology, Oct. 2005, vol. 23, No. 10, pp. 1283-1288.
Vaughan, et al., 'Human antibodies by design,' Nature Biotechnology, vol. 16, No. 6, pp. 535-539, 1998.
Verma, R., et al., "Antibody engineering: comparison of bacterial, yeast, insect and mammalian expression systems," Journal of Immunological Methods, vol. 216, Nos. 1-2, pp. 165-181, 1998.
Wark, K. L. et al., "Latest Technologies for the enhancement of antibody affinity," Advanced Drug Delivery Reviews, Aug. 7, 2006, vol. 58, No. 5-6, Elsevier BV, Amsterdam, NL, pp. 657-670.
Wolff et al., "Monoclonal Antibody Homodimers: Enhanced Anti-tumor Activity in Nude Mice," Cancer Research, vol. 53, pp. 2560-2565 (1993).
Written Opinion of the International Searching Authority for International Application No. PCT/EP2013/059802 dated Jan. 2, 2014.
Written Opinion of the International Searching Authority dated Feb. 17, 2015 for International Application No. PCT/EP2014/074409.
Yang, W.P. et al., "CDR Walking Mutagenesis for the Affinity Maturation of a Potent Human Anti-HIV-1 Antibody into the Picomolar Range," J. Mol. Biol., vol. 254, No. 3, pp. 392-403, 1995.
Zhang, J. & Madden, T.L., "PowerBLAST: a new network Blast application for interactive or automated sequence analysis and annotation", Genome Res., vol. 7, No. 6, pp. 649-656, 1997.
Zubler, R. H. et al., "Mutant EL-4 thymoma cells polyclonally activate murine and human B cells via direct cell interaction," J. Immunol., vol. 134, pp. 3662-3668 (1985).
International Search Report of International Application No. PCT/EP2016/060305 dated Jun. 14, 2016.
Aalberse et al., "IgG4 breaking the rules," (2002), Immunology 105, pp. 9-19.
Akilesh S et al., "The MHC class I-like Fc receptor promotes humorally mediated autoimmune disease," (2004), J Clin Invest; vol. 113, No. 9, pp. 1328-1333.
Akilesh S et al., "Neonatal FcR Expression in Bone Marrow-Derived Cells Functions to Protect Serum IgG from Catabolism," (2007), J Immunol; vol. 179, pp. 4580-4588.
Andersen JT et al., "Cross-species Binding Analyses of Mouse and Human Neonatal Fc Receptor Show Dramatic Differences in Immunoglobulin G and Albumin Binding," (2010), J Biol Chem; vol. 285, No. 7, pp. 4826-4836.
Anderson CL et al., "Perspective—FcRn transports albumin: relevance to immunology and medicine," (2006), Trends Immunol; vol. 27, No. 7, pp. 343-348.
Berger, Melvin, "Subcutaneous IgG in neurologic diseases," (2014), Immunotherapy vol. 6, No. 1, pp. 71-83.
Besada, Emilio, "Low immunoglobulin levels increase the risk of severe hypogammaglobulinemia in granulomatosis with polyangiitis patients receiving rituximab," (2016), BMC Musculoskelet Disord; vol. 17:6, pp. 1-7.
Cain K et al., "A CHO Cell Line Engineered to Express XBP1 and ERO1-Lx Has Increased Levels of Transient Protein Expression," (2013), Biotechnol Prog; vol. 29, No. 3, pp. 697-706.
Dall'Acqua, WF et al., "Increasing the Affinity of a Human IgG1 for the Neonatal Fc Receptor: Biological Consequences," (2002), J Immunol; vol. 169, pp. 5171-5180.
Dall'Acqua, WF et al., "Properties of Human IgG1s Engineered for Enhanced Binding to the Neonatal Fc Receptor (FcRn)," (2006), J Biol Chem; vol. 281, No. 33, pp. 23514-2324.
Datta-Mannan, A et al., "Monoclonal Antibody Clearance Impact of Modulating the Interaction of IgG with the Neonatal Fc Receptor," (2007), J Biol Chem; vol. 282, No. 3, pp. 1709-1717.
Fagerberg, L et al., "Analysis of the Human Tissue-specific Expression by Genome-wide Integration of Transcriptomics and Antibody-based Proteomics," (2014), Mol Cell Proteomics; 13, pp. 397-406.
Gonzalez-Noriega, A et al., "Chloroquine inhibits lysosomal enzyme pinocytosis and enhances lysosomal enzyme secretion by impairing receptor recycling," (1980), J Cell Biol; vol. 85, pp. 839-852.
Humphreys, F et al., "The characteristics of urticaria in 390 patients," (1998), Br J Dermatol; vol. 138, pp. 635-638.
Junghans, RP et al., "The ptoection receiption for IgG catabolism is the Beta 2-microglobulin-containing neonatal intestinal transport receptor," (1996), Proc Natl Acad Sci U S A; vol. 93, pp. 5512-5516.
Kiessling, P et al., "The FcRn inhibitor rozanolixizumab reduces human serum IgG concentration: A randomized phase 1 study," (2017), Sci Transl Med; col. 9, pp. 1-12.
Kim, J et al., "Kinetics of FcRn-mediated recycling of IgG and albumin in human: pathophysiology and therapeutic implications using a simplified mechanism-based model," (2007), Clin. Immunol. vol. 122, pp. 146-155.

(56) References Cited

OTHER PUBLICATIONS

Krishna, M et al., "Immunogenicity to Biotherapeutics—The Role of Anti-drug Immune Complexes," (2016) Front Immunol; vol. 7, Article 21, pp. 1-13.
Li, N et al., "Complete FcRn dependence for intravenous Ig therapy in autoimmune skin blistering diseases," (2005), J Clin Invest; vol. 115, No. 12, pp. 3440-3450.
Lightwood, D et al., "The Discovery, Engineering and Characterisation of a Highly Potent Anti-Human IL-13 Fab Fragment Designed for Administration by Inalation," (2013), J Mol Biol; vol. 425, pp. 577-593.
Liu, Z et al., "Beta 2-microglobulin-deficient Mice Are Resistant to Bullous Pemphigoid," (1997), J Exp Med; vol. 186, No. 5, pp. 777-783.
Martins, JP et al., "A comprehensive review of the neonatal Fc receptor and its application in drug delivery," (2016), Pharmacol Ther; vol. 161, pp. 22-39.
Matucci, A et al., "Mechanisms of action of Ig preparations: immunolodulatory and anti-inflammatory effects," (2014), Front Immunol; vol. 5, Article 690, pp. 1-5.
Mezo, AR et al., "Reduction of IgG in nonhuman primates by a peptide antagonist of the neonatal Fc receptor FcRn," (2008), Proc Natl Acad Sci U S A; vol. 105, No. 7, pp. 2337-2342.
Neuber, T et al., "Characterization and screening of IgG binding to the neonatal Fc receptor," (2014), MAbs, vol. 6, Issue 4, pp. 928-942.
Nixon, AE et al., "Fully human monoclonal antibody inhibitors of the neonatal Fc receptor reduce circulating IgG in non-human primates," (2015), Front Immunol; vol. 6, Article 176, pp. 1-13.
Oganesyan, V et al., "Structural Insights into Neonatal Fc Receptor-based Recycling Mechanisms," (2014), Journal of Biological Chemistry; vol. 289, No. 11, pp. 7812-7824.
Ohkubo, A et al., "Removal Characteristics of Immunoglobulin G Subclasses by Conventional Plasma Exchange and Selective Plasma Exchange," (2015), Ther Apher Dial; vol. 19, No. 4, pp. 361-366.
Patel, DA et al., "FcRn blockade by Fc engineering ameliorates arthritis in a murine model," (2011), J Immunol; vol. 187, No. 2, pp. 1015-1022.
Petkova, SB et al., "Enhanced half-life of genetically engineered human IgG1 antibodies in a humanized FcRn mouse model: potential application in humorally mediated autoimmune disease," (2006), Int Immunol; vol. 18, No. 12, pp. 1759-1769.
Pyzik, M et al., "FcRn: The architect behind the immune and non-immune functions of IgG and albumin," (2015), J Immunol; vol. 194, No. 10, pp. 4595-4603.
Raghavan, M et al., "Investigation of the Interaction between the Class I MHC-Related Fc Receptor and its Immunoglobulin G Ligand," (1994), Immunity; vol. 1, pp. 303-315.
Roopenian, DC et al., "The MHC Class I_Like IgG Receptor Controls Perinatal IgG Transport, IgG Homeostasis, and Fate of IgG-Fc-Coupled Drugs," (2003), J Immunol; vol. 170, pp. 3528-3533.
Sand, KMK et al., "Unraveling the interaction between FcRn and albumin: opportunities for design of albumin-based therapeutics," (2014), Front. Immunol; vol. 5, Article 682, pp. 1-21.
Schmidt, MM et al., "Crystal Structure of an HSA/FcRn Complex Reveals Recycling by Competitive Mimicry of HSA Ligands at a pH-Dependent Hydrophobic Interface," (2013); vol. 21, pp. 1966-1978.
Schwartz, J et al., "Guidelines on the Use of Therapeutic Apheresis in Clinical Practice—Evidence-Based Approach from the Writing Committee of the American Society for Apheresis: The Sixth Special Issue," (2013), J Clin Apher 2013; vol. 28, pp. 145-284.
Sewell, WA et al., "European consensus proposal for immunoglobulin therapies," (2014), Eur. J. Immunol; vol. 44, pp. 2207-2214.
Uno, Y et al., "Polymorphisms of Neonatal Fc Receptor in Cynomolgus and Rhesus Macaques," (2014), Drug Metab Pharmacokinet; vol. 29, No. 5, pp. 427-430.
Waldmann, TA et al., "Familial Hypercatabolic Hypoproteinemia," (1990), J Clin Invest; vol. 86, pp. 2093-2098.
Wang, J et al., "Intravenous immunoglobulin in critically ill adults: When and what is the evidence?" (2015), J Crit Care; vol. 30, pp. 652.e9-652e.16.
Wani, MA et al., "Familial hypercatabolic hypoproteinemia caused by deficiency of the neonatal Fc receptor, FcRn, due to a mutant beta2-microglobulin gene," (2006), Proc Natl Acad Sci U S A; vol. 103, No. 13, pp. 5084-2089.
Ward, ES et al., "Targeting FcRn fortherapy: from live cell imaging to in vivo studies in mice," (2014), Immunol Lett; vol. 160, No. 2, pp. 158-162.
Warncke, M et al., "Different Adaptations of IgG Effector Function in Human and Nonhuman Primates and Implications for Therapeutic Antibody Treatment," (2012), J Immunol; vol. 188, pp. 4405-4411.
West, AP et al., "Crystal Structure and Immoglobulin G Binding Properties of the Human Major Histocompatibility Complex-Related Fc Receptor," (2000), Biochemistry; vol. 39, pp. 9698-96708.
Zhou, J et al., "Conferring the Binding Properties of the Mouse MHC Class I-related Receptor, FcRn, onto the Human Ortholog by Sequential Rounds of Site-directed Mutagenesis," (2005), J Mol Biol; vol. 345, pp. 1071-1081.
Zhou, J et al., "High Affinity Nucleocapsid Protein Binding to the Mu Psi RNA Packaging Signal of Rous Sarcoma Virus," (2005), J Mol Biol; vol. 349, pp. 976-988.
Co-pending U.S. Appl. No. 14/400,812, filed Nov. 13, 2014, Now issued U.S. Pat. No. 10,233,243.
Co-pending U.S. Appl. No. 15/573,185, filed Nov. 10, 2017.
Written Opinion of the International Searching Authority for International Application No. PCT/EP2016/060305 dated Jun. 14, 2016.
Lu, D. et al., "Fab-scFv fusion protein: an efficient approach to production of bispecific antibody fragments," Journal of Immunological Methods, vol. 267, No. 2, Sep. 15, 2002, pp. 213-226.
Luo, D. et al., "Vl-Linker-Vh Orientation-Dependent Expression of Single Chain Fv Containing an Engineered Disulfide-Stabilized Bond in the Framework Region," J. Biochem., vol. 118, No. 4, pp. 825-831 (1995).
Young et al, "Thermal stabilization of a single-chain Fv antibody fragment by introduction of a disulphide bond," FEBS Letters vol. 377, Issue 2, pp. 135-139 (1995).
Glockshuber et al, "A comparison of strategies to stabilize immunoglobulin Fv-fragments," Biochemistry vol. 29, No. 6, pp. 1362-1367 (1990).
Zhu et al, "Remodeling domain interfaces to enhance heterodimer formation," Protein Science vol. 6, pp. 781-788 (1997).
Brinkmann et al., "A recombinant immunotoxin containing a disulfide-stabilized Fv fragment," Proc. Natl. Acad. Sci. USA, vol. 90, Issue 16, pp. 7538-7542 , (1993).
Rajagopal et al., "A form of anti-Tac(Fv) which is both single-chain and disulfide stabilized: comparison with its single-chain and disulfide-stabilized homologs," Protein Engineering, vol. 10 No. 12 pp. 1453-1459 (1997).
Reiter, et al., "Improved Binding and Antitumor Activity of a Recombinant Anti-erbB2 Immunotoxin by Disulfide Stabilization of the Fv Fragment," Journal of Biological Chemistry vol. 269 No. 28 pp. 18327-18331 (1994).
William E. Paul, M.D. ed., Fundamental Immunology 3rd ed. 1993, p. 242 (Year: 1993).
Casset et al. (BBRC(2003) 307, 198-205. (Year: 2003).
Rudikoff et al., "Single amino acid substitution altering antigen-binding specificity", PNAS 1982. vol. 79 p. 1979-1983 (Year: 1982).
Janeway et al., Immunology Third Edition, Garland Publishing Inc. 1997, Chapters, Structure of the Antibody Molecule and Immunoglobulin Genes, pp. 3:1-3:11 (Year: 1997).
Co-pending U.S. Appl. No. 16/271,086, filed Feb. 8, 2019.
Zanella, A., et al., "Treatment of autoimmune hemolytic anemias", Haematologica 2014, 99(10):1547-1554.
Co-Pending U.S. Appl. No. 16/622,358, filed Dec. 13, 2019.
Co-Pending U.S. Appl. No. 16/300,522, filed Nov. 9, 2018.
Office Action, Japanese Patent Application No. JP2020-093532, dated Jul. 20, 2021.

(56) References Cited

OTHER PUBLICATIONS

English translation of Office Action, Japanese Patent Application No. JP2020-093532, Jul. 20, 2021.

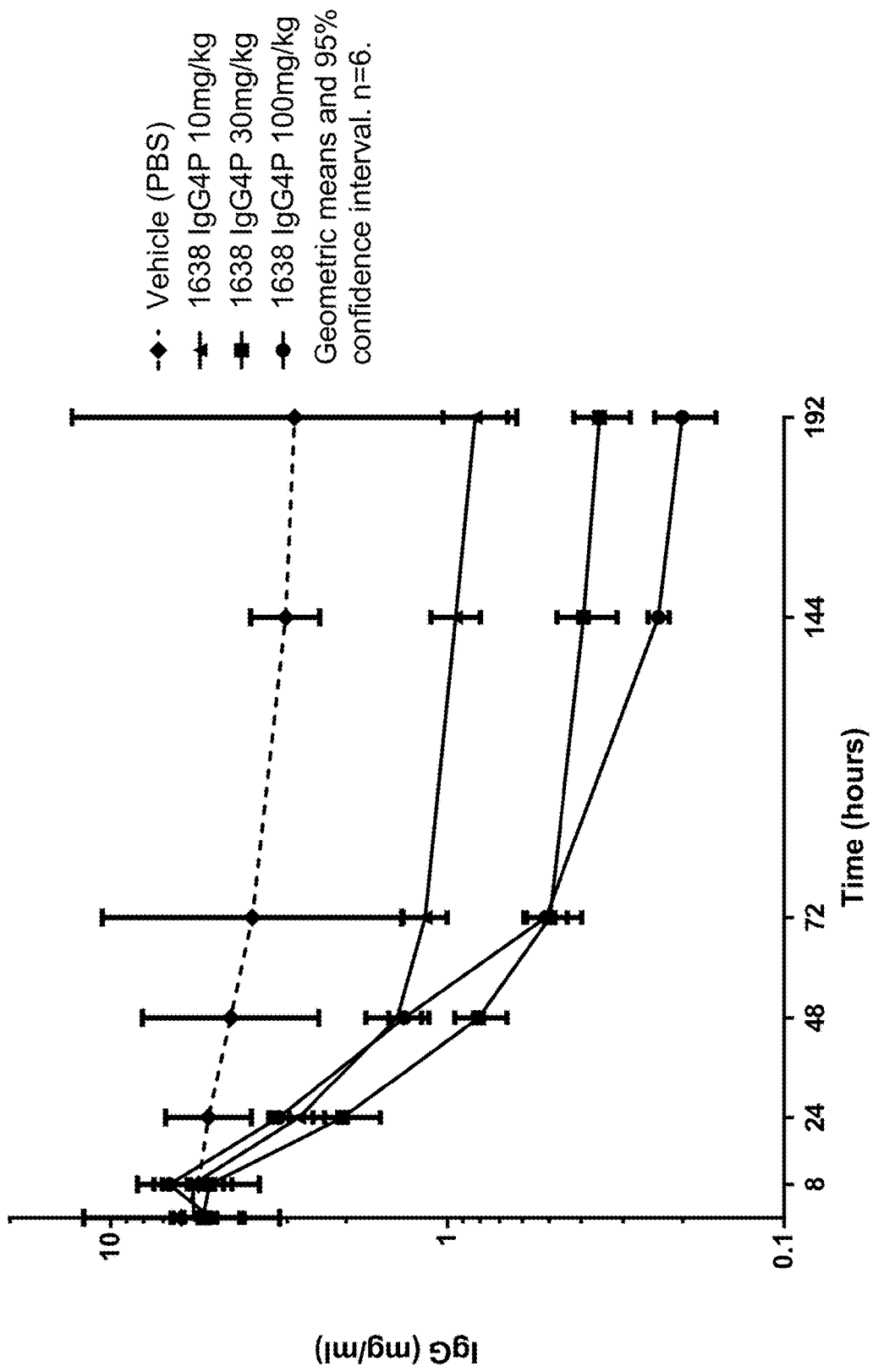
FIG. 1A The effect of 1638 IgG4P format on the concentration of human IVIg in serum of human FcRn-transgenic mice.
FIG. 1B The effect of 1638 FabFv and Fab'PEG formats on the concentration of human IVIg in human FcRn-transgenic mice.

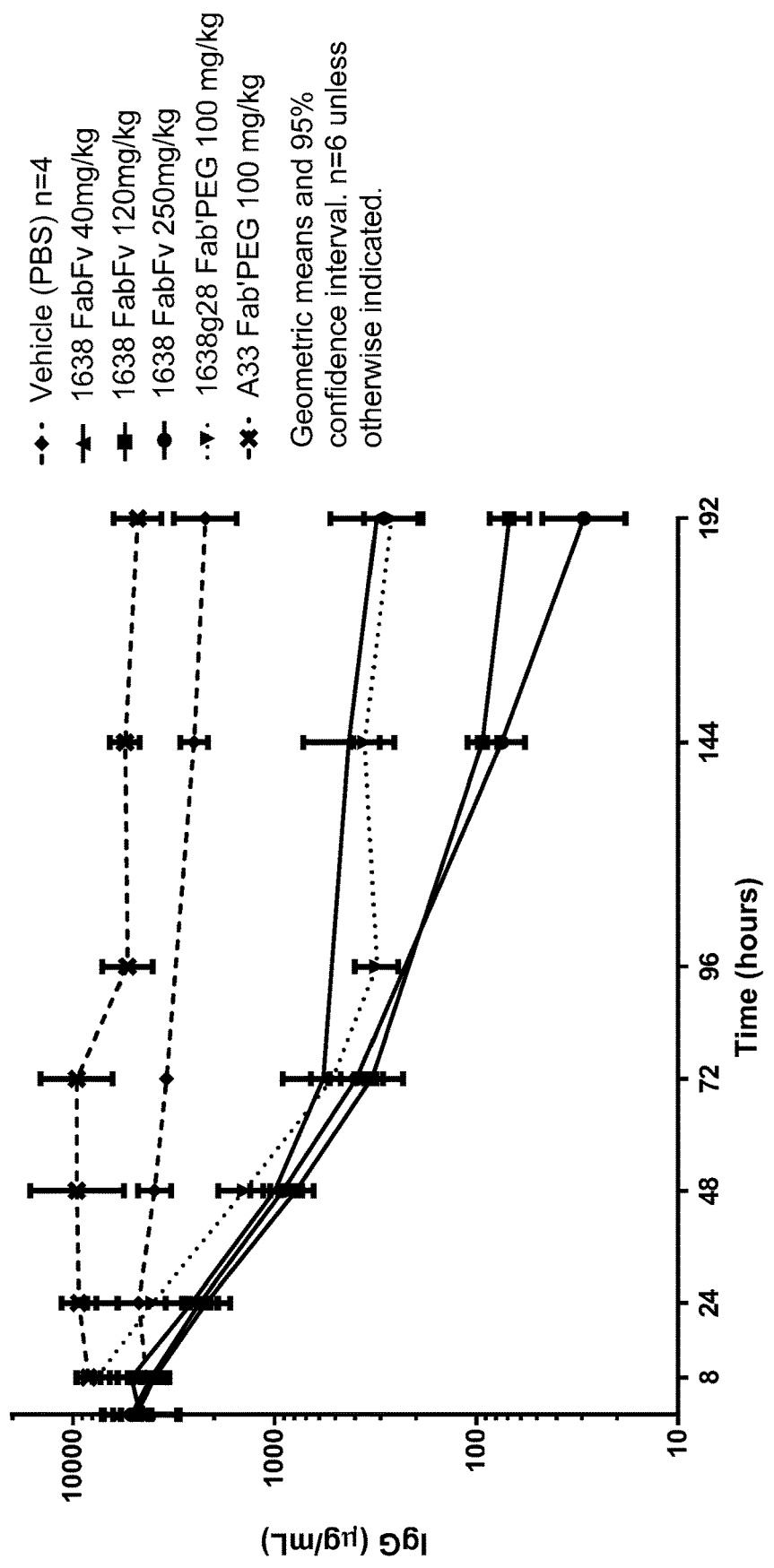
FIG. 1B    The effect of 1638 FabFv and Fab'PEG formats on the concentration of human IVIg in human FcRn-transgenic mice.

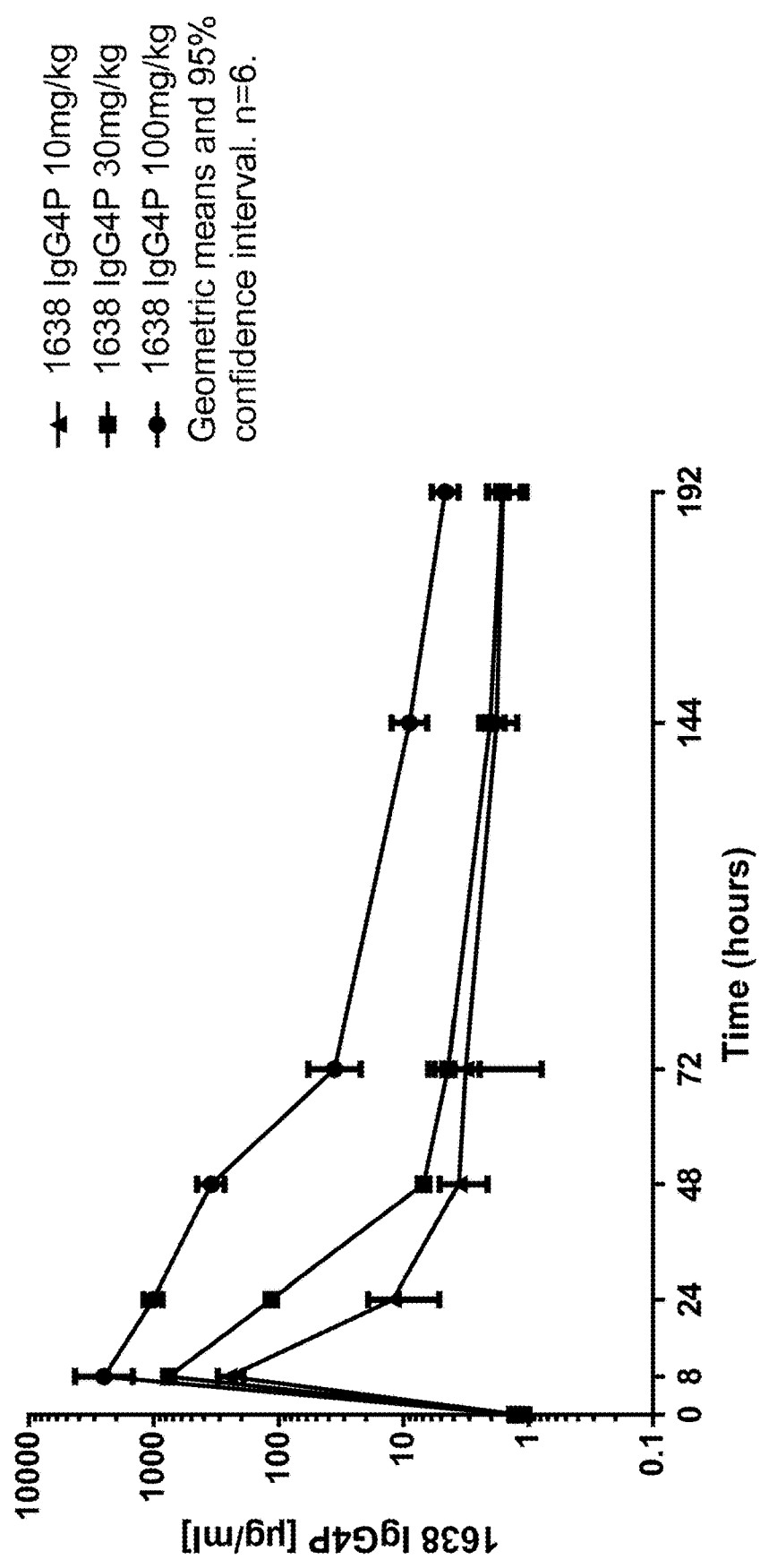
FIG. 1C  The pharmacokinetics of 1638 IgG4P format in human FcRn-transgenic mice.

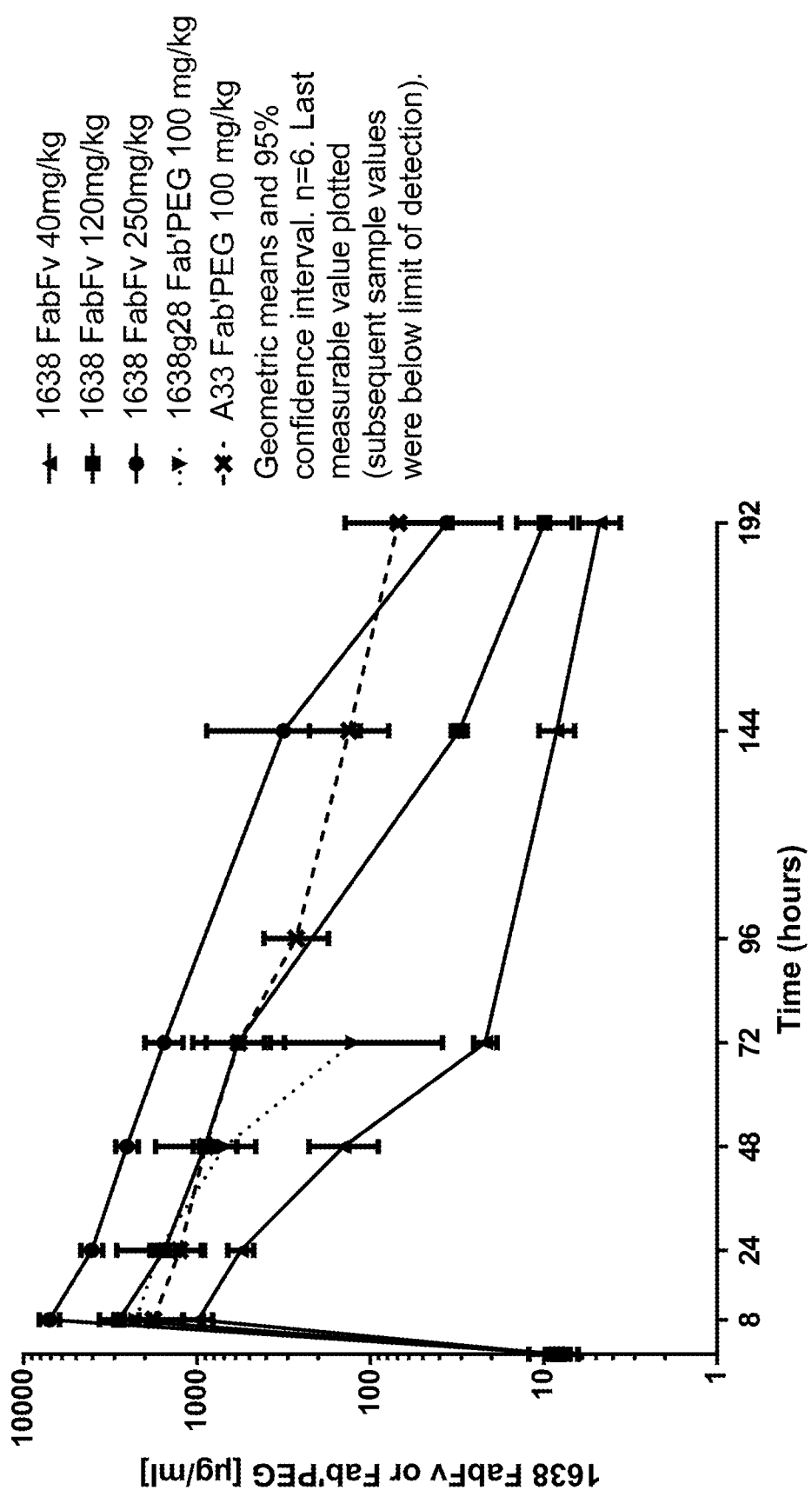
FIG. 1D  The pharmacokinetics of 1638 FabFv and Fab'PEG formats in human FcRn-transgenic mice.

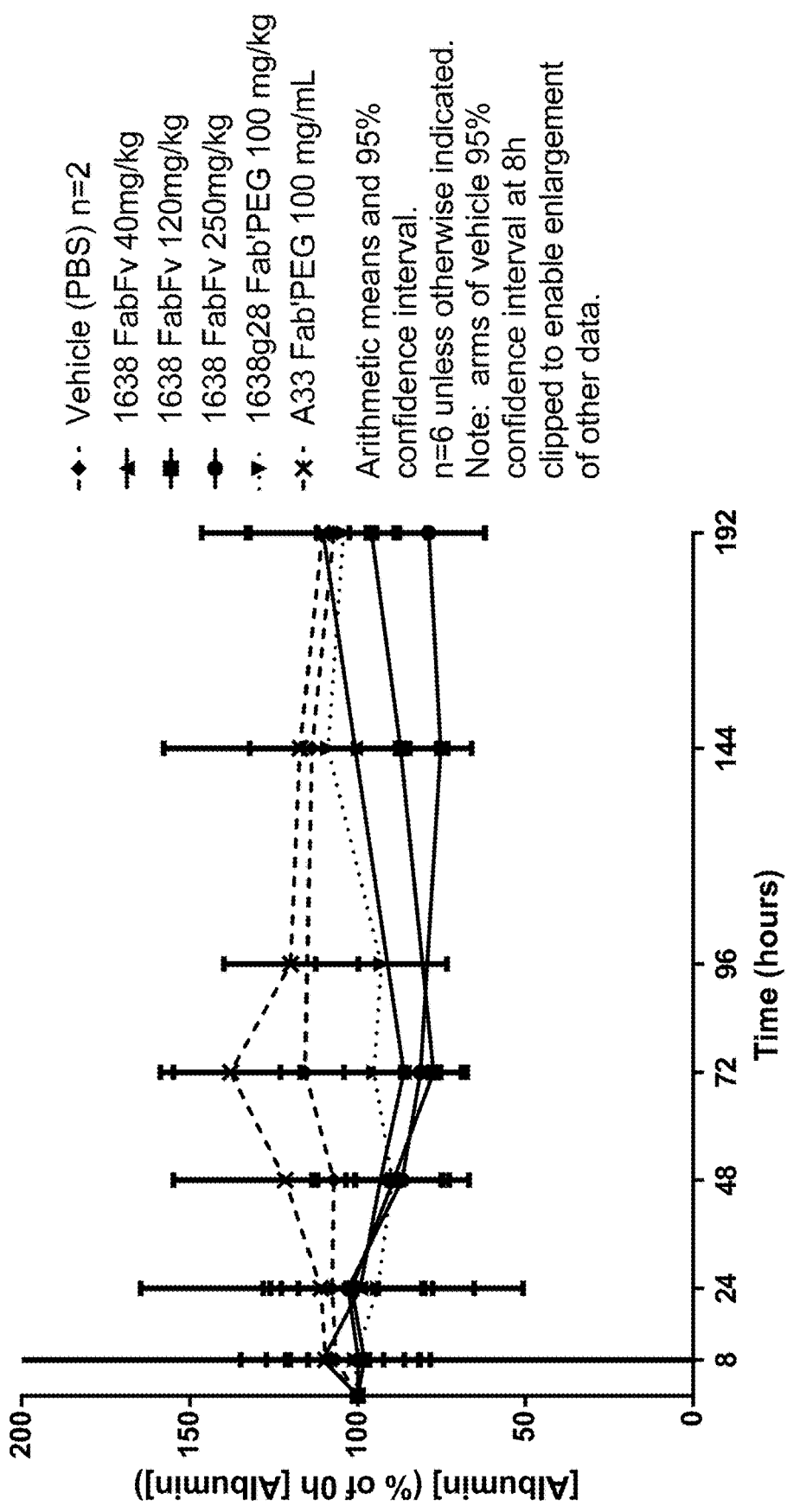
FIG. 1E  The effect of 1638 FabFv and Fab'PEG formats on the concentration of serum albumin in human FcRn-transgenic mice.

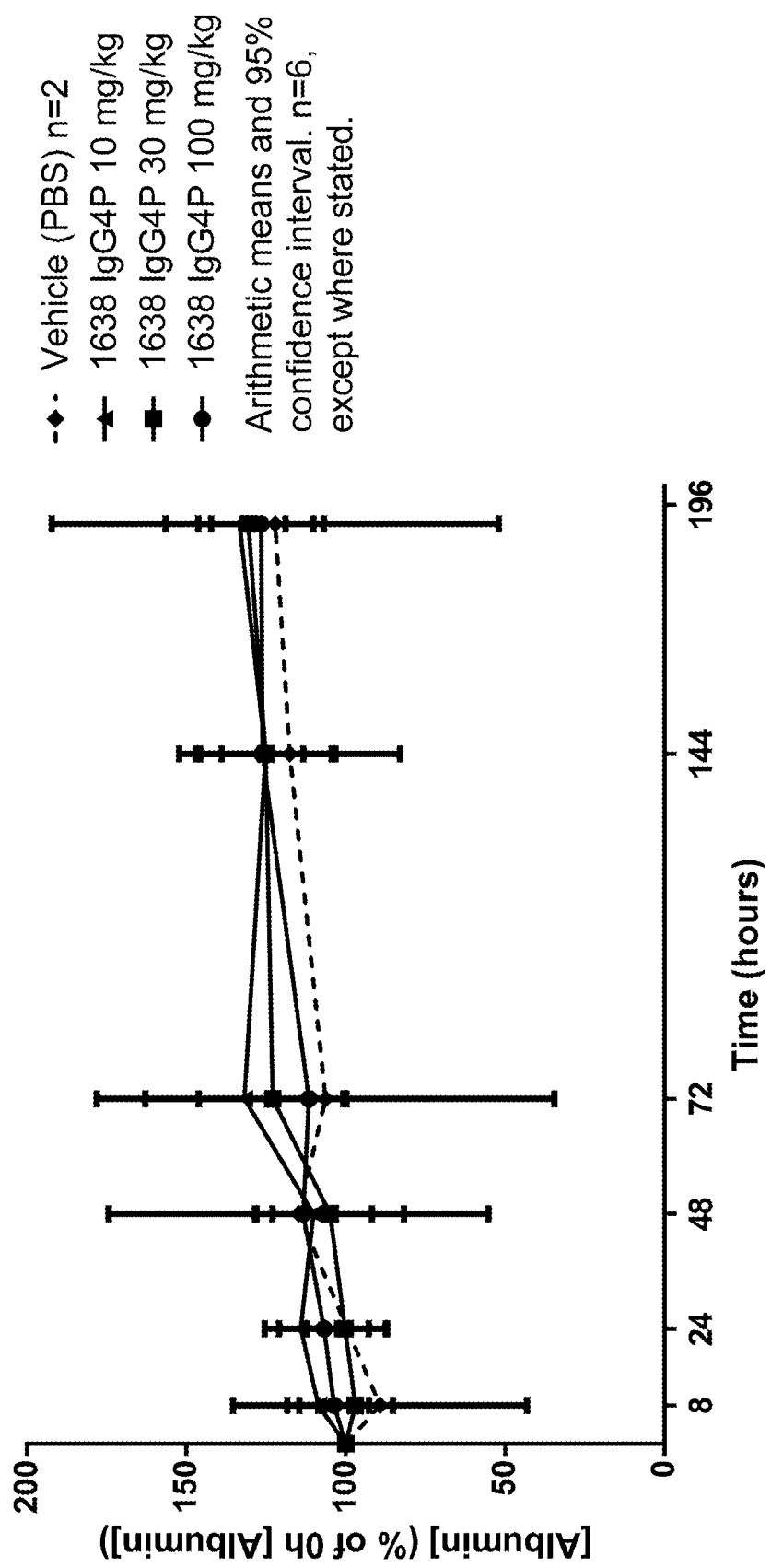
FIG. 1F    The effect of 1638 IgG4P format on the concentration of serum albumin in human FcRn-transgenic mice.

FIG. 2 shows representative binding curves for CA170_1638.g49 IgG4. The mean $K_D$ values (n = 3) were 0.20 in neutral buffer, & 0.22 in acidic buffer, respectively
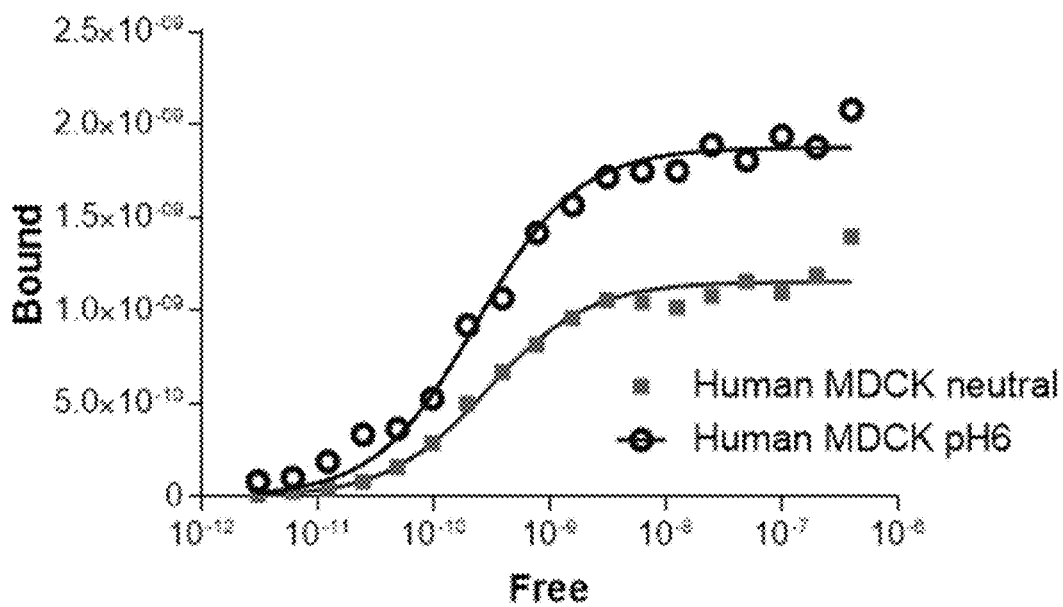
FIG. 3 shows CA170_1638.g49 IgG4 inhibits IgG recycling in MDCK II clone 15 cells.
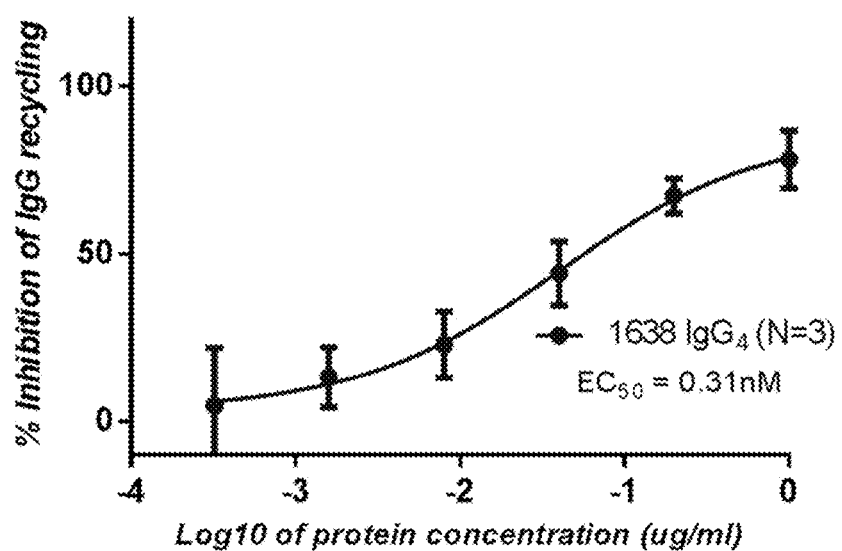

FIG. 4    shows CA170_1638.g49 IgG4 inhibits IgG transcytosis in MDCK II clone 15 cells.
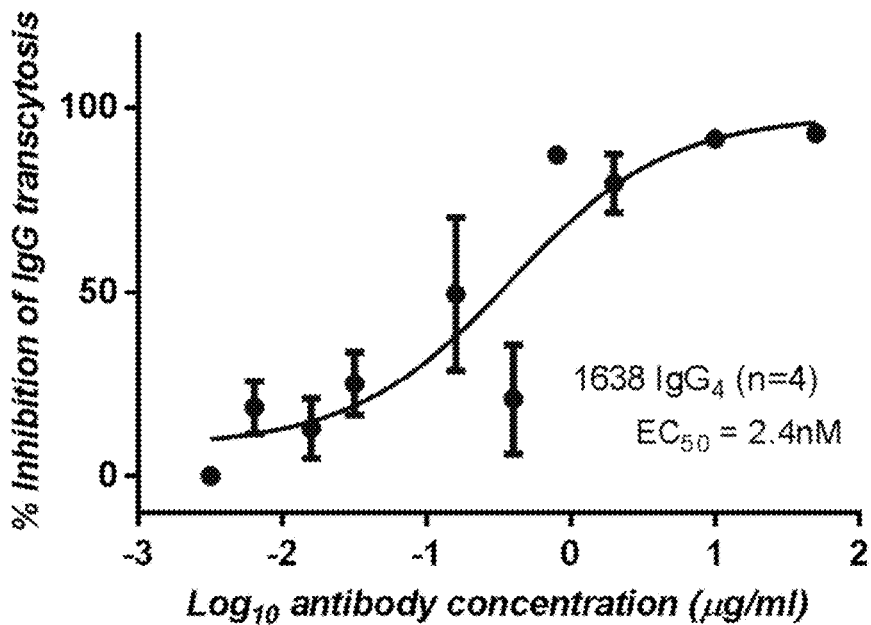
FIG. 5    shows CA170_1638.g49 FabFv inhibits IgG transcytosis in MDCK II clone 15 cells.
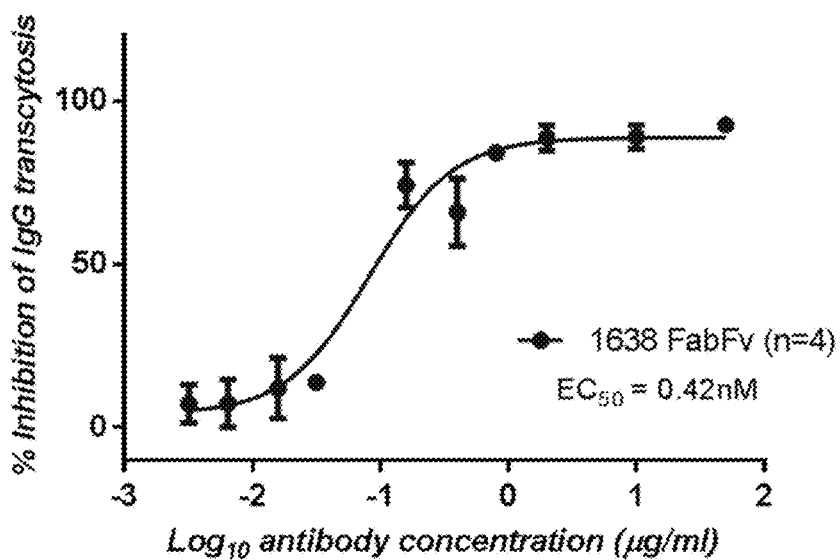

FIG. 6 shows CA170_1638.g49 IgG4 binding on MDCK II clone 40 cells in acidic and neutral pH.
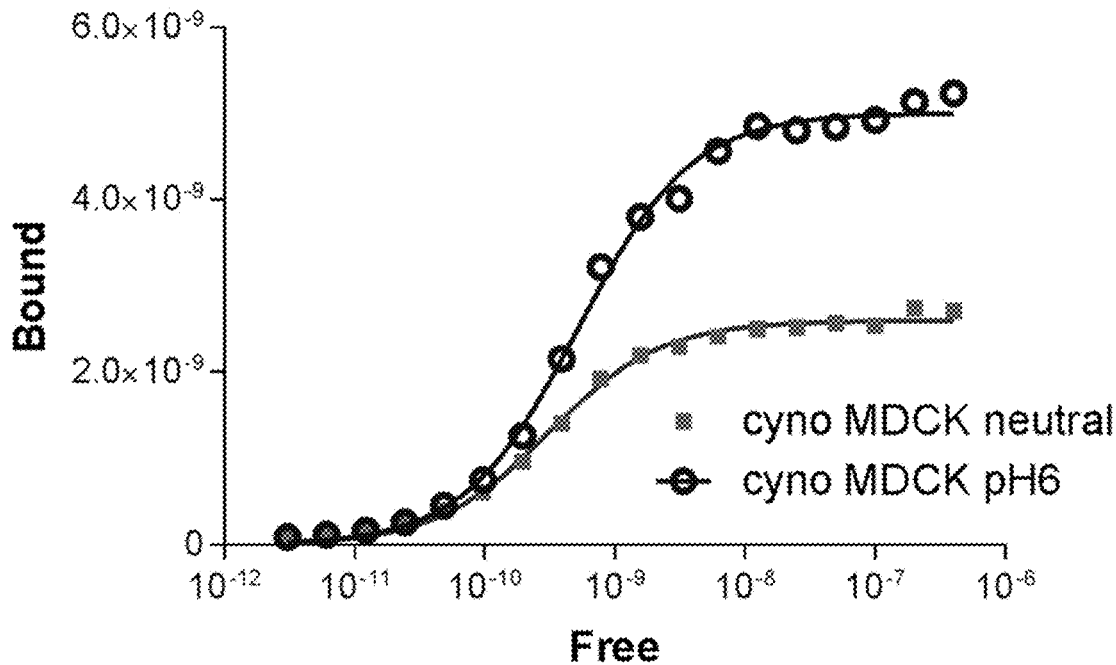
FIG. 7 CA170_1638 Ab sequences
CDRH1
GFSLSTYGVGVG            SEQ ID NO: 1
CDRH2
NIWWDDDKRYNPSLEN        SEQ ID NO: 2
CDRH3
TPAYYGSHPPFDY           SEQ ID NO: 3
CDRL1
RTSEDIYTNLA             SEQ ID NO: 4
CDRL2
VAKTLQD                 SEQ ID NO: 5
CDRL3
LQGFKFPWT               SEQ ID NO: 6
CDRL2 VARIANT
VAKTLQE                 SEQ ID NO: 7

FIG. 8A

Rat Ab 1638 VL region      SEQ ID NO: 8

DILMTQSPAS LSASLGETIS IECRTSEDIY TNLAWYQQKS GKSPQLLIYV AKTLQDGVPS
RFSGSGSGTH YSLKISGMQP EDEGDYFCLQ GFKFPWTFGG GTKLELK

Rat Ab 1638 VL region      SEQ ID NO: 9 gacatcctga tgacacagtc tccagcttcc ctgtctgcat ctctgggaga aactatctcc
atcgaatgtc gaacaagtga agacatttac actaatttag cgtggtacca gcagaagtca
gggaaatctc ctcaactcct gatctatgtt gcaaagacgt tgcaagatgg ggtcccatca
cggttcagtg gcagtggatc tggcacgcat tattctctca agatcagcgg catgcaacct
gaagatgaag gggattattt ctgtctgcag ggtttcaagt ttccgtggac gttcggtgga
ggcaccaagc tggaactgaa a

Rat Ab 1638 VL region with signal sequence underlined and italicised SEQ ID NO: 10

*MNVPTQFLGL LLLWITDGIC* DILMTQSPAS LSASLGETIS IECRTSEDIY TNLAWYQQKS
GKSPQLLIYV AKTLQDGVPS RFSGSGSGTH YSLKISGMQP EDEGDYFCLQ GFKFPWTFGG GTKLELK

Rat Ab 1638 VL region with signal sequence underlined and italicised SEQ ID NO: 11

*atgaatgtgc ccactcaatt ccttgggttg ttgctgctgt ggataacaga tggcatatgc*
gacatcctga tgacacagtc tccagcttcc ctgtctgcat ctctgggaga aactatctcc
atcgaatgtc gaacaagtga agacatttac actaatttag cgtggtacca gcagaagtca
gggaaatctc ctcaactcct gatctatgtt gcaaagacgt tgcaagatgg ggtcccatca
cggttcagtg gcagtggatc tggcacgcat tattctctca agatcagcgg catgcaacct
gaagatgaag gggattattt ctgtctgcag ggtttcaagt ttccgtggac gttcggtgga
ggcaccaagc tggaactgaa a

Rat Ab 1638 VH region SEQ ID NO: 12

QVTLKESGPG ILQPSQTLSL TCTFSGFSLS TYGVGVGWIR QPSGKGLEWL ANIWWDDDKR
YNPSLENRLT ISKDTSNNQA FLKITNVDTA DSATYFCVRT PAYYGSHPPF DYWGQGVMVT VS

Rat Ab 1638 VH region SEQ ID NO: 13 caggttactc tgaaagagtc tggccctggg atattgcagc cctcccagac cctcagtctg
acttgcactt tctctggttt tcactgagt acttatggtg tgggtgtggg ctggattcgt
cagccttcag ggaagggtct ggagtggctg gcaaacattt ggtgggatga tgataagcgc
tacaatccat ctctggaaaa ccgactcact atctccaagg acacctccaa caaccaagca
ttcctcaaga tcaccaatgt ggacactgca gatagcgcca catacttctg tgttcggacc
ccggcttact atggcagcca tccccctttt gactactggg gccaaggagt catggtcaca gtctcg

Rat Ab 1638 VH region with signal sequence underlined and italicised SEQ ID NO: 14

*MDRLTSSFLL LIVPAYVLSQ* VTLKESGPGI LQPSQTLSLT CTFSGFSLST YGVGVGWIRQ
PSGKGLEWLA NIWWDDDKRY NPSLENRLTI SKDTSNNQAF LKITNVDTAD SATYFCVRTP
AYYGSHPPFD YWGQGVMVTV S

Rat Ab 1638 VH region with signal sequence underlined and italicised SEQ ID NO: 15

*atggacaggc taacttcctc attcctactg ctgattgtcc ctgcatatgt cctgtct*cag
gttactctga aagagtctgg ccctgggata ttgcagccct cccagaccct cagtctgact
tgcactttct ctggttttc actgagtact tatggtgtgg gtgtgggctg gattcgtcag
ccttcaggga agggtctgga gtggctggca aacatttggt gggatgatga taagcgctac
aatccatctc tggaaaaccg actcactatc tccaaggaca cctccaacaa ccaagcattc
ctcaagatca ccaatgtgga cactgcagat agcgccacat acttctgtgt tcggacccg
gcttactatg gcagccatcc ccctttgac tactggggcc aaggagtcat ggtcacagtc tcg

FIG. 8B (signal sequences underlined and italicized)

1638 gL7 V-region SEQ ID NO: 16
```
DIQMTQSPSS LSASVGDRVT ITCRTSEDIY TNLAWYQQKP GKVPKLLIYV AKTLQEGVPS
RFSGSGSGTH YTLTISSLQP EDVATYYCLQ GFKFPWTFGG GTKVEIK
```

1638 gL7 V-region SEQ ID NO: 17
```
gatatccaga tgacccagag tccaagcagt ctctccgcca gcgtaggcga tcgtgtgact
attacctgtc gcactagcga ggacatctac accaacctgg cgtggtatca gcagaaacca
ggcaaagtgc cgaaactgct gatctacgtc gcgaaaaccc tccaggaagg tgtaccgtct
cgcttttccg gctctggtag cggtactcac tacaccctga ccatctcttc cctccagccg
gaagatgttg ctacctacta ttgcctccag ggcttcaaat tcccgtggac tttcggtggc
ggcacgaaag tggaaatcaa a
```

1638 gL7 V-region (*E. coli* expression) SEQ ID NO: 18
```
MKKTAIAIAV ALAGFATVAQ ADIQMTQSPS SLSASVGDRV TITCRTSEDI YTNLAWYQQK
PGKVPKLLIY VAKTLQEGVP SRFSGSGSGT HYTLTISSLQ PEDVATYYCL QGFKFPWTFG
GGTKVEIK
```

1638 gL7 V-region (*E. coli* expression) SEQ ID NO: 19
```
atgaaaaaga cagctatcgc aattgcagtg gccttggctg gtttcgctac cgtagcgcaa
gctgatatcc agatgaccca gagtccaagc agtctctccg ccagcgtagg cgatcgtgtg
actattacct gtcgcactag cgaggacatc tacaccaacc tggcgtggta tcagcagaaa
ccaggcaaag tgccgaaact gctgatctac gtcgcgaaaa ccctccagga aggtgtaccg
tctcgctttt ccggctctgg tagcggtact cactacaccc tgaccatctc ttccctccag
ccggaagatg ttgctaccta ctattgcctc cagggcttca aatcccgtg gactttcggt
ggcggcacga aagtggaaat caaa
```
1638 gL7 light chain (V + constant) SEQ ID NO: 20
```
DIQMTQSPSS LSASVGDRVT ITCRTSEDIY TNLAWYQQKP GKVPKLLIYV AKTLQEGVPS
RFSGSGSGTH YTLTISSLQP EDVATYYCLQ GFKFPWTFGG GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC
```

1638 gL7 light chain (V + constant, *E. coli* expression) SEQ ID NO: 21
```
gatatccaga tgacccagag tccaagcagt ctctccgcca gcgtaggcga tcgtgtgact
attacctgtc gcactagcga ggacatctac accaacctgg cgtggtatca gcagaaacca
ggcaaagtgc cgaaactgct gatctacgtc gcgaaaaccc tccaggaagg tgtaccgtct
cgcttttccg gctctggtag cggtactcac tacaccctga ccatctcttc cctccagccg
gaagatgttg ctacctacta ttgcctccag ggcttcaaat tcccgtggac tttcggtggc
ggcacgaaag tggaaatcaa acgtacggta gcggcccat ctgtcttcat cttcccgcca
tctgatgagc agttgaaatc tggaactgcc tctgttgtgt gcctgctgaa taacttctat
cccagagagg ccaaagtaca gtggaaggtg gataacgccc tccaatcggg taactcccag
gagagtgtca cagagcagga cagcaaggac agcacctaca gcctcagcag cacccgacg
ctgagcaaag cagactacga gaaacacaaa gtctacgcct gcgaagtcac ccatcaggc
ctgagctcac cagtaacaaa aagtttaat agaggggagt gt
```

FIG. 8C (signal sequence underlined and italicized)
1638 gL7 light chain (V + constant, mammalian expression) SEQ ID NO: 22

```
gatatccaga tgacccagag tccaagcagt ctctccgcca gcgtaggcga tcgtgtgact
attacctgtc gcactagcga ggacatctac accaacctgg cgtggtatca gcagaaacca
ggcaaagtgc cgaaactgct gatctacgtc gcgaaaccc  tccaggaagg tgtaccgtct
cgcttttccg gctctggtag cggtactcac tacaccctga ccatctcttc cctccagccg
gaagatgttg ctacctacta ttgcctccag ggcttcaaat cccgtggac  tttcggtggc
ggcacgaaag tggaaatcaa acggaccgtg gccgctccct ccgtgttcat cttcccaccc
tccgacgagc agctgaagtc cggcaccgcc tccgtcgtgt gcctgctgaa caacttctac
ccccgcgagg ccaaggtgca gtggaaggtg gacaacgccc tgcagtccgg caactcccag
gaatccgtca ccgagcagga ctccaaggac agcacctact ccctgtcctc caccctgacc
ctgtccaagg ccgactacga gaagcacaag gtgtacgcct gcgaagtgac ccaccagggc
ctgtccagcc ccgtgaccaa gtccttcaac cggggcgagt gc
```

1638 gL7 light chain (*E. coli* expression) SEQ ID NO: 23
*MKKTAIAIAV ALAGFATVAQ* ADIQMTQSPS SLSASVGDRV TITCRTSEDI YTNLAWYQQK
PGKVPKLLIY VAKTLQEGVP SRFSGSGSGT HYTLTISSLQ PEDVATYYCL QGFKFPWTFG
GGTKVEIKRT VAAPSVFIFP PSDEQLKSGT ASVVCLLNNF YPREAKVQWK VDNALQSGNS
QESVTEQDSK DSTYSLSSTL TLSKADYEKH KVYACEVTHQ GLSSPVTKSF NRGEC 1638 gL7 light chain (*E. coli* expression) SEQ ID NO: 24
```
atgaaaaaga cagctatcgc aattgcagtg gccttggctg gtttcgctac cgtagcgcaa
gctgatatcc agatgaccca gagtccaagc agtctctccg ccagcgtagg cgatcgtgtg
actattacct gtcgcactag cgaggacatc tacaccaacc tggcgtggta tcagcagaaa
ccaggcaaag tgccgaaact gctgatctac gtcgcgaaaa ccctccagga aggtgtaccg
tctcgctttt ccggctctgg tagcggtact cactacaccc tgaccatctc ttccctccag
ccggaagatg ttgctaccta ctattgcctc cagggcttca aattcccgtg gactttcggt
ggcggcacga aagtggaaat caaacgtacg gtagcggccc catctgtctt catcttcccg
ccatctgatg agcagttgaa atctggaact gcctctgttg tgtgcctgct gaataacttc
tatcccagag aggccaaagt acagtggaag gtggataacg ccctccaatc gggtaactcc
caggagagtg tcacagagca ggacagcaag gacagcacct acagcctcag cagcaccctg
acgctgagca aagcagacta cgagaaacac aaagtctacg cctgcgaagt cacccatcag
ggcctgagct caccagtaac aaaaagtttt aatagagggg agtgt
```

1638 gH33 V-region SEQ ID NO: 25
EVQLVESGGG LVQPGGSLRL SCAASGFSLS TYGVGVGWVR QAPGKGLEWL ANIWWDDDKR
YNPSLENRFT ISRDNAKNSA YLQMNSLRAE DTAVYYCART PAYYGSHPPF DYWGQGTMVT VS 1638 gH33 V-region SEQ ID NO: 26
```
gaggttcagc tggtcgagtc tggaggcggg cttgtccagc ctggagggag cctgcgtctc
tcttgtgcag cgtccggctt ctctctgtct acctacggcg ttggtgttgg ttgggtacgt
caggctccag gtaaaggtct ggaatggctc gcaaacatct ggtgggacga cgataaacgc
tacaacccgt ccctggagaa ccgcttcacc attagccgtg ataacgcgaa aaactccgcg
tatctccaga tgaactccct gcgtgccgaa gacacggctg tgtactattg cgcgcgcact
ccggcgtact atggctctca ccaccgtttt gattactggg gtcagggtac aatggttacc gtctcg
```

1638 gH33 V-region (*E. coli* expression) SEQ ID NO: 27
*MKKTAIAIAV ALAGFATVAQ* AEVQLVESGG GLVQPGGSLR LSCAASGFSL STYGVGVGWV
RQAPGKGLEW LANIWWDDDK RYNPSLENRF TISRDNAKNS AYLQMNSLRA EDTAVYYCAR
TPAYYGSHPP FDYWGQGTMV TVS

FIG. 8D (signal sequences underlined and italicized)
1638 gH33 V-region (*E.coli* expression) SEQ ID NO: 28
<u>*atgaagaaga ctgctatagc aattgcagtg gcgctagctg gtttcgccac cgtggcgcaa*</u>
<u>*gct*</u>gaggttc agctggtcga gtctggaggc gggcttgtcc agcctggagg gagcctgcgt
ctctcttgtg cagcgtccgg cttctctctg tctacctacg gcgttggtgt tggttgggta
cgtcaggctc aggtaaagg tctggaatgg ctcgcaaaca tctggtggga cgacgataaa
cgctacaacc cgtccctgga gaaccgcttc accattagcc gtgataacgc gaaaaactcc
gcgtatctcc agatgaactc cctgcgtgcc gaagacacgg ctgtgtacta ttgcgcgcgc
actccggcgt actatggctc tcacccaccg tttgattact ggggtcaggg taccatggtt
accgtctcg 1638 gH33 Fab heavy chain (V + human gamma-1 CH1) SEQ ID NO: 29
EVQLVESGGG LVQPGGSLRL SCAASGFSLS TYGVGVGWVR QAPGKGLEWL ANIWWDDDKR
YNPSLENRFT ISRDNAKNSA YLQMNSLRAE DTAVYYCART PAYYGSHPPF DYWGQGTMVT
VSSASTKGPS VFPLAPSSKS TSGGTAALGC LVKDYFPEPV TVSWNSGALT SGVHTFPAVL
QSSGLYSLSS VVTVPSSSLG TQTYICNVNH KPSNTKVDKK VEPKSC 1638 gH33 Fab heavy chain (V + human gamma-1 CH1) SEQ ID NO: 30
gaggttcagc tggtcgagtc tggaggcggg cttgtccagc ctggagggag cctgcgtctc
tcttgtgcag cgtccggctt ctctctgtct acctacggcg ttggtgttgg ttgggtacgt
caggctccag gtaaaggtct ggaatggctc gcaaacatct ggtgggacga cgataaacgc
tacaaccgt ccctggagaa ccgcttcacc attagccgtg ataacgcgaa aaactccgcg
tatctccaga tgaactccct gcgtgccgaa gacacggctg tgtactattg cgcgcgcact
ccggcgtact atggctctca cccaccgttt gattactggg gtcagggtac catggttacc
gtctcgagcg cttctacaaa gggcccatcg gtcttccccc tggcacctc ctccaagagc
acctctgggg gcacagcggc cctgggctgc ctggtcaagg actacttccc cgaaccggtg
acggtgtcgt ggaactcagg cgccctgacc agcggcgtgc acaccttccc ggctgtccta
cagtcctcag gactctactc cctcagcagc gtggtgaccg tgccctcca gcagcttggc
acccagacct acatctgcaa cgtgaatcac aagcccagca acaccaaggt cgacaagaaa
gttgagccca atcttgt 1638 gH33 Fab heavy chain with (E. coli expression) SEQ ID NO: 31
<u>*MKKTAIAIAV ALAGFATVAQ A*</u>EVQLVESGG GLVQPGGSLR LSCAASGFSL STYGVGVGWV
RQAPGKGLEW LANIWWDDDK RYNPSLENRF TISRDNAKNS AYLQMNSLRA EDTAVYYCAR
TPAYYGSHPP FDYWGQGTMV TVSSASTKGP SVFPLAPSSK STSGGTAALG CLVKDYFPEP
VTVSWNSGAL TSGVHTFPAV LQSSGLYSLS SVVTVPSSSL GTQTYICNVN HKPSNTKVDK KVEPKSC 1638 gH33 Fab heavy chain (E. coli expression) SEQ ID NO: 32
<u>*atgaagaaga ctgctatagc aattgcagtg gcgctagctg gtttcgccac cgtggcgcaa*</u>
<u>*gct*</u>gaggttc agctggtcga gtctggaggc gggcttgtcc agcctggagg gagcctgcgt
ctctcttgtg cagcgtccgg cttctctctg tctacctacg gcgttggtgt tggttgggta
cgtcaggctc aggtaaagg tctggaatgg ctcgcaaaca tctggtggga cgacgataaa
cgctacaacc cgtccctgga gaaccgcttc accattagcc gtgataacgc gaaaaactcc
gcgtatctcc agatgaactc cctgcgtgcc gaagacacgg ctgtgtacta ttgcgcgcgc
actccggcgt actatggctc tcacccaccg tttgattact ggggtcaggg taccatggtt
accgtctcga gcgcttctac aaagggccca tcggtcttcc cctggcacc ctcctccaag
agcacctctg gggcacagc ggccctgggc tgcctggtca aggactactt ccccgaaccg
gtgacggtgt cgtggaactc aggcgccctg accagcggcg tgcacacctt cccggctgtc
ctacagtcct caggactcta ctccctcagc agcgtggtga ccgtgccctc cagcagcttg
ggcacccaga cctacatctg caacgtgaat cacaagccca gcaacaccaa ggtcgacaag
aaagttgagc ccaaatcttg t

FIG. 8E (signal sequences underlined and italicized)

1638 gH33 Fab' heavy chain (V + human gamma-1 CH1 + hinge) SEQ ID NO: 33
```
EVQLVESGGG LVQPGGSLRL SCAASGFSLS TYGVGVGWVR QAPGKGLEWL ANIWWDDDKR
YNPSLENRFT ISRDNAKNSA YLQMNSLRAE DTAVYYCART PAYYGSHPPF DYWGQGTMVT
VSSASTKGPS VFPLAPSSKS TSGGTAALGC LVKDYFPEPV TVSWNSGALT SGVHTFPAVL
QSSGLYSLSS VVTVPSSSLG TQTYICNVNH KPSNTKVDKK VEPKSCDKTH TCAA
```

1638 gH33 Fab' heavy chain (V + human gamma-1 CH1 + hinge) SEQ ID NO: 34
```
gaggttcagc tggtcgagtc tggaggcggg cttgtccagc ctggagggag cctgcgtctc
tcttgtcag cgtccggctt ctctctgtct acctacggcg ttggtgttgg ttgggtacgt
caggctccag gtaaaggtct ggaatggctc gcaaacatct ggtgggacga cgataaacgc
tacaacccgt ccctggagaa ccgcttcacc attagccgtg ataacgcgaa aaactccgcg
tatctccaga tgaactccct gcgtgccgaa gacacggctg tgtactattg cgcgcgcact
ccggcgtact atggctctca ccaccgtttt gattactggg gtcagggtac catggttacc
gtctcgagcg cttctacaaa gggcccatcg gtcttccccc tggcaccctc ctccaagagc
acctctgggg gcacagcggc cctgggctgc ctggtcaagg actacttccc cgaaccggtg
acggtgtcgt ggaactcagg cgccctgacc agcggcgtgc acaccttccc ggctgtccta
cagtcctcag gactctactc cctcagcagc gtggtgaccg tgcctccag cagcttgggc
acccagacct acatctgcaa cgtgaatcac aagcccagca acaccaaggt cgacaagaaa
gttgagccca atcttgtga caaaactcac acatgcgccg cg
```

1638 gH33 Fab' heavy chain (E. coli expression) SEQ ID NO: 35
```
MKKTAIAIAV ALAGFATVAQ AEVQLVESGG GLVQPGGSLR LSCAASGFSL STYGVGVGWV
RQAPGKGLEW LANIWWDDDK RYNPSLENRF TISRDNAKNS AYLQMNSLRA EDTAVYYCAR
TPAYYGSHPP FDYWGQGTMV TVSSASTKGP SVFPLAPSSK STSGGTAALG CLVKDYFPEP
VTVSWNSGAL TSGVHTFPAV LQSSGLYSLS SVVTVPSSSL GTQTYICNVN HKPSNTKVDK
KVEPKSCDKT HTCAA
```

1638 gH33 Fab' heavy chain (E. coli expression) SEQ ID NO: 36
```
atgaagaaga ctgctatagc aattgcagtg gcgctagctg gtttcgccac cgtggcgcaa
gctgaggttc agctggtcga gtctggaggc gggcttgtcc agcctggagg gagcctgcgt
ctctcttgtg cagcgtccgg cttctctctg tctacctacg gcgttggtgt tggttgggta
cgtcaggctc aggtaaagg tctggaatgg ctcgcaaaca tctggtggga cgacgataaa
cgctacaacc cgtccctgga gaaccgcttc accattagcc gtgataacgc gaaaaactcc
gcgtatctcc agatgaactc cctgcgtgcc gaagacacgg ctgtgtacta ttgcgcgcgc
actccggcgt actatggctc tcacccaccg tttgattact ggggtcaggg taccatggtt
accgtctcga gcgcttctac aaagggccca tcggtcttcc ccctggcacc ctcctccaag
agcacctctg ggggcacagc ggccctgggc tgcctggtca aggactactt ccccgaaccg
gtgacggtgt cgtggaactc aggcgccctg accagcggcg tgcacacctt cccggctgtc
ctacagtcct caggactcta ctccctcagc agcgtggtga ccgtgccctc agcagcttg
ggcacccaga cctacatctg caacgtgaat cacaagccca gcaacaccaa ggtcgacaag
aaagttgagc ccaaatcttg tgacaaaact cacacatgcg ccgcg
```

1638 gH33 IgG4 heavy chain (V + human gamma-4P constant) SEQ ID NO: 37
```
EVQLVESGGG LVQPGGSLRL SCAASGFSLS TYGVGVGWVR QAPGKGLEWL ANIWWDDDKR
YNPSLENRFT ISRDNAKNSA YLQMNSLRAE DTAVYYCART PAYYGSHPPF DYWGQGTMVT
VSSASTKGPS VFPLAPCSRS TSESTAALGC LVKDYFPEPV TVSWNSGALT SGVHTFPAVL
QSSGLYSLSS VVTVPSSSLG TKTYTCNVDH KPSNTKVDKR VESKYGPPCP PCPAPEFLGG
PSVFLFPPKP KDTLMISRTP EVTCVVVDVS QEDPEVQFNW YVDGVEVHNA KTKPREEQFN
STYRVVSVLT VLHQDWLNGK EYKCKVSNKG LPSSIEKTIS KAKGQPREPQ VYTLPPSQEE
MTKNQVSLTC LVKGFYPSDI AVEWESNGQP ENNYKTTPPV LDSDGSFFLY SRLTVDKSRW
QEGNVFSCSV MHEALHNHYT QKSLSLSLGK
```

FIG. 8F (signal sequences underlined and italicized)

1638 gH33 IgG4 heavy chain (V + human gamma-4P constant) SEQ ID NO: 38
```
gaggttcagc tggtcgagtc tggaggcggg cttgtccagc ctggagggag cctgcgtctc
tcttgtgcag cgtccggctt ctctctgtct acctacggcg ttggtgttgg ttgggtacgt
caggctccag gtaaaggtct ggaatggctc gcaaacatct ggtgggacga cgataaacgc
tacaacccgt ccctggagaa ccgcttcacc attagccgtg ataacgcgaa aaactccgcg
tatctccaga tgaactccct gcgtgccgaa gacacggctg tgtactattg cgcgcgcact
ccggcgtact atggctctca cccaccgttt gattactggg gtcagggtac aatggttacc
gtctcgtctg cctccaccaa gggcccctcc gtgttcctc tggcccttg ctccggtcc
acctccgagt ctaccgccgc tctgggctgc ctggtcaagg actacttccc cgagccgtg
acagtgtcct ggaactctgg cgccctgacc tccggcgtgc acccttccc tgccgtgctg
cagtcctccg gcctgtactc cctgtcctcc gtcgtgaccg tgccctcctc cagcctgggc
accaagacct acacctgtaa cgtggaccac aagccctcca acaccaaggt ggacaagcgg
gtggaatcta agtacggccc tcctgcccc ccctgccctg ccctgaatt tctgggcgga
ccttccgtgt tcctgttccc cccaaagccc aaggacaccc tgatgatctc ccggacccc
gaagtgacct gcgtggtggt ggacgtgtcc caggaagatc ccgaggtcca gttcaattgg
tacgtggacg gcgtggaagt gcacaatgcc aagaccaagc ccagagagga cagttcaac
tccacctacc gggtggtgtc cgtgctgacc gtgctgcacc aggactggct gaacggcaaa
gagtacaagt gcaaggtgtc caacaagggc ctgccctcca gcatcgaaaa gaccatctcc
aaggccaagg gccagccccg cgagcccag gtgtacaccc tgcccctag ccaggaagag
atgaccaaga accaggtgtc cctgacctgt ctggtcaagg gcttctaccc ctccgacatt
gccgtggaat gggagtccaa cggccagccc gagaacaact acaagaccac ccccctgtg
ctggacagcg acggctcctt cttcctgtac tctcggctga ccgtggacaa gtcccggtgg
caggaaggca acgtcttctc ctgctccgtg atgcacgagg ccctgcacaa ccactacacc
cagaagtccc tgtccctgag cctgggcaag
```

1638 gH33 IgG4 heavy chain (V + human gamma-4P constant mammalian, no c-terminal lys) SEQ ID NO: 39
```
EVQLVESGGGLV QPGGSLRLSC AASGFSLSTY GVGVGWVRQA PGKGLEWLAN IWWDDDKRYN
PSLENRFTIS RDNAKNSAYL QMNSLRAEDT AVYYCARTPA YYGSHPPFDY WGQGTMVTVS
SASTKGPSVF PLAPCSRSTS ESTAALGCLV KDYFPEPVTV SWNSGALTSG VHTFPAVLQS
SGLYSLSSVV TVPSSSLGTK TYTCNVDHKP SNTKVDKRVE SKYGPPCPPC PAPEFLGGPS
VFLFPPKPKD TLMISRTPEV TCVVVDVSQE DPEVQFNWYV DGVEVHNAKT KPREEQFNST
YRVVSVLTVL HQDWLNGKEY KCKVSNKGLP SSIEKTISKA KGQPREPQVY TLPPSQEEMT
KNQVSLTCLV KGFYPSDIAV EWESNGQPEN NYKTTPPVLD SDGSFFLYSR LTVDKSRWQE
GNVFSCSVMH EALHNHYTQK SLSLSLG
```

1638 gL7 FabFv light chain SEQ ID NO: 40
```
DIQMTQSPSS LSASVGDRVT ITCRTSEDIY TNLAWYQQKP GKVPKLLIYV AKTLQEGVPS
RFSGSGSGTH YTLTISSLQP EDVATYYCLQ GFKFPWTFGG GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGECGGGGSG GGGSGGGGSD IQMTQSPSSV
SASVGDRVTI TCQSSPSVWS NFLSWYQQKP GKAPKLLIYE ASKLTSGVPS RFSGSGSGTD
FTLTISSLQP EDFATYYCGG GYSSISDTTF GCGTKVEIKR T
```

FIG. 8G (signal sequences underlined and italicized)

1638 gL7 FabFv light chain SEQ ID NO: 41
```
gatatccaga tgacccagag tccaagcagt ctctccgcca cgtaggcga tcgtgtgact
attacctgtc gcactagcga ggacatctac accaacctgg cgtggtatca gcagaaacca
ggcaaagtgc cgaaactgct gatctacgtc gcgaaaaccc tccaggaagg tgtaccgtct
cgcttttccg gctctggtag cggtactcac tacaccctga ccatctcttc cctccagccg
gaagatgttg ctacctacta ttgcctccag ggcttcaaat tcccgtggac tttcggtggc
ggcacgaaag tggaaatcaa acgtacggta gcggcccat ctgtcttcat cttcccgcca
tctgatgagc agttgaaatc tggaactgcc tctgttgtgt gcctgctgaa taacttctat
cccagagagg ccaaagtaca gtggaaggtg gataacgccc tccaatcggg taactcccag
gagagtgtca cagagcagga cagcaaggac agcacctaca gcctcagcag caccctgacg
ctgagcaaag cagactacga gaaacacaaa gtctacgcct gcgaagtcac ccatcaggcc
ctgagctcgc ccgtcacaaa gagcttcaac aggggagagt gtggtggagg tggctctggc
ggtggtggct ccggaggcgg aggaagcgac atccagatga cccagagccc ttcctctgta
agcgccagtg tcggagacag agtgactatt acctgccaaa gctccccttc agtctggtcc
aattttctat cctggtatca gcaaaagccc ggaaaggctc ctaaattgct gatctacgaa
gcaagcaaac tcaccagcgg cgtgcccagc aggttcagcg gcagtgggtc tggaactgac
tttaccctga caatctcctc actccagccc gaggacttcg ccacctatta ctgcggtgga
ggttacagta gcataagtga tacgacattt ggatgcggca taaagtgga aatcaagcgt acc
```

1638 gH33 FabFv heavy chain SEQ ID NO: 42
```
EVQLVESGGG LVQPGGSLRL SCAASGFSLS TYGVGVGWVR QAPGKGLEWL ANIWWDDDKR
YNPSLENRFT ISRDNAKNSA YLQMNSLRAE DTAVYYCART PAYYGSHPPF DYWGQGTMVT
VSSASTKGPS VFPLAPSSKS TSGGTAALGC LVKDYFPEPV TVSWNSGALT SGVHTFPAVL
QSSGLYSLSS VVTVPSSSLG TQTYICNVNH KPSNTKVDKK VEPKSCSGGG GSGGGGTGGG
GSEVQLLESG GGLVQPGGSL RLSCAVSGID LSNYAINWVR QAPGKCLEWI GIIWASGTTF
YATWAKGRFT ISRDNSKNTV YLQMNSLRAE DTAVYYCART VPGYSTAPYF DLWGQGTLVT VSS
```

1638 gH33 FabFv heavy chain SEQ ID NO: 43
```
gaggttcagc tggtcgagtc tggaggcggg cttgtccagc ctggagggag cctgcgtctc
tcttgtgcag cgtccggctt ctctctgtct acctacggcg ttggtgttgg ttgggtacgt
caggctccag gtaaaggtct ggaatggctc gcaaacatct ggtgggacga cgataaacgc
tacaacccgt ccctggagaa ccgcttcacc attagccgtg ataacgcgaa aaactccgcg
tatctccaga tgaactccct gcgtgccgaa gacacggctg tgtactattg cgcgcgcact
ccggcgtact atggctctca ccaccgtttt gattactggg gtcagggtac aatggttacc
gtctcgtccg cttctacaaa gggcccatcg gtcttccccc tggcaccctc ctccaagagc
acctctgggg gcacagcggc cctgggctgc ctggtcaagg actacttccc cgaaccggtg
acggtgtcgt ggaactcagg cgccctgacc agcggcgtgc acaccttccc ggctgtccta
cagtcctctg gactctactc cctcagcagc gtggtgaccg tgccctccag cagcttgggc
acccagacct acatctgcaa cgtgaatcac aagcccagca acaccaaggt ggacaagaaa
gttgagccca atcttgttc cggaggtggc ggttccggag tggcggtac aggtggcggt
gggtccgaag tccagctgct tgaatccgga ggcggactcg tgcagcccgg aggcagtctt
cgcttgtcct gcgctgtatc tggaatcgac ctgagcaatt acgccatcaa ctgggtgaga
caggcacctg gaaatgcct cgaatggatc ggcattatat gggctagtgg gacgacttt
tatgctacat gggcgaaggg tagattcaca atctcacggg ataatagtaa gaacacagtg
tacctgcaga tgaactccct gcgagcagag gataccgccg tttactattg tgctcgcact
gtcccaggtt atagcactgc accctacttt gatctgtggg ggcagggcac tctggtcacc
gtctcgtcc
```

Human IGKV1-27 JK4 acceptor framework SEQ ID NO: 44
```
DIQMTQSPSS LSASVGDRVT ITCRASQGIS NYLAWYQQKP GKVPKLLIYA ASTLQSGVPS
RFSGSGSGTD FTLTISSLQP EDVATYYCQK YNSAPLTFGG GTKVEIK
```

FIG. 8H (signal sequences underlined and italicized)

Human IGKV1-27 JK4 acceptor framework SEQ ID NO: 45
```
gacatccaga tgacccagtc tccatcctcc ctgtctgcat ctgtaggaga cagagtcacc
atcacttgcc gggcgagtca gggcattagc aattatttag cctggtatca gcagaaacca
gggaaagttc ctaagctcct gatctatgct gcatccactt tgcaatcagg ggtcccatct
cggttcagtg gcagtggatc tgggacagat ttcactctca ccatcagcag cctgcagcct
gaagatgttg caacttatta ctgtcaaaag tataacagtg cccctctcac tttcggcgga
gggaccaagg tggagatcaa a
```

Human IGHV3-7 JH3 acceptor framework SEQ ID NO: 46
```
EVQLVESGGG LVQPGGSLRL SCAASGFTFS SYWMSWVRQA PGKGLEWVAN IKQDGSEKYY
VDSVKGRFTI SRDNAKNSLY LQMNSLRAED TAVYYCARDA FDVWGQGTMV TVSS
```

Human IGHV3-7 JH3 acceptor framework SEQ ID NO: 47
```
gaggtgcagc tggtggagtc tgggggaggc ttggtccagc ctggggggtc cctgagactc
tcctgtgcag cctctggatt caccttagt agctattgga tgagctgggt ccgccaggct
ccagggaagg ggctggagtg ggtggccaac ataaagcaag atggaagtga gaaatactat
gtggactctg tgaagggccg attcaccatc tccagagaca acgccaagaa ctcactgtat
ctgcaaatga acagcctgag agccgaggac acggctgtgt attactgtgc gagagatgct
tttgatgtct ggggccaagg gacaatggtc accgtctctt ca
```

Human FcRn alpha chain extracellular sequence SEQ ID NO: 48
```
AESHLSLLYH LTAVSSPAPG TPAFWVSGWL GPQQYLSYNS LRGEAEPCGA WVWENQVSWY
WEKETTDLRI KEKLFLEAFK ALGGKGPYTL QGLLGCELGP DNTSVPTAKF ALNGEEFMNF
DLKQGTWGGD WPEALAISQR WQQQDKAANK ELTFLLFSCP HRLREHLERG RGNLEWKEPP
SMRLKARPSS PGFSVLTCSA FSFYPPELQL RFLRNGLAAG TGQGDFGPNS DGSFHASSSL
TVKSGDEHHY CCIVQHAGLA QPLRVELESP AKSS
```

Rat β2M SEQ ID NO:49
```
IQKTPQIQVY SRHPPENGKP NFLNCYVSQF HPPQIEIELL KNGKKIPNIE MSDLSFSKDW
SFYILAHTEF TPTETDVYAC RVKHVTLKEP KTVTWDRDM
```

Human β2M including signal sequence SEQ ID NO:50
```
MSRSVALAVL ALLSLSGLEA IQRTPKIQVY SRHPAENGKS NFLNCYVSGF HPSDIEVDLL
KNGERIEKVE HSDLSFSKDW SFYLLYYTEF TPTEKDEYAC RVNHVTLSQP KIVKWDRDM
```

1638gL2 V-region SEQ ID NO: 51
```
DIQMTQSPSS LSASVGDRVT ITCRTSEDIY TNLAWYQQKP GKVPKLLIYV AKTLQDGVPS
RFSGSGSGTH YTLTISSLQP EDVATYYCLQ GFKFPWTFGG GTKVEIK
```

1638gL2 V-region SEQ ID NO: 52
```
gatatccaga tgacccagag tccaagcagt ctctccgcca gcgtaggcga tcgtgtgact
attacctgtc gcactagcga ggacatctac accaacctgg cgtggtatca gcagaaacca
ggcaaagtgc cgaaactgct gatctacgtc gcgaaaaccc tccaggacgg tgtaccgtct
cgcttttccg gctctggtag cggtactcac tacaccctga ccatctcttc cctccagccg
gaagatgttg ctacctacta ttgcctccag ggcttcaaat cccgtggac tttcggtggc
ggcacgaaag tggaaatcaa a
```

FIG. 8I (1638.g28 = gL2 gH2) signal sequence underlined and italicized 1638 gL2 V-region (*E. coli* expression) SEQ ID NO: 53
<u>*MKKTAIAIAV ALAGFATVAQ A*</u>DIQMTQSPS SLSASVGDRV TITCRTSEDI YTNLAWYQQK
PGKVPKLLIY VAKTLQDGVP SRFSGSGSGT HYTLTISSLQ PEDVATYYCL QGFKFPWTFG
GGTKVEIK 1638 gL2 V-region (*E. coli* expression) SEQ ID NO: 54
<u>*atgaaaaaga cagctatcgc aattgcagtg gccttggctg gtttcgctac cgtagcgcaa
gct*</u>gatatcc agatgaccca gagtccaagc agtctctccg ccagcgtagg cgatcgtgtg
actattacct gtcgcactag cgaggacatc tacaccaacc tggcgtggta tcagcagaaa
ccaggcaaag tgccgaaact gctgatctac gtcgcgaaaa ccctccagga cggtgtaccg
tctcgctttt ccggctctgg tagcggtact cactacaccc tgaccatctc ttccctccag
ccggaagatg ttgctaccta ctattgcctc cagggcttca aattcccgtg gactttcggt
ggcggcacga agtggaaat caaa 1638 gL2 light chain (V + constant) SEQ ID NO: 55
DIQMTQSPSS LSASVGDRVT ITCRTSEDIY TNLAWYQQKP GKVPKLLIYV AKTLQDGVPS
RFSGSGSGTH YTLTISSLQP EDVATYYCLQ GFKFPWTFGG GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC 1638 gL2 light chain (V + constant, codon optimized for *E. coli* expression) SEQ ID NO: 56
gatatccaga tgacccagag tccaagcagt ctctccgcca gcgtaggcga tcgtgtgact
attacctgtc gcactagcga ggacatctac accaacctgg cgtggtatca gcagaaacca
ggcaaagtgc cgaaactgct gatctacgtc gcgaaaaccc tccaggacgg tgtaccgtct
cgcttttccg gtctggtag cggtactcac tacaccctga ccatctcttc cctccagccg
gaagatgttg ctacctacta ttgcctccag ggcttcaaat cccgtggac tttcggtggc
ggcacgaaag tggaaatcaa acgtacggta gcggcccat ctgtcttcat cttcccgcca
tctgatgagc agttgaaatc tggaactgcc tctgttgtgt gcctgctgaa taacttctat
cccagagagg ccaaagtaca gtggaaggtg ataacgccc tccaatcggg taactcccag
gagagtgtca cagagcagga cagcaaggac agcacctaca gcctcagcag caccctgacg
ctgagcaaag cagactacga gaaacacaaa gtctacgcct gcgaagtcac ccatcagggc
ctgagctcac cagtaacaaa aagttttaat agagggagt gt 1638 gL2 light chain (*E. coli* expression) SEQ ID NO: 57
<u>*MKKTAIAIAV ALAGFATVAQ A*</u>DIQMTQSPS SLSASVGDRV TITCRTSEDI YTNLAWYQQK
PGKVPKLLIY VAKTLQDGVP SRFSGSGSGT HYTLTISSLQ PEDVATYYCL QGFKFPWTFG
GGTKVEIKRT VAAPSVFIFP PSDEQLKSGT ASVVCLLNNF YPREAKVQWK VDNALQSGNS
QESVTEQDSK DSTYSLSSTL TLSKADYEKH KVYACEVTHQ GLSSPVTKSF NRGEC

FIG. 8J 1638 gL2 light chain (*E. coli* expression) SEQ ID NO: 58
<u>*atgaaaaaga cagctatcgc aattgcagtg gccttggctg gtttcgctac cgtagcgcaa*
*gct*</u>gatatcc agatgaccca gagtccaagc agtctctccg ccagcgtagg cgatcgtgtg
actattacct gtcgcactag cgaggacatc tacaccaacc tggcgtggta tcagcagaaa
ccaggcaaag tgccgaaact gctgatctac gtcgcgaaaa ccctccagga cggtgtaccg
tctcgctttt ccggctctgg tagcggtact cactcaccc tgaccatctc ttccctccag
ccggaagatg ttgctaccta ctattgcctc cagggcttca aatcccgtg gactttcggt
ggcggcacga agtggaaat caaacgtacg gtagcggccc catctgtctt catcttcccg
ccatctgatg agcagttgaa atctggaact gcctctgttg tgtgcctgct gaataacttc
tatcccagag aggccaaagt acagtggaag gtggataacg ccctccaatc gggtaactcc
caggagagtg tcacagagca ggacagcaag gacagcacct acagcctcag cagcaccctg
acgctgagca agcagacta cgagaaacac aaagtctacg cctgcgaagt cacccatcag
ggcctgagct caccagtaac aaaaagtttt aatagagggg agtgt 1638gH2 V-region SEQ ID NO: 59
EVQLVESGGG LVQPGGSLRL SCAFSGFSLS TYGVGVGWVR QAPGKGLEWL ANIWWDDDKR
YNPSLENRFT ISKDTAKNSA YLQMNSLRAE DTAVYYCVRT PAYYGSHPPF DYWGQGTMVT VS 1638gH2 V-region SEQ ID NO: 60
gaggttcagc tggtcgagtc tggaggcggg cttgtccagc ctggagggag cctgcgtctc
tcttgtgcat tctccggctt ctctctgtct acctacggcg ttggtgttgg ttgggtacgt
caggctccag gtaaaggtct ggaatggctc gcaaacatct ggtgggacga cgataaacgc
tacaacccgt ccctggagaa ccgcttcacc attagcaaag ataccgcgaa aaactccgcg
tatctccaga tgaactccct cgtgccgaa gacacggctg tgtactattg cgttcgcact
ccggcgtact atggctctca cccaccgttt gattactggg gtcagggtac catggttacc gtctcg 1638 gH2 V-region with signal sequence underlined and italicized (*E. coli* expression) SEQ ID NO: 61
<u>*MKKTAIAIAV ALAGFATVAQ A*</u>EVQLVESGG GLVQPGGSLR LSCAFSGFSL STYGVGVGWV
RQAPGKGLEW LANIWWDDDK RYNPSLENRF TISKDTAKNS AYLQMNSLRA EDTAVYYCVR
TPAYYGSHPP FDYWGQGTMV TVS 1638 gH2 V-region with signal sequence underlined and italicized (*E. coli* expression) SEQ ID NO: 62
<u>*atgaagaaga ctgctatagc aattgcagtg gcgctagctg gtttcgccac cgtggcgcaa*
*gct*</u>gaggttc agctggtcga gtctggaggc gggcttgtcc agcctggagg gagcctgcgt
ctctcttgtg cattctccgg cttctctctg tctacctacg gcgttggtgt tggttgggta
cgtcaggctc caggtaaagg tctggaatgg ctcgcaaaca tctggtggga cgacgataaa
cgctacaacc cgtccctgga gaaccgcttc accattagca aagataccgc gaaaaactcc
gcgtatctcc agatgaactc cctcgtgccg aagacacgg ctgtgtacta ttgcgttcgc
actccggcgt actatggctc tcacccaccg tttgattact ggggtcaggg taccatggtt
accgtctcg 1638 gH2 Fab' heavy chain (V + human gamma-1 CH1 + hinge) SEQ ID NO: 63
EVQLVESGGG LVQPGGSLRL SCAFSGFSLS TYGVGVGWVR QAPGKGLEWL ANIWWDDDKR
YNPSLENRFT ISKDTAKNSA YLQMNSLRAE DTAVYYCVRT PAYYGSHPPF DYWGQGTMVT
VSSASTKGPS VFPLAPSSKS TSGGTAALGC LVKDYFPEPV TVSWNSGALT SGVHTFPAVL
QSSGLYSLSS VVTVPSSSLG TQTYICNVNH KPSNTKVDKK VEPKSCDKTH TCAA

FIG. 8K signal sequence underlined and italicized 1638 gH2 Fab' heavy chain (V + human gamma-1 CH1 + hinge) SEQ ID NO: 64
```
gaggttcagc tggtcgagtc tggaggcggg cttgtccagc ctggagggag cctgcgtctc
tcttgtgcat tctccggctt ctctctgtct acctacggcg ttggtgttgg ttgggtacgt
caggctccag gtaaaggtct ggaatggctc gcaaacatct ggtgggacga cgataaacgc
tacaacccgt ccctggagaa ccgcttcacc attagcaaag ataccgcgaa aaactccgcg
tatctccaga tgaactccct gcgtgccgaa gacacggctg tgtactattg cgttcgcact
ccggcgtact atggctctca cccaccgttt gattactggg gtcagggtac catggttacc
gtctcgagcg cttctacaaa gggcccatcg gtcttccccc tggcaccctc ctccaagagc
acctctgggg gcacagcggc cctgggctgc ctggtcaagg actacttccc cgaaccggtg
acggtgtcgt ggaactcagg cgccctgacc agcggcgtgc acaccttccc ggctgtccta
cagtcctcag gactctactc cctcagcagc gtggtgaccg tgccctccag cagcttggcc
acccagacct acatctgcaa cgtgaatcac aagcccagca acaccaaggt cgacaagaaa
gttgagccca atcttgtgca aaaactcac acatgcgccg cg
```

1638 gH2 Fab' heavy chain (*E. coli* expression) SEQ ID NO: 65
*MKKTAIAIAV ALAGFATVAQ* AEVQLVESGG GLVQPGGSLR LSCAFSGFSL STYGVGVGWV
RQAPGKGLEW LANIWWDDDK RYNPSLENRF TISKDTAKNS AYLQMNSLRA EDTAVYYCVR
TPAYYGSHPP FDYWGQGTMV TVSSASTKGP SVFPLAPSSK STSGGTAALG CLVKDYFPEP
VTVSWNSGAL TSGVHTFPAV LQSSGLYSLS SVVTVPSSSL GTQTYICNVN HKPSNTKVDK
KVEPKSCDKT HTCAA 1638 gH2 Fab' heavy chain d (*E. coli* expression) SEQ ID NO: 66
<u>*atgaagaaga ctgctatagc aattgcagtg gcgctagctg gtttcgccac cgtggcgcaa
gct*</u>gaggttc agctggtcga gtctggaggc gggcttgtcc agcctggagg gagcctgcgt
ctctcttgtg cattctccgg cttctctctg tctacctacg gcgttggtgt tggttgggta
cgtcaggctc caggtaaagg tctggaatgg ctcgcaaaca tctggtggga cgacgataaa
cgctacaacc cgtccctgga gaaccgcttc accattagca agataccgc gaaaaactcc
gcgtatctcc agatgaactc cctgcgtgcc gaagacacgg ctgtgtacta ttgcgttcgc
actccggcgt actatggctc tcacccaccg tttgattact ggggtcaggg taccatggtt
accgtctcga gcgcttctac aaagggccca tcggtcttcc cctggcacc ctcctccaag
agcacctctg ggggcacagc ggccctgggc tgcctggtca aggactactt ccccgaaccg
gtgacggtgt cgtggaactc aggcgccctg accagcggcg tgcacacctt cccggctgtc
ctacagtcct caggactcta ctccctcagc agcgtggtga ccgtgccctc cagcagcttg
ggcacccaga cctacatctg caacgtgaat cacaagccca gcaacaccaa ggtcgacaag
aaagttgagc ccaaatcttg tgacaaaact cacacatgcg ccgcg Human β2-microglobulin SEQ ID NO: 72
IQRTPKIQVYSRHPAENGKSNFLNCYVSGFHPSDIEVDLLKNGERIEKVEHSDLSFSKDWSFYLLYYTEFTPT
EKDEYACRVNHVTLSQPKIVKWDRDM

FIG. 8L

1638gH33 IgG1 heavy chain (V + human gamma-1 constant) SEQ ID NO: 73

```
EVQLVESGGG LVQPGGSLRL SCAASGFSLS TYGVGVGWVR QAPGKGLEWL
ANIWWDDDKR YNPSLENRFT ISRDNAKNSA YLQMNSLRAE DTAVYYCART
PAYYGSHPPF DYWGQGTMVT VSSASTKGPS VFPLAPSSKS TSGGTAALGC
LVKDYFPEPV TVSWNSGALT SGVHTFPAVL QSSGLYSLSS VVTVPSSSLG
TQTYICNVNH KPSNTKVDKK VEPKSCDKTH TCPPCPAPEL LGGPSVFLFP
PKPKDTLMIS RTPEVTCVVV DVSHEDPEVK FNWYVDGVEV HNAKTKPREE
QYNSTYRVVS VLTVLHQDWL NGKEYKCKVS NKALPAPIEK TISKAKGQPR
EPQVYTLPPS RDELTKNQVS LTCLVKGFYP SDIAVEWESN GQPENNYKTT
PPVLDSDGSF FLYSKLTVDK SRWQQGNVFS CSVMHEALHN HYTQKSLSLS
PGK
```

1638gH33 IgG1 heavy chain (V + human gamma-1 constant, exons underlined) SEQ ID NO: 74

```
gaggttcagc tggtcgagtc tgggaggcgg cttgtccagc ctggagggag cctgcgtctc tcttgtgcag cgtccggctt ctctctgtct acctacggcg
ttggtgttgg ttgggtacgt caggctccag gtaaagtct gaatggctc gcaaacatct gtggacga cgataaccgt cctgagaa
ccgcttcacc attagccgtg ataaacgcg aactccaga tatctccaga gtctgccgaa gacacggctg tgtactattg cgcgcgact
ccggcgtact atggctctca ccaccgtt gattactggg gtcagggac aatggttacc gtctcgagcg ctttctacaa gggccatcg gtcttccc
tgccacctc ctccagagc acctctggggg gcacagcggc ctgggctgc ctgggcggtg gactcttcc cgaaccggtg acggtgtcgt ggaactcagg
cgccctgacc agcggcgtgc acacctcca ggctgtccta cagtcctcag gactctact cctcagcagc gttggtgacc tgcctccag cagtcttggc
acccagacct acatctgcaa cgtgaatcac aagcccagca acaccaaggt cgacaagaaa gttgcagg agcaaggcag gcccgtctg cctctcacc cggaggcctc
gaagccaggg catccgaca cgacctctc tgcctgggct tcttctgct cgggaggacc agtcagccag gctctgggca ggacaggct agtgccctc tgcacacaa ctgcacacca
tgcccgccg actcatgct agggagagga ctctctgct cggggagac gtaactccca cctaagcca acctctctc acaaaactca cacatgccca cgtgcccag
agggcaggt gctgggtca ttctcctc ccagatctga gtaactcga caggcggga atcctctctc aggtgccct agagtagcct cagtccaggg acaggcccca gccgggtgct gacacgtcca
ctcggacacc ccaggccctg ccctcagcg cctgaactcc tgggggacc gtcagtcttc ctcttccccc caaaaaccctc ctgtgacgc gactggctga atggcaagga ggacccctga
gtaagccagg gtgtggtgg acgtgagcca cacggaacag agtacaacag cccagagcgt gcaagtcac agcccatgg agcagtccag tccagtcttc atcagtcacc
cctccaatct ttcctcagca cctgaactc tgggggacc gaagccaca gaggtcaagt tcaactggta cgtggacgc gactggctga atggcaagga ggacccctga
ggtcacatgc gtggtggtgg agtacagg cacgtgagcc agtacaacag cacacaggct ccagagcgt acaactacaa gaccacggtc gtgactcac agccctcga
cggaggagc cccagccctg agtacaacag cccagagcgt gcaagctggc gaagtcacc aaccaccgta gacaccaggt ctccccgg gggcgagg tccgtgagg gccaca
acaaagccct cccagcccc atcgagaaa accatctcca agccaaagg
```

FIG. 8L (cont.)

```
cctctgccct gagagtgacc gctgtaccaa cctctgtccc tacagggcag ccccgagaac cacccctgccc ccatcccggg atgagctgac
caagaaccag gtcagcctga cctgcctggt caaaggcttc tatcccagcg acatcgccgt ggagtgggag agcaatgggc agccggagaa caactacaag
accacgcctc ccgtgctgga ctccgacggc tccttcttcc tctacagcaa gctcaccgtg gacaagagca gtggcagca gggaacgtc ttctcatgct
ccgtgatgca tgaggctctg cacaaccact acacgcagaa gagcctctcc ctgtctccgg gtaaa
```

FIG. 9A

LIGHT CHAIN Graft 1638

```
              1         5        10        15        20        25        30        35        40        45        50        55        60        65        70        75        80        85        90        95       100       105
Light 1638    DILMTQSPASLSASLGETISIECRTSEDIYTNLAWYQQKSGKSPQLLIYVAKTLQDGVPSRFSGSGSGTHYSLKISGMQPEDEGYFCLQGFKFPWTFGGGTKLELK
                 ||||  |||||    | ||||| |||||||||||| ||||| ||||||| |||||||  ||| ||  ||||| ||||| ||||||||||||||
IGKV1-27      DIQMTQSPSSLSASVGDRVTITCRASQGISNYLAWYQQKPGKVPKLLIYAASTLQSGVPSRFSGSGSGTDFTLTISSLQPEDVATYYCQKYNSAPLTFGGGTKVEIK
                 ||||||||||||||||||||||   |||||  ||||||| |||||||||||| |||||||||||||| ||||||||||||||||           |||||||||
1638gL7       DIQMTQSPSSLSASVGDRVTITCRTSEDIYTNLAWYQQKPGKVPKLLIYVAKTLQEGVPSRFSGSGSGTHYLTISSLQPEDVATYYCLQGFKFPWTFGGGTKVEIK
```

Legend

1638 = Rat variable light chain sequence
1638gL7 = Humanized graft of 1638 variable light chain using IGKV1-27 human germline as the acceptor framework.
CDRs are shown in bold/underlined
Donor residues are shown in bold/italic and are highlighted: H70 and Y71
The mutation in CDRL2 to remove a potential Aspartic acid isomerization site is shown in bold/underlined and is highlighted: E56

FIG. 9B

HEAVY CHAIN Graft 1638

```
              1         5        10        15        20        25        30        35        40        45        50   a   55        60        65        70        75        80 abc 85        90        95       100       105       110
Heavy 1638    QVTLKESGPGILQPSQTLSLTCTFSGFSLSTYGVGVGWIRQPSGKGLEWLANIW-WDDDKRYNPSLENRLTISKDTSNNQAFLKITNVDTADSATYFCVRTPAYYGSHPPFDYWGQGVMVTVS
              ||| ||||| ||| |  ||| ||  ||||||||||||| |||||||||| ||| ||||||||||||| ||| |||  ||| |  |||  ||||||| ||||            |||| |||||||
IGHV3-7       EVQLVESGGGLVQPGGSLRLSCAASGFTFSS--YWMSWVRQAPGKGLEWVANIKQDGSEEKYYVDSVKGRFTISRDNAKNSLYLQMNSLRAEDTAVYYCAR-------DAFDVWGQGTMVTVS
              ||||||||||||||||||||||||||     ||||||||||||||||  ||||||||||||||||||||||||||||||||||| |||||||||||||          ||||||| |||||||
1638gH33      EVQLVESGGGLVQPGGSLRLSCAASGFSLSTYGVGVGWVRQAPGKGLEWLANIW-WDDDKRYNPSLENRFTISRDNAKNSAYLQMNSLRAEDTAVYYCARTPAYYGSHPPFDYWGQGTMVTVS
```

Legend

1638 = Rat variable heavy chain sequence
1638gH33 = Humanized graft of 1638 variable heavy chain using IGHV3-7 human germline as the acceptor framework.
CDRs are shown in bold/underlined
Donor residues are shown in bold/italic and are highlighted: L48 and A78

ANTIBODIES SPECIFIC TO FCRN

CROSS-REFERENCE TO RELATED APPLICATIONS

The present application is a Divisional Application under 35 U.S.C. § 120 of U.S. application Ser. No. 15/036,209, filed May 12, 2016, which is the U.S. National Phase under 35 U.S.C. § 371 of PCT International Application No. PCT/EP2014/074409, filed Nov. 12, 2014, which claims priority to GB 1320066.2, filed Nov. 12, 2013, all of which are incorporated herein by reference in their entirety. The disclosure relates to antibodies specific to FcRn, formulations comprising the same, use of each in therapy, processes for expressing and optionally formulating said antibody, DNA encoding the antibodies and hosts comprising said DNA.

FcRn is a non-covalent complex of membrane protein FcRn α chain and β2 microglobulin (β2M). In adult mammals FcRn plays a key role in maintaining serum antibody levels by acting as a receptor that binds and salvages antibodies of the IgG isotype. IgG molecules are endocytosed by endothelial cells, and if they bind to FcRn, are recycled transcytosed out into, for example circulation. In contrast, IgG molecules that do not bind to FcRn enter the cells and are targeted to the lysosomal pathway where they are degraded. A variant IgG1 in which His435 is mutated to alanine results in the selective loss of FcRn binding and a significantly reduced serum half-life (Firan et al. 2001, International Immunology 13:993).

It is hypothesised that FcRn is a potential therapeutic target for certain autoimmune disorders caused at least in part by autoantibodies. The current treatment for certain such disorders includes plasmapheresis. Sometimes the plasmapheresis is employed along with immunosuppressive therapy for long-term management of the disease. Plasma exchange offers the quickest short-term answer to removing harmful autoantibodies. However, it may also be desirable to suppress the production of autoantibodies by the immune system, for example by the use of medications such as prednisone, cyclophosphamide, cyclosporine, mycophenolate mofetil, rituximab or a mixture of these.

Examples of diseases that can be treated with plasmapheresis include: Guillain-Barré syndrome; Chronic inflammatory demyelinating polyneuropathy; Goodpasture's syndrome; hyperviscosity syndromes; cryoglobulinemia; paraproteinemia; Waldenström macroglobulinemia; myasthenia gravis; thrombotic thrombocytopenic purpura (TTP)/hemolytic uremic syndrome; Wegener's granulomatosis; Lambert-Eaton Syndrome; antiphospholipid antibody syndrome (APS or APLS); microscopic polyangiitis; recurrent focal and segmental glomerulosclerosis in the transplanted kidney; HELLP syndrome; PANDAS syndrome; Refsum disease; Behcet syndrome; HIV-related neuropathy; Graves' disease in infants and neonates; pemphigus vulgaris; multiple sclerosis, rhabdomyolysis and alloimune diseases.

Plasmapheresis is sometimes used as a rescue therapy for removal of Fc containing therapeutics, for example in emergencies to reduced serious side effects.

Though plasmapheresis is helpful in certain medical conditions there are potential risks and complications associated with the therapy. Insertion of a rather large intravenous catheter can lead to bleeding, lung puncture (depending on the site of catheter insertion), and, if the catheter is left in too long, it can lead to infection and/or damage to the veins giving limited opportunity to repeat the procedure.

The procedure has further complications associated with it, for example when a patient's blood is outside of the body passing through the plasmapheresis instrument, the blood has a tendency to clot. To reduce this tendency, in one common protocol, citrate is infused while the blood is running through the circuit. Citrate binds to calcium in the blood, calcium being essential for blood to clot. Citrate is very effective in preventing blood from clotting; however, its use can lead to life-threateningly low calcium levels. This can be detected using the Chvostek's sign or Trousseau's sign. To prevent this complication, calcium is infused intravenously while the patient is undergoing the plasmapheresis; in addition, calcium supplementation by mouth may also be given.

Other complications of the procedure include: hypotension; potential exposure to blood products, with risk of transfusion reactions or transfusion transmitted diseases, suppression of the patient's immune system and bleeding or hematoma from needle placement.

Additionally facilities that provide plasmapheresis are limited and the procedure is very expensive.

An alternative to plasmapheresis is intravenous immunoglobulin (IVIG), which is a blood product containing pooled polyclonal IgG extracted from the plasma of over one thousand blood donors. The therapy is administered intravenously and lasts in the region of 2 weeks to 3 months.

Complications of the IVIG treatment include headaches, dermatitis, viral infection from contamination of the therapeutic product, for example HIV or hepatitis, pulmonary edema, allergic reactions, acute renal failure, venous thrombosis and aseptic meningitis.

Thus there is a significant unmet need for therapies for autoimmune disorders which are less invasive and which expose the patients to less medical complications.

Thus there is a significant unmet need for therapies for immunological disorders and/or autoimmune disorders which are less invasive and which expose the patients to less medical complications.

Accordingly agents that block or reduce the binding of IgG to FcRn may be useful in the treatment or prevention of such autoimmune and inflammatory diseases. Anti-FcRn antibodies have been described previously in WO2009/131702, WO2007/087289 and WO2006/118772.

However, there remains a need for improved anti-FcRn antibodies.

SUMMARY OF THE DISCLOSURE

Thus in one aspect there is provided an anti-FcRn antibody or binding fragment thereof comprising a heavy chain or heavy chain fragment having a variable region, wherein said variable region comprises one, two or three CDRs independently selected from SEQ ID NO: 1, SEQ ID NO: 2 and SEQ ID NO: 3, for example wherein CDR H1 is SEQ ID NO: 1, CDR H2 is SEQ ID NO: 2 and/or CDR H3 is SEQ ID NO: 3.

Thus one embodiment CDR H1 is SEQ ID NO: 1 and CDR H2 is SEQ ID NO: 2, or CDR H1 is SEQ ID NO: 1 and CDR H3 is SEQ ID NO: 3, or CDR H2 is SEQ ID NO: 2 and CDR H3 is SEQ ID NO: 3.

In another aspect there is provided an antibody or fragment comprising a sequence or combinations of sequences as defined herein, for example a cognate pair variable region.

The antibodies of the disclosure block binding of IgG to FcRn and are thought to be useful in reducing one or more biological functions of FcRn, including reducing half-life of circulating antibodies. This may be beneficial in that it allows the patient to more rapidly clear antibodies, such as autoantibodies. Accordingly antibodies of the disclosure reduce binding of IgG to FcRn.

Importantly the antibodies of the present invention are able to bind human FcRn, for example at both pH6 and pH7.4 with comparable and high binding affinity. Advantageously therefore the antibodies are able to continue to bind FcRn even within the endosome, thereby maximising the blocking of FcRn binding to IgG.

In one embodiment the antibodies or binding fragments according to the present disclosure comprise a light chain or light chain fragment having a variable region, for example comprising one, two or three CDRs independently selected from SEQ ID NO: 4, SEQ ID NO: 5 or SEQ ID NO: 7 and SEQ ID NO: 6, in particular wherein CDR L1 is SEQ ID NO: 4, CDR L2 is SEQ ID NO: 5 or SEQ ID NO: 7 and CDR L3 is SEQ ID NO: 6.

Thus one embodiment CDR L1 is SEQ ID NO: 4 and CDR L2 is SEQ ID NO: 5 or SEQ ID NO: 7, or CDR L1 is SEQ ID NO: 1 and CDR L3 is SEQ ID NO: 6, or CDR L2 is SEQ ID NO: 5 or SEQ ID NO: 7 and CDR L3 is SEQ ID NO:6.

In one embodiment the antibodies or binding fragments according to the present disclosure comprise CDR sequences selected from SEQ ID NOs: 1 to 7, for example wherein CDR H1 is SEQ ID NO: 1, CDR H2 is SEQ ID NO: 2, CDR H3 is SEQ ID NO: 3, CDR L1 is SEQ ID NO: 4, CDR L2 is SEQ ID NO: 5 or SEQ ID NO: 7 and CDR L3 is SEQ ID NO: 6.

Also provided is an antibody or binding fragment that binds the same epitope as an antibody or binding fragment explicitly disclosed herein. Accordingly there is provided an anti-FcRn antibody or binding fragment thereof which binds an epitope of human FcRn which comprises one, two, three, or four amino acids selected from the group consisting of residues E115, W131, P132, and E133 of human FcRn extracellular domain (SEQ ID NO: 48) and wherein the anti-FcRn antibody or binding fragment thereof further binds one or more (such as all) residues selected from the group consisting of A81, G83, G84, K85, G86, P87, N113, L135, A136, and Q139 and optionally further binds one or more residues selected from the group consisting of L82, Y88, L112 and D130.

In one embodiment there is provided an antibody or binding fragment that cross-blocks an antibody or binding fragment explicitly disclosed herein to human FcRn, or is cross-blocked from binding human FcRn by said antibody.

In one embodiment antibodies and binding fragments of the present disclosure block binding of human IgG to human FcRn.

In one embodiment antibodies and binding fragments of the present disclosure do not bind β2 microglobulin.

In one embodiment antibodies and binding fragments of the present disclosure do not bind human β2 microglobulin In one example antibodies and binding fragments of the present disclosure do not reduce circulating albumin levels by more than 50%, preferably by no more than 25%.

In one example antibodies and binding fragments of the present disclosure do not reduce circulating albumin levels.

The disclosure also extends to a polynucleotide, such as DNA, encoding an antibody or fragment as described herein, for example where the DNA is incorporated into a vector.

Also provided is a host cell comprising said polynucleotide.

Methods of expressing an antibody or fragment are provided herein as are methods of conjugating an antibody or fragment to a polymer, such as PEG.

The present disclosure also relates to pharmaceutical compositions comprising said antibodies and fragments.

In one embodiment there is provided a method of treatment comprising administering a therapeutically effective amount of an antibody, fragment or composition as described herein.

The present disclosure also extends to an antibody, fragment or composition according to the present disclosure for use in treatment, particularly in the treatment of an immunological and/or autoimmune disorder.

Thus the present disclosure provides antibodies, fragments thereof and methods for removal of pathogenic IgG, which is achieved by accelerating the body's natural mechanism for catabolising IgG.

In essence the antibodies and fragments according to the disclosure block the system that recycles IgG in the body.

The present therapy is likely to provide a replacement or supplement for certain diseases where plasmapheresis is a therapy or IVIg therapy, which is advantageous for patients.

BRIEF DESCRIPTION OF THE FIGURES

FIG. 1A shows the effect of 1638 IgG4P format on the concentration of human IVIg in serum of human FcRn-transgenic mice.

FIG. 1B shows the effect of 1638 FabFv and Fab'PEG formats on the concentration of human IVIg in human FcRn-transgenic mice FIG. 1C shows the pharmacokinetics of 1638 IgG4P format in human FcRn-transgenic mice.

FIG. 1D shows the pharmacokinetics of 1638 FabFv and Fab'PEG formats in human FcRn-transgenic mice FIG. 1E The effect of 1638 FabFv and Fab'PEG formats on the concentration of serum albumin in human FcRn-transgenic mice.

FIG. 1F The effect of 1638 IgG4P format on the concentration of serum albumin in human FcRn-transgenic mice.

FIG. 2 shows representative binding curves for CA170_1638.g49 IgG4. The mean KD values (n=3) were 0.20 nM in neutral buffer, & 0.22 nM in acidic buffer, respectively FIG. 3 shows CA170_1638.g49 IgG4 inhibits IgG recycling in MDCK II clone 15 cells FIG. 4 shows CA1701638.g49 IgG4 inhibits IgG transcytosis in MDCK II clone 15 cells.

FIG. 5 shows CA170_1638.g49 FabFv inhibits IgG transcytosis in MDCK II clone 15 cells.

FIG. 6 shows representative binding curves for CA170_1638.g49 IgG4. The mean KD values (n=3) were 0.3 in neutral buffer, and 0.43 in acidic buffer, respectively (see Table 2).

FIG. 7 shows CA170_1638 CDR sequences

FIGS. 8A-L Antibody sequences according to the present disclosure

FIG. 9A Humanisation of antibody 1638.g49

FIG. 9B Humanisation of antibody 1638.g49

DETAILS OF THE DISCLOSURE

Figure 1:
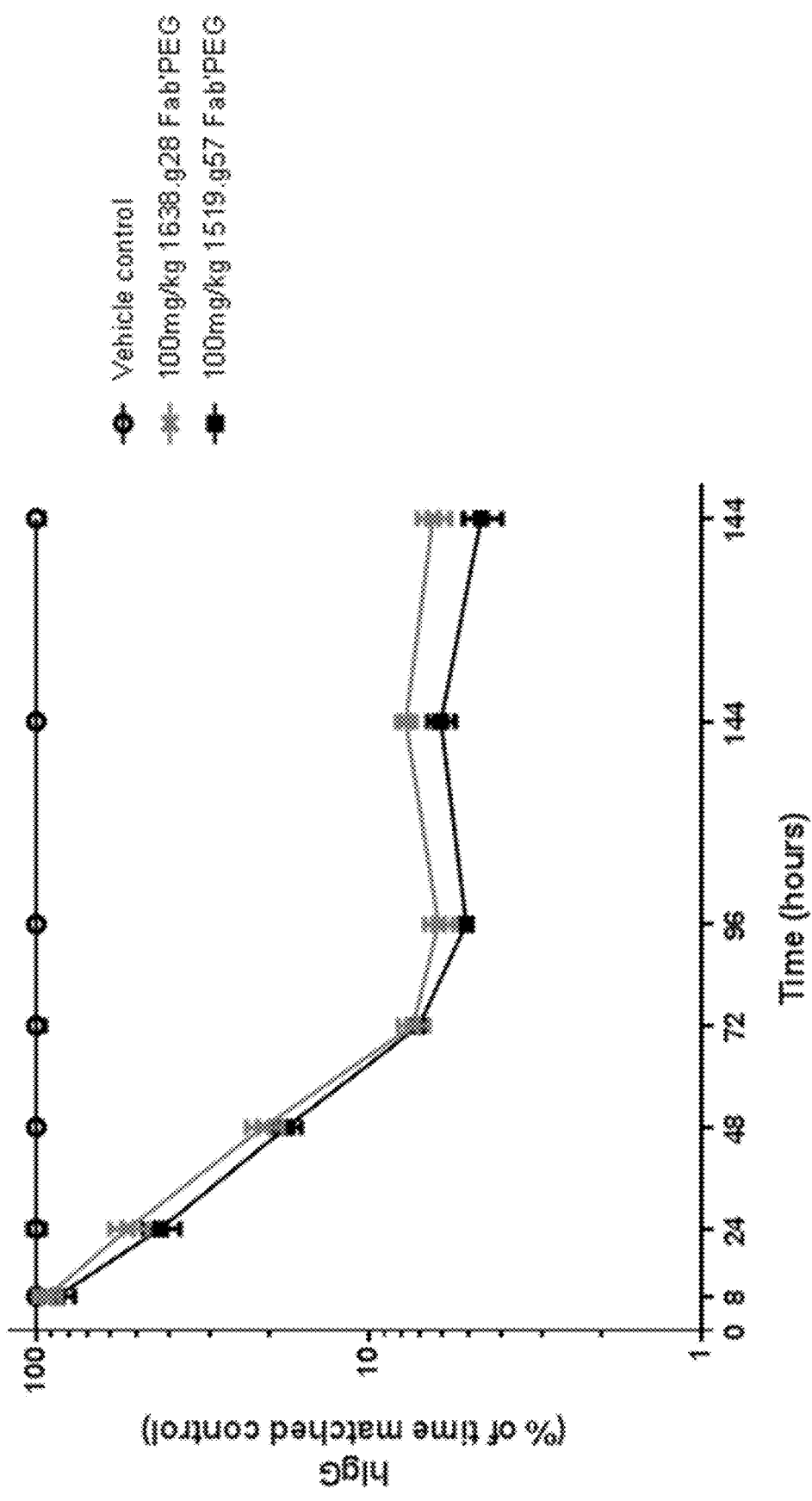
FIG. 1 Shows % hIgG in transgenic mice determined by LC-MS/MS

FcRn as employed herein refers to the non-covalent complex between the human IgG receptor alpha chain, also known as the neonatal Fc receptor, the amino acid sequence of which is in UniProt under number P55899, the extracellular domain of which is provided in FIG. 8 (SEQ ID NO:48), together with human β2 microglobulin (β2M), the amino acid sequence of which is in UniProt under number P61769 (provided herein with signal peptide (SEQ ID NO:50), without signal peptide (SEQ ID NO:72)).

Antibody molecule as employed herein refers to an antibody or binding fragment thereof.

The term 'antibody' as used herein generally relates to intact (whole) antibodies i.e. comprising the elements of two heavy chains and two light chains. The antibody may comprise further additional binding domains, for example as per the molecule DVD-Ig as disclosed in WO 2007/024715, or the so-called (FabFv)$_2$Fc described in WO2011/030107. Thus antibody as employed herein includes bi, tri or tetravalent full length antibodies.

Binding fragments of antibodies include single chain antibodies (i.e. a full length heavy chain and light chain); Fab, modified Fab, Fab', modified Fab', F(ab')$_2$, Fv, Fab-Fv, Fab-dsFv, single domain antibodies (e.g. VH or VL or VHH), scFv, dsscFv, bi, tri or tetra-valent antibodies, Bis-scFv, diabodies, tribodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilised versions thereof, the Fab-dsFv was first disclosed in WO2010/035012. Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO92/22583 and WO05/113605). One such example of the latter is a Tri-Fab (or TFM) as described in WO92/22583.

In one embodiment there is provided a Fab fragment.

In one embodiment there is provided a Fab' fragment.

A typical Fab' molecule comprises a heavy and a light chain pair in which the heavy chain comprises a variable region $V_H$, a constant domain $C_H1$ and a natural or modified hinge region and the light chain comprises a variable region $V_L$ and a constant domain $C_L$.

In one embodiment there is provided a dimer of a Fab' according to the present disclosure to create a F(ab')$_2$ for example dimerisation may be through the hinge.

In one embodiment the antibody or binding fragment thereof comprises a binding domain. A binding domain will generally comprises 6 CDRs, three from a heavy chain and three from a light chain. In one embodiment the CDRs are in a framework and together form a variable region. Thus in one embodiment an antibody or binding fragment comprises a binding domain specific for antigen comprising a light chain variable region and a heavy chain variable region.

It will be appreciated that one or more (for example 1, 2, 3 or 4) amino acid substitutions, additions and/or deletions may be made to the CDRs or other sequences (e.g variable domains) provided by the present invention without significantly altering the ability of the antibody to bind to FcRn. The effect of any amino acid substitutions, additions and/or deletions can be readily tested by one skilled in the art, for example by using the methods described herein, in particular in the Examples, to determine FcRn binding/blocking.

In one or more (for example 1, 2, 3 or 4) amino acid substitutions, additions and/or deletions may be made to the framework region employed in the antibody or fragment provided by the present invention and wherein binding affinity to FcRn is retained or increased.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

Antibodies and fragments of the present disclosure block FcRn and may thereby prevent it functioning in the recycling of IgG. Blocking as employed herein refers to physically blocking such as occluding the receptor but will also include where the antibody or fragments binds an epitope that causes, for example a conformational change which means that the natural ligand to the receptor no longer binds. Antibody molecules of the present invention bind to FcRn and thereby decrease or prevent (e.g. inhibit) FcRn binding to an IgG constant region.

In one embodiment the antibody or fragment thereof binds FcRn competitively with respect to IgG.

In one example the antibody or binding fragment thereof functions as a competitive inhibitor of human FcRn binding to human IgG. In one example the antibody or binding fragment thereof binds to the IgG binding site on FcRn. In one example the antibody blocks the IgG binding site. In one example the antibody or binding fragment thereof does not bind β2M.

Antibodies for use in the present disclosure may be obtained using any suitable method known in the art. The FcRn polypeptide/protein including fusion proteins, cells (recombinantly or naturally) expressing the polypeptide (such as activated T cells) can be used to produce antibodies which specifically recognise FcRn, alone or incombination with β2M. The polypeptide may be the 'mature' polypeptide or a biologically active fragment or derivative thereof. The human protein is registered in Swiss-Prot under the number P55899. The extracellular domain of human FcRn alpha chain is provided in SEQ ID NO: 48. The sequence of mature human β2M is provided in SEQ ID NO: 72.

In one embodiment the antigen is a mutant form of FcRn which is engineered to present FcRn on the surface of a cell, such that there is little or no dynamic processing where the FcRn is internalised in the cell, for example this can be achieved by making a mutation in the cytoplasmic tail of the FcRn alpha chain, wherein di-leucine is mutated to di-alanine as described in Ober et al 2001 Int. Immunol. 13, 1551-1559.

Polypeptides, for use to immunize a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The FcRn polypeptide may in some instances be part of a larger protein such as a fusion protein for example fused to an affinity tag or similar.

Antibodies generated against the FcRn polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377.

Screening for antibodies can be performed using assays to measure binding to human FcRn and/or assays to measure the ability to block IgG binding to the receptor. An example of a binding assay is an ELISA, in particular, using a fusion protein of human FcRn and human Fc, which is immobilized on plates, and employing a secondary antibody to detect anti-FcRn antibody bound to the fusion protein. Examples of suitable antagonistic and blocking assays are described herein below.

Specific as employed herein is intended to refer to an antibody that only recognises the antigen to which it is specific or an antibody that has significantly higher binding affinity to the antigen to which it is specific compared to binding to antigens to which it is non-specific, for example at least 5, 6, 7, 8, 9, 10 times higher binding affinity. Binding affinity may be measured by techniques such as BIAcore as described herein below. In one example the antibody of the present invention does not bind β2 microglobulin (32M). In one example the antibody of the present invention binds cynomolgus FcRn. In one example the antibody of the present invention does not bind rat or mouse FcRn.

The amino acid sequences and the polynucleotide sequences of certain antibodies according to the present disclosure are provided and form an aspect of the invention.

In one embodiment the antibodies or binding fragments according to the present disclosure are fully human, for example prepared from a phage library or similar.

In one example the antibodies are rodent, such as rat derived and comprise the light chain variable domain sequence given in SEQ ID NO:8 and the heavy chain variable domain sequence given in SEQ ID NO:12.

In one embodiment the antibody or fragments according to the disclosure are humanised.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived. The latter are often referred to as donor residues.

Thus in one embodiment as used herein, the term 'humanised antibody molecule' refers to an antibody molecule wherein the heavy and/or light chain contains one or more CDRs (including, if desired, one or more modified CDRs) from a donor antibody (e.g. a non-human antibody such as a murine monoclonal antibody) grafted into a heavy and/or light chain variable region framework of an acceptor antibody (e.g. a human antibody) optionally further comprising one or more framework residues derived from the non-human species from which the CDRs were derived (donor residues). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions.

Suitably, the humanised antibody according to the present invention has a variable domain comprising human acceptor framework regions as well as one or more of the CDRs provided specifically herein. Thus, provided in one embodiment is blocking humanised antibody which binds human FcRn wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at http://www.imgt.org/

In a humanised antibody of the present invention, the acceptor heavy and light chains do not necessarily need to be derived from the same antibody and may, if desired, comprise composite chains having framework regions derived from different chains.

One such suitable framework region for the heavy chain of the humanised antibody of the present invention is derived from the human sub-group VH3 sequence IGHV3-7 together with JH3 (SEQ ID NO: 46 and 47).

Accordingly, in one example there is provided a humanised antibody comprising the sequence given in SEQ ID NO: 1 for CDR-H1, the sequence given in SEQ ID NO: 2 for CDR-H2 and the sequence given in SEQ ID NO: 3 for CDRH3, wherein the heavy chain framework region is derived from the human subgroup VH3 sequence IGHV3-7 together with JH3.

The sequence of human JH3 is as follows: (DAFDV)WGQGTMVTVS (SEQ ID No: 69). The DAFDV (SEQ ID NO: 70) motif is part of CDR-H3 and is not part of framework 4 (Ravetch, J V. et al., 1981, Cell, 27, 583-591).

In one example the heavy chain variable domain of the antibody comprises the sequence given in SEQ ID NO: 25 or 59, such as 25.

A suitable framework region for the light chain of the humanised antibody of the present invention is derived from the human sub-group VK1 sequence IGKV1-27 sequence together with JK4 (SEQ ID NO: 44 and 45).

Accordingly, in one example there is provided a humanised antibody comprising the sequence given in SEQ ID NO: 4 for CDR-L1, the sequence given in SEQ ID NO: 5 or SEQ ID NO: 7 for CDR-L2 and the sequence given in SEQ ID NO: 6 for CDRL3, wherein the light chain framework region is derived from the human sub-group VK1 sequence IGKV1-27 together with JK4.

The JK4 sequence is as follows: (LT)FGGGTKVEIK (Seq ID No: 71). The LT motif is part of CDR-L3 and is not part of framework 4 (Hieter, P A., et al., 1982, J. Biol. Chem., 257, 1516-1522).

In one example the light chain variable domain of the antibody comprises the sequence given in SEQ ID NO: 16 or 51, such as 16.

In a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

Thus in one embodiment 1, 2, 3, 4, or 5 residues in the framework are replaced with an alternative amino acid residue.

Accordingly, in one example there is provided a humanised antibody, wherein at least the residues at each of positions 48 and 78 of the variable domain of the heavy chain (Kabat numbering) are donor residues, see for example the sequence given in SEQ ID NO: 25.

In one embodiment residue 48 of the heavy chain variable domain is replaced with an alternative amino acid, for example valine.

In one embodiment residue 78 of the heavy chain variable domain is replaced with an alternative amino acid, for example leucine.

In one embodiment residue 48 is valine and residue 78 is leucine in the humanised heavy chain variable region according to the present disclosure.

Accordingly, in one example there is provided a humanised antibody, wherein at least the residues at each of positions 70 and 71 of the variable domain of the light chain (Kabat numbering) are donor residues, see for example the sequence given in SEQ ID NO: 16.

In one embodiment residue 70 of the light chain variable domain is replaced with an alternative amino acid, for example aspartic acid.

In one embodiment residue 71 of the light chain variable domain is replaced with an alternative amino acid, for example phenylalanine.

In one embodiment residue 70 is aspartic acid and residue 71 is phenylalanine in the humanised light chain variable region according to the present disclosure.

In one embodiment the disclosure provides an antibody sequence which is 80% similar or identical to a sequence disclosed herein, for example 85%, 90%, 91%, 92%, 93%, 94%, 95% 96%, 97%, 98% or 99% over part or whole of the relevant sequence, for example a variable domain sequence, a CDR sequence or a variable domain sequence, excluding the CDRs. In one embodiment the relevant sequence is SEQ ID NO: 16 or 51. In one embodiment the relevant sequence is SEQ ID NO: 25 or 59.

In one embodiment, the present invention provides an antibody molecule which binds human FcRn comprising a heavy chain, wherein the variable domain of the heavy chain comprises a sequence having at least 80%, 85%, 90%, 91%, 92%, 93%, 94%, 95% 96%, 97%, 98% or 99% identity or similarity to a sequence herein, for example the sequence given in SEQ ID NO: 25 or 59, such as 25.

In one embodiment, the present invention provides an antibody molecule which binds human FcRn comprising a light chain, wherein the variable domain of the light chain comprises a sequence having at least 80%, 85%, 90%, 91%, 92%, 93%, 94%, 95% 96%, 97%, 98% or 99% identity or similarity to the sequence given in SEQ ID NO: 16 or 51, such as 16.

In one embodiment the present invention provides an antibody molecule which binds human FcRn wherein the antibody has a heavy chain variable domain which is at least 90%, 91%, 92%, 93%, 94%, 95% 96%, 97%, 98% or 99% similar or identical to a sequence given herein, for example the sequence given in SEQ ID NO: 25 but wherein the antibody molecule has the sequence given in SEQ ID NO: 1 for CDR-H1, the sequence given in SEQ ID NO: 2 for CDR-H2 and the sequence given in SEQ ID NO: 3 for CDR-H3.

In one embodiment the present invention provides an antibody molecule which binds human FcRn wherein the antibody has a light chain variable domain which is at least 90%, 91%, 92%, 93%, 94%, 95% 96%, 97%, 98% or 99% similar or identical to a sequence given herein, for example the sequence in SEQ ID NO: 16 but wherein the antibody molecule has the sequence given in SEQ ID NO: 4 for CDR-L1, the sequence given in SEQ ID NO: 5 or SEQ ID NO: 7 for CDR-L2 and the sequence given in SEQ ID NO: 6 for CDR-L3.

In one embodiment the present invention provides an antibody molecule which binds human FcRn wherein the antibody has a heavy chain variable domain which is at least 90%, 91%, 92%, 93%, 94%, 95% 96%, 97%, 98% or 99% similar or identical to a sequence given herein, for example the sequence given in SEQ ID NO: 25 and a light chain variable domain which is at least 90%, 91%, 92%, 93%, 94%, 95% 96%, 97%, 98% or 99% similar or identical to a sequence given herein, for example the sequence given in SEQ ID NO: 16 but wherein the antibody molecule has the sequence given in SEQ ID NO: 1 for CDR-H1, the sequence given in SEQ ID NO: 2 for CDR-H2, the sequence given in SEQ ID NO: 3 for CDR-H3, the sequence given in SEQ ID NO: 4 for CDR-L1, the sequence given in SEQ ID NO: 5 or SEQ ID NO: 7 for CDR-L2 and the sequence given in SEQ ID NO: 6 for CDR-L3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

The antibody molecules of the present invention may comprise a complete antibody molecule having full length heavy and light chains or a fragment thereof and may be, but are not limited to Fab, modified Fab, Fab', modified Fab', F(ab')$_2$, Fv, single domain antibodies (e.g. VH or VL or VHH), scFv, dsscFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

In one embodiment the antibody molecule of the present disclosure is an antibody Fab fragment comprising the variable regions shown in SEQ ID NOs: 16 and 25, for example for the light and heavy chain respectively. In one embodiment the antibody molecule has a light chain comprising the sequence given in SEQ ID NO: 20 and a heavy chain comprising the sequence given in SEQ ID NO: 29.

In one embodiment the antibody molecule of the present disclosure is an antibody Fab fragment comprising the variable regions shown in SEQ ID NOs: 51 and 59, for example for the light and heavy chain respectively.

In one embodiment the antibody molecule of the present disclosure is an antibody Fab or Fab' fragment comprising the variable regions shown in SEQ ID NOs: 16 and 25, for example for the light and heavy chain respectively. In one embodiment the antibody molecule has a light chain comprising the sequence given in SEQ ID NO: 20 and a heavy chain comprising the sequence given in SEQ ID NO: 29 (Fab) or SEQ ID NO: 33 (Fab').

In one embodiment the antibody molecule of the present disclosure is an antibody Fab' fragment comprising the variable regions shown in SEQ ID NOs: 51 and 59, for example for the light and heavy chain respectively. In one embodiment the antibody molecule has a light chain comprising the sequence given in SEQ ID NO: 55 and a heavy chain comprising the sequence given in SEQ ID NO: 63.

In one embodiment the antibody molecule of the present disclosure is a full length IgG1 antibody comprising the variable regions shown in SEQ ID NOs: 16 and 25, for example for the light and heavy chain respectively. In one embodiment the antibody molecule has a light chain comprising the sequence given in SEQ ID NO: 20 and a heavy chain comprising the sequence given in SEQ ID NO: 73.

In one embodiment the antibody molecule of the present disclosure is a full length IgG1 comprising the variable regions shown in SEQ ID NOs: 51 and 59.

In one embodiment the antibody molecule of the present disclosure is a full length IgG4 format comprising the variable regions shown in SEQ ID NOs: 16 and 25, for example for the light and heavy chain respectively. In one embodiment the antibody molecule has a light chain comprising the sequence given in SEQ ID NO: 20 and a heavy chain comprising the variable region sequence given in SEQ ID NO: 25.

In one embodiment the antibody molecule of the present disclosure is a full length IgG4 format comprising the variable regions shown in SEQ ID NOs: 51 and 59, for example for the light and heavy chain respectively. In one embodiment the antibody molecule has a light chain comprising the sequence given in SEQ ID NO: 55 and a heavy chain comprising the variable region sequence given in SEQ ID NO: 59.

In one embodiment the antibody molecule of the present disclosure is a full length IgG4P format comprising the variable regions shown in SEQ ID NOs: 16 and 25, for example for the light and heavy chain respectively. In one embodiment the antibody molecule has a light chain comprising the sequence given in SEQ ID NO: 20 and a heavy chain comprising the sequence given in SEQ ID NO: 37 or SEQ ID NO: 39.

In one embodiment the antibody molecule of the present disclosure is a full length IgG4P format comprising the variable regions shown in SEQ ID NOs: 51 and 59, for example for the light and heavy chain respectively. In one embodiment the antibody molecule has a light chain comprising the sequence given in SEQ ID NO: 55 and a heavy chain comprising the variable region sequence given in SEQ ID NO: 59.

IgG4P as employed herein is a mutation of the wild-type IgG4 isotype where amino acid 241 is replaced by proline, see for example where serine at position 241 has been changed to proline as described in Angal et al., Molecular Immunology, 1993, 30 (1), 105-108.

In one embodiment the antibody according to the present disclosure is provided as an FcRn binding antibody fusion protein which comprises an immunoglobulin moiety, for example a Fab or Fab' fragment, and one or two single domain antibodies (dAb) linked directly or indirectly thereto, for example as described in WO2009/040562, WO2010035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site. In one such embodiment the heavy chain comprises the sequence given in SEQ ID NO: 42 and the light chain comprises the sequence given in SEQ ID NO: 40.

In one embodiment the Fab or Fab' according to the present disclosure is conjugated to a PEG molecule or human serum albumin.

CA170_01638g49 and 1638.g49 are employed inchangeably herein and are used to refer to a specific pair of antibody variable regions which may be used in a number of different formats. These variable regions are the heavy chain sequence given in SEQ ID NO: 25 and the light chain sequence given in SEQ ID NO: 16.

CA170_01638g28 and 1638.g28 are employed inchangeably herein and are used to refer to a specific pair of antibody variable regions which may be used in a number of different formats. These variable regions are the heavy chain sequence given in SEQ ID NO: 59 and the light chain sequence given in SEQ ID NO: 51.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment the antibody heavy chain comprises a CH1 domain and the antibody light chain comprises a CL domain, either kappa or lambda.

In one embodiment the light chain has the sequence given in SEQ ID NO: 20 and the heavy chain has the sequence given in SEQ ID NO: 29.

In one embodiment the light chain has the sequence given in SEQ ID NO: 20 and the heavy chain has the sequence given in SEQ ID NO: 33.

In one embodiment the light chain has the sequence given in SEQ ID NO: 20 and the heavy chain has the sequence given in SEQ ID NO: 37.

In one embodiment the light chain has the sequence given in SEQ ID NO: 20 and the heavy chain has the sequence given in SEQ ID NO: 74.

In one embodiment a C-terminal amino acid from the antibody molecule is cleaved during post-translation modifications.

In one embodiment an N-terminal amino acid from the antibody molecule is cleaved during post-translation modifications.

Also provided by the present invention is a specific region or epitope of human FcRn which is bound by an antibody provided by the present invention, in particular an antibody comprising the heavy chain sequence gH33 (SEQ ID NO: 25) and/or the light chain sequence gL7 (SEQ ID NO: 16 or an antibody comprising the heavy chain sequence gH2 (SEQ ID NO: 59) and the light chain sequence gL2 (SEQ ID NO: 51).

This specific region or epitope of the human FcRn polypeptide can be identified by any suitable epitope mapping method known in the art in combination with any one of the antibodies provided by the present invention. Examples of such methods include screening peptides of varying lengths derived from FcRn for binding to the antibody of the present invention with the smallest fragment that can specifically bind to the antibody containing the sequence of the epitope recognised by the antibody. The FcRn peptides may be produced synthetically or by proteolytic digestion of the FcRn polypeptide. Peptides that bind the antibody can be identified by, for example, mass spectrometric analysis. In another example, NMR spectroscopy or X-ray crystallography can be used to identify the epitope bound by an antibody of the present invention. In one example where X-ray crystallography is used, the epitope is determined as those residues on the FcRn polypeptide which are within 4 Å of the antibody. In one example the epitope is determined as those residues on the FcRn polypeptide which are within 5 Å of the antibody. Once identified, the epitopic fragment which binds an antibody of the present invention can be used, if required, as an immunogen to obtain additional antibodies which bind the same epitope.

In one embodiment the antibody of the present disclosure binds the human FcRn alpha chain extracellular sequence as shown below:

```
                                                    (SEQ ID NO: 48)
AESHLSLLYHLTAVSSPAPG TPAFWVSGWL GPQQYLSYNS

LRGEAEPCGA WVWENQVSWY WEKETTDLRI KEKLFLEAFK

A*LGGKGP*YTL QGLLGCELGPDNTSVPTAKFA*L*NGEEFMNFD

LKQGTWGG*D***WPEALAI*SQR WQQQDKAANK ELTFLLFSCP

HRLREHLERG RGNLEWKEPPSMRLKARPSSPGFSVLTCSA

FSFYPPELQL RFLRNGLAAG TGQGDFGPNSDGSFHASSSLT

VKSGDEHHYCCIVQHAGLAQPLRVELESPAKSS.
```

The residues underlined are those known to be critical for the interaction of human FcRn with the Fc region of human IgG. Those in bold are residues of the human FcRn polypeptide involved in binding the antibody comprising the heavy chain sequence given in SEQ ID NO: 25 and the light chain sequence given in SEQ ID NO: 16, ie they are within 4 Å of the antibody as determined by X-ray crystallography. Residues in italic are those involved in binding the same antibody at 5 Å.

In one aspect of the invention there is provided an anti-FcRn antibody or binding fragment thereof which binds an epitope of human FcRn which comprises one, two, three, or four amino acids selected from the group consisting of residues E115, W131, P132, and E133 of human FcRn extracellular domain (SEQ ID NO: 48), and wherein the anti-FcRn antibody or binding fragment thereof further binds one or more residues, such as two, three, four, five, six, seven, eight, nine or ten residues selected from the group consisting of A81, G83, G84, K85, G86, P87, N113, L135, A136, and Q139 and optionally further binds one or more residues selected from the group consisting of L82, Y88, L112 and D130.

Accordingly in one example there is provided an anti-FcRn antibody or binding fragment thereof which binds an epitope of human FcRn which comprises one, two, three, or four amino acids selected from the group consisting of residues E115, W131, P132, and E133 and at least one residue, for example at least 2, 3, 4, 5, 6, 7, 8, 9, 10 residues selected from the group consisting of A81, G83, G84, K85, G86, P87, N113, L135, A136, and Q139 and wherein said anti-FcRn antibody or binding fragment thereof optionally further binds one or more residues, for example at least 2, 3 or 4 residues selected from the group consisting of L82, Y88, L112 and D130 of human FcRn extracellular domain (SEQ ID NO: 48).

In one example an antibody according to this aspect of the invention does not bind V105, P106, T107, A108 and K109 of human FcRn extracellular domain (SEQ ID NO: 48).

In one example an antibody according to this aspect of the invention does not bind E116, F117, M118, N119, F120, D121, L122, K123, Q124, G128 and G129 of human FcRn extracellular domain (SEQ ID NO: 48).

In one example an antibody according to this aspect of the invention does not bind V105, P106, T107, A108, K109, E116, F117, M118, N119, F120, D121, L122, K123, Q124, G128, and G129 of human FcRn extracellular domain (SEQ ID NO: 48).

In one example there is provided an anti-FcRn antibody or binding fragment thereof which binds an epitope of human FcRn which comprises one, two, three, or four amino acids selected from the group consisting of residues E115, W131, P132, and E133 and at least one residue, for example at least 2, 3, 4, 5, 6, 7 or 8 residues selected from the group consisting of A81, L82, G83, G84, K85, G86, P87 and Y88 of human FcRn extracellular domain (SEQ ID NO: 48)

In one example there is provided an anti-FcRn antibody or binding fragment thereof which binds an epitope of human FcRn which comprises one, two, three, or four amino acids selected from the group consisting of residues E115, W131, P132, and E133 and at least one residue, for example at least 2, 3, 4, 5 or 6 residues selected from the group consisting of L112, N113, D130, L135, A136, and Q139 of human FcRn extracellular domain (SEQ ID NO: 48)

In one example there is provided an anti-FcRn antibody or binding fragment thereof which binds an epitope of human FcRn which comprises one, two, three, or four amino acids selected from the group consisting of residues E115, W131, P132, and E133 and at least one residue selected from the group consisting of A81, L82, G83, G84, K85, G86, P87, Y88, L112, N113, D130, L135, A136, and Q139 of human FcRn extracellular domain (SEQ ID NO: 48).

In one example there is provided an anti-FcRn antibody or binding fragment thereof which binds an epitope of human FcRn which comprises residues E115, W131, P132, and E133 and at least one residue selected from the group consisting of A81, L82, G83, G84, K85, G86, P87, Y88, L112, N113, D130, L135, A136, and Q139 of human FcRn extracellular domain (SEQ ID NO: 48).

In one example the present invention provides an anti-FcRn antibody or binding fragment thereof which binds an epitope of human FcRn which comprises or consists of residues A81, G83, G84, K85, G86, P87, N113, E115, W131, P132, E133, L135, A136, and Q139 of human FcRn extracellular domain (SEQ ID NO: 48).

In one example the present invention provides an anti-FcRn antibody or binding fragment thereof which binds an epitope of human FcRn which comprises or consists of residues A81, L82, G83, G84, K85, G86, P87, Y88, L112, N113, E115, D130, W131, P132, E133, L135, A136, and Q139 of human FcRn extracellular domain (SEQ ID NO: 48).

In one embodiment the antibodies which bind the epitope described herein above provided by the present invention are fully human. In one embodiment they are humanised. In one example they have an affinity for human FcRn of 150 pM or less, typically 130 pM or less.

Antibodies which cross-block the binding of an antibody molecule according to the present invention in particular, an antibody molecule comprising the heavy chain sequence given in SEQ ID NO: 25 and the light chain sequence given in SEQ ID NO: 16 may be similarly useful in blocking FcRn activity. Accordingly, the present invention also provides an anti-FcRn antibody molecule, which cross-blocks the binding of any one of the antibody molecules described herein above to human FcRn and/or is cross-blocked from binding human FcRn by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above.

Cross-blocking antibodies can be identified using any suitable method in the art, for example by using competition ELISA or BIAcore assays where binding of the cross blocking antibody to human FcRn prevents the binding of an antibody of the present invention or vice versa. Such cross blocking assays may use isolated natural or recombinant FcRn or a suitable fusion protein/polypeptide. In one example binding and cross-blocking is measured using recombinant human FcRn extracellular domain (SEQ ID NO: 48). In one example the recombinant human FcRn alpha chain extracellular domain is used in a complex with β2 microglobulin (β2M) (SEQ ID NO:72).

In one embodiment there is provided an anti-FcRn antibody molecule which blocks FcRn binding to IgG and which cross-blocks the binding of an antibody whose heavy chain comprises the sequence given in SEQ ID NO: 25 and whose light chain comprises the sequence given in SEQ ID NO: 16 to human FcRn. In one embodiment the cross-blocking antibodies provided by the present invention inhibit the binding of an antibody comprising the heavy chain sequence given in SEQ ID NO: 25 and the light chain sequence given in SEQ ID NO: 16 by greater than 80%, for example by greater than 85%, such as by greater than 90%, in particular by greater than 95% inhibition.

In one embodiment the cross-blocking antibodies provided by the present invention are fully human. In one embodiment the cross-blocking antibodies provided by the present invention are humanised. In one embodiment the cross-blocking antibodies provided by the present invention have an affinity for human FcRn of 150 pM or less, 130 pM or less or 100 pM or less. In one embodiment the cross-blocking antibodies provided by the present invention have an affinity for human FcRn of 50 pM or less. Affinity can be measured using the methods described herein below.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the FcRn antibody and fragments of the invention may be engineered to have an appropriate isoelectric point. This may lead to antibodies and/or fragments with more robust properties, in particular suitable solubility and/or stability profiles and/or improved purification characteristics.

Thus in one aspect the invention provides a humanised FcRn antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as **ExPASY http://www.expasy.ch/tools/pi_tool.html, and http://www.iut-arles.up.univ-mrs.fr/w3bb/d_abim/compo-p.html, may be used to predict the isoelectric point of the antibody or fragment. Alternatively or additionally, the pI can be measured using any suitable standard laboratory technique.

The antibody molecules of the present invention suitably have a high binding affinity, in particular in the nanomolar range. Affinity may be measured using any suitable method known in the art, including BIAcore, as described in the Examples herein, using isolated natural or recombinant FcRn or a suitable fusion protein/polypeptide. In one example affinity is measured using recombinant human FcRn extracellular domain as described in the Examples herein (SEQ ID NO: 48). In one example affinity is measured using the recombinant human FcRn alpha chain extracellular domain (SEQ ID NO: 48) in association with human β2 microglobulin (β2M) (SEQ ID NO: 72). Suitably the antibody molecules of the present invention have a binding affinity for isolated human FcRn of about 1 nM or lower. In one embodiment the antibody molecule of the present invention has a binding affinity of about 500 pM or lower (i.e. higher affinity). In one embodiment the antibody molecule of the present invention has a binding affinity of about 250 pM or lower. In one embodiment the antibody molecule of the present invention has a binding affinity of about 200 pM or lower. In one embodiment the antibody molecule of the present invention has a binding affinity of about 150 pM or lower. In one embodiment the present invention provides an anti-FcRn antibody with a binding affinity of about 100 pM or lower. In one embodiment the present invention provides a humanised anti-FcRn antibody with a binding affinity of about 100 pM or lower. In one embodiment the present invention provides an anti-FcRn antibody with a binding affinity of 50 pM or lower.

In one embodiment the antibodies of the present invention are able to bind human FcRn at both pH6 or lower pH (in particular pH 6) and pH7.4 or higher pH (in particular pH7.4) with comparable binding affinity. Advantageously therefore the antibodies are able to continue to bind FcRn even within the endosome, thereby maximising the blocking of FcRn binding to IgG.

In one embodiment the antibodies of the present invention are able to bind human FcRn with a binding affinity of 150 pM or lower when measured at pH6 and pH7.4. In one embodiment the antibodies of the present invention are able to bind human FcRn with a binding affinity of 130 pM or lower when measured at pH6 and pH7.4. In one embodiment the antibodies of the present invention are able to bind human FcRn with a binding affinity of 130 pM or lower when measured at pH6 and a binding affinity of 50 pM or lower when measured at pH7.4.

The affinity of an antibody or binding fragment of the present invention, as well as the extent to which a binding agent (such as an antibody) inhibits binding, can be determined by one of ordinary skill in the art using conventional techniques, for example those described by Scatchard et al. (Ann. K Y. Acad. Sci. 51:660-672 (1949)) or by surface plasmon resonance (SPR) using systems such as BIAcore. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In the present invention affinity of the test antibody molecule is typically determined using SPR as follows. The test antibody molecule is captured on the solid phase and human FcRn alpha chain extracellular domain in non-covalent complex with human β2M is run over the captured antibody in the mobile phase and affinity of the test antibody molecule for human FcRn determined. The test antibody molecule may be captured on the solid phase chip surface using any appropriate method, for example using an anti-Fc or anti Fab' specific capture agent. In one example the affinity is determined at pH6. In one example the affinity is determined at pH7.4.

It will be appreciated that the affinity of antibodies provided by the present invention may be altered using any suitable method known in the art. The present invention therefore also relates to variants of the antibody molecules of the present invention, which have an improved affinity for FcRn. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention block human FcRn activity. Assays suitable for determining the ability of an antibody to block FcRn are described in the Examples herein. A suitable assay for determining the ability of an antibody molecule to block IgG recycling in vitro is described herein below.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

In one embodiment a half-life provided by an effector molecule which is independent of FcRn is advantageous.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido)propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

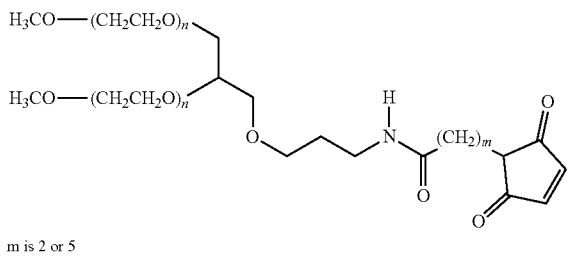

m is 2 or 5

That is to say each PEG is about 20,000 Da.

Thus in one embodiment the PEG is 2,3-Bis(methylpolyoxyethylene-oxy)-1-{[3-(6-maleimido-1-oxohexyl)

amino]propyloxy} hexane (the 2 arm branched PEG, —CH$_2$)$_3$NHCO(CH$_2$)$_5$-MAL, Mw 40,000 known as SUN-BRIGHT GL2-400MA3.

Further alternative PEG effector molecules of the following type:

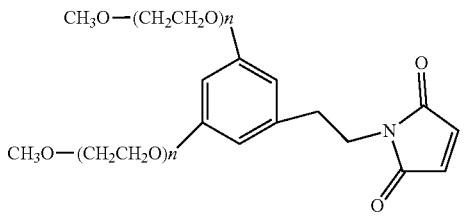

are available from Dr Reddy, NOF and Jenkem.

In one embodiment there is provided an antibody which is PEGylated (for example with a PEG described herein), attached through a cysteine amino acid residue at or about amino acid 232 in the chain, for example amino acid 232 of the heavy chain (by sequential numbering), for example amino acid 232 of SEQ ID NO: 33.

In one embodiment the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one example the present invention provides a method treating a disease ameliorated by blocking human FcRn comprising administering a therapeutically effective amount of an anti-FcRn antibody or binding fragment thereof wherein the antibody or binding fragment thereof has a half life that is independent of Fc binding to FcRn.

In one embodiment there is provided a Fab' conjugated to a polymer, such as a PEG molecule, a starch molecule or an albumin molecule.

In one embodiment there is provided a scFv conjugated to a polymer, such as a PEG molecule, a starch molecule or an albumin molecule.

In one embodiment the antibody or fragment is conjugated to a starch molecule, for example to increase the half life. Methods of conjugating starch to a protein as described in U.S. Pat. No. 8,017,739 incorporated herein by reference.

In one embodiment there is provided an anti-FcRn binding molecule (i.e an antibody or binding fragment thereof) which:

Causes 50-85% reduction, such as a 70% reduction of plasma IgG concentration,

With not more than 25% or 20% reduction of plasma albumin concentration, and/or

With the possibility of repeat dosing to achieve long-term maintenance of low plasma IgG concentration.

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in herein.

Examples of suitable DNA sequences encoding the 1638.g49 light chain variable region are provided in SEQ ID NO: 17, SEQ ID NO: 19 and SEQ ID NO: 21.

Examples of suitable DNA sequences encoding the 1638.g28 light chain variable region are provided in SEQ ID NO: 52 and SEQ ID NO: 54.

Examples of suitable DNA sequences encoding the 1638.g49 heavy chain variable region are provided in SEQ ID NO: 26 and SEQ ID NO: 28.

Examples of suitable DNA sequences encoding the 1638.g28 heavy chain variable region are provided in SEQ ID NO: 60 and 62.

Examples of suitable DNA sequences encoding the 1638.g49 light chain (variable and constant) are provided in SEQ ID NO: 21, SEQ ID NO: 22 and SEQ ID NO: 24, and for 1638.g28 light chain the sequence given in SEQ ID NO: 54, SEQ ID NO: 56, SEQ ID NO:58 and 1638.g28 heavy chain the sequence given in SEQ ID NO: 64 or SEQ ID NO: 66.

Examples of suitable DNA sequences encoding the 1638.g49 heavy chain (variable and constant, depending on format) are provided in SEQ ID NO: 30 (Fab), SEQ ID NO: 34 or 36 (Fab'), SEQ ID NO: 38 (IgG4P), SEQ ID NO: 43 (FabFv) and SEQ ID NO:74 (IgG1).

Accordingly in one example the present invention provides an isolated DNA sequence encoding the heavy chain of an antibody Fab or Fab' fragment of the present invention which comprises the sequence given in SEQ ID NO: 30, 32, 34, 36, 64 or 66. Also provided is an isolated DNA sequence encoding the light chain of an antibody Fab or Fab' fragment of the present invention which comprises the sequence given in SEQ ID NO: 21, 22 or 56.

In one example the present invention provides an isolated DNA sequence encoding the heavy chain and the light chain of an IgG4(P) antibody of the present invention in which the DNA encoding the heavy chain comprises the sequence given in SEQ ID NO: 38 and the DNA encoding the light chain comprises the sequence given in SEQ ID NO: 22.

In one example the present invention provides an isolated DNA sequence encoding the heavy chain and the light chain of an IgG1 antibody of the present invention in which the DNA encoding the heavy chain comprises the sequence given in SEQ ID NO: 74 and the DNA encoding the light chain comprises the sequence given in SEQ ID NO: 22.

In one example the present invention provides an isolated DNA sequence encoding the heavy chain and the light chain of a Fab-dsFv antibody of the present invention in which the DNA encoding the heavy chain comprises the sequence given in SEQ ID NO: 43 and the DNA encoding the light chain comprises the sequence given in SEQ ID NO: 41.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention.

Accordingly the present invention also provides a host cell for expression of an antibody according to the invention comprising:

i) a DNA sequence encoding the heavy chain of said antibody, and ii) a DNA sequence encoding the light chain of said antibody wherein the DNA sequences are provided in one or more cloning or expression vectors.

Any suitable host cell/vector system may be used for expression of the DNA sequences encoding the antibody molecule of the present invention. Bacterial, for example *E. coli*, and other microbial systems may be used (especially for expressing antibody fragments or eukaryotic, for example mammalian, host cell expression systems may also be used (especially for expressing full-length antibodies). Suitable mammalian host cells include CHO, myeloma or hybridoma cells.

Suitable types of Chinese Hamster Ovary (CHO cells) for use in the present invention may include CHO and CHO-K1 cells including dhfr-CHO cells, such as CHO-DG44 cells and CHO-DXB11 cells, which may be used with a DHFR selectable marker or CHOK1-SV cells which may be used with a glutamine synthetase selectable marker. Other cell types of use in expressing antibodies include lymphocytic cell lines, e.g., NS0 myeloma cells and SP2 cells, COS cells.

The present invention also provides a process for the production of an antibody molecule according to the present invention comprising culturing a host cell containing a vector or vectors of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are conducive to commercial processing.

Thus there is a provided a process for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

In one embodiment there is provided a process for purifying an antibody (in particular an antibody or fragment according to the invention) comprising the steps: performing anion exchange chromatography in non-binding mode such that the impurities are retained on the column and the antibody is eluted.

In one embodiment the purification employs affinity capture on an FcRn column.

In one embodiment the purification employs cibacron blue or similar for purification of albumin fusion or conjugate molecules.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filtration steps, such as a diafiltration step.

Thus in one embodiment there is provided a purified anti-FcRn antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

The antibody molecules of the present invention may also be used in diagnosis, for example in the in vivo diagnosis and imaging of disease states involving FcRn.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody molecule of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable excipient.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients or non-antibody ingredients such as steroids or other drug molecules, in particular drug molecules whose half-life is independent of FcRn binding.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg.

Pharmaceutical compositions may be conveniently presented in unit dose forms containing a predetermined amount of an active agent of the invention per dose.

Therapeutic doses of the antibodies according to the present disclosure show no apparent toxicology effects in vivo.

In one embodiment of an antibody or fragment according to the invention a single dose may provide up to a 70% reduction in circulating IgG levels. In one example of an antibody or fragment according to the invention a single dose may provide up to a 80% reduction in circulating IgG levels. In one example of an antibody or fragment according to the invention a single dose may provide a greater than 80% reduction in circulating IgG levels.

The maximal therapeutic reduction in circulating IgG may be observed about 1 week after administration of the relevant therapeutic dose. The levels of IgG may recover over the weeks following dosing if further therapeutic doses are not delivered. Recover as employed herein refers to levels returning to levels similar to those observed before initial dosing commenced.

Advantageously, the levels of IgG in vivo may be maintained at an appropriately low level by administration of sequential doses of the antibody or fragments according to the disclosure.

Compositions may be administered individually to a patient or may be administered in combination (e.g. simultaneously, sequentially or separately) with other agents, drugs or hormones.

Agents as employed herein refers to an entity which when administered has a physiological affect.

Drug as employed herein refers to a chemical entity which at a therapeutic dose has an appropriate physiological affect.

In one embodiment the antibodies or fragments according to the present disclosure are employed with an immunosuppressant therapy, such as a steroid, in particular prednisone.

In one embodiment the antibodies or fragments according to the present disclosure are employed with Rituximab or other B cell therapies.

In one embodiment the antibodies or fragments according to the present disclosure are employed with any B cell or T cell modulating agent or immunomodulator. Examples include methotrexate, microphenyolate and azathioprine.

The dose at which the antibody molecule of the present invention is administered depends on the nature of the condition to be treated, the extent of the inflammation present and on whether the antibody molecule is being used prophylactically or to treat an existing condition.

The frequency of dosing will depend on the half life of the antibody, its target-mediated disposition, the duration of its effect, and the presence of anti-drug antibodies. If the antibody has a short half life (a few hours) or a limited activity, and/or if it is desirable to deliver small volumes of drug (e.g. for subcutaneous injection), it may be necessary to dose frequently, as frequently as once or more per day. Alternatively, if the antibody has a long half life, has long duration of activity, or can be dosed in large volumes (such as by infusion) dosing may be infrequent, once per day, or every few days, weeks or months. In one embodiment, sufficient time is allowed between doses to allow anti-drug antibody levels to decline.

Half life as employed herein is intended to refer to the duration of the molecule in circulation, for example in serum/plasma.

Pharmacodynamics as employed herein refers to the profile and in particular duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pI of the protein is in the range 8-9 or above then a formulation pH of 7 may be appropriate. Whilst not wishing to be bound by theory it is thought that this may ultimately provide a final formulation with improved stability, for example the antibody or fragment remains in solution.

In one example the pharmaceutical formulation at a pH in the range of 4.0 to 7.0 comprises: 1 to 200 mg/mL of an antibody molecule according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 1 to 5 µm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Examples of buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solutionbuffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule (or compositions comprising same) for use in the control of autoimmune diseases, for example Acute Disseminated Encephalomyelitis (ADEM), Acute necrotizing hemorrhagic leukoencephalitis, Addison's disease, Agammaglobulinemia, Alopecia areata, Amyloidosis, ANCA-associated vasculitis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticarial, Axonal & nal neuropathies, Balo disease, Behcet's disease, Bullous pemphigoid, Cardiomyopathy, Castleman disease, Celiac disease, Chagas disease, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Dilated cardiomyopathy, Discoid lupus, Dressler's syndrome, Endometriosis, Eosinophilic angiocentric fibrosis, Eosinophilic fasciitis, Erythema nodosum, Experimental allergic encephalomyelitis, Evans syndrome, Fibrosing alveolitis, Giant cell arteritis (temporal arteritis), Glomerulonephritis, Goodpasture's syndrome, Granulomatosis with Polyangiitis (GPA) see Wegener's, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic hypocomplementemic tubulointestitial nephritis, Idiopathic thrombocytopenic purpura (ITP), IgA nephropathy, IgG4-related disease, IgG4-related sclerosing disease, Immunoregulatory lipoproteins, Inflammatory aortic aneurysm, Inflammatory pseudotumour, Inclusion body myositis, Insulin-dependent diabetes (type1), Interstitial cystitis, Juvenile arthritis, Juvenile diabetes, Kawasaki syndrome, Kuttner's tumour, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Mediastinal fibrosis, Meniere's disease, Microscopic polyangiitis, Mikulicz's syndrome, Mixed connective tissue disease (MCTD), Mooren's ulcer, Mucha-Habermann disease, Multifocal fibrosclerosis, Multiple sclerosis, Myasthenia gravis, Myositis, Narcolepsy, Neuromyelitis optica (Devic's), Neutropenia, Ocular cicatricial pemphigoid, Optic neuritis, Ormond's disease (retroperitoneal fibrosis), Palindromic rheumatism, PANDAS (Pediatric Autoimmune Neuropsychiatric Disorders Associated with *Streptococcus*), Paraneoplastic cerebellar degeneration, Paraproteinemic polyneuropathies, Paroxysmal nocturnal hemoglobinuria (PNH), Parry Romberg syndrome, Parsonnage-Turner syndrome, Pars planitis (peripheral uveitis), Pemphigus vulgaris, Peri-aortitis, Periarteritis, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis (Ormond's disease), Rheumatic fever, Rheumatoid arthritis, Riedel's thyroiditis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombotic, thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, Waldenstrom Macroglobulinaemia, Warm idiopathic haemolytic anaemia and Wegener's granulomatosis (now termed Granulomatosis with Polyangiitis (GPA).

Additional indications may also include hyperviscosity syndromes; cryoglobulinemia; recurrent focal and segmental glomerulosclerosis in the transplanted kidney; HELLP syndrome; Refsum disease; HIV-related neuropathy; rhabdomyolysis and alloimune diseases.

In one embodiment the antibodies or fragments according to the disclosure are employed in the treatment or prophylaxis of epilepsy or seizures.

In one embodiment the antibodies or fragments according to the disclosure are employed in the treatment or prophylaxis of multiple sclerosis.

In embodiment the antibodies and fragments of the disclosure are employed in alloimmune disease/indications which includes:
Transplantation donor mismatch due to anti-HLA antibodies
Foetal and neonatal alloimmune thrombocytopenia, FNAIT (or neonatal alloimmune thrombocytopenia, NAITP or NAIT or NAT, or foeto-maternal alloimmune thrombocytopenia, FMAITP or FMAIT).

Additional indications include: rapid clearance of Fc-containing biopharmaceutical drugs from human patients and combination of anti-FcRn therapy with other therapies—IVIg, Rituxan, plasmapheresis. For example anti-FcRn therapy may be employed following Rituxan therapy.

In addition anti-FcRn therapy may be used to rapidly clear imaging agents such as radiolabelled antibodies used in imaging tumors.

In embodiment the antibodies and fragments of the disclosure are employed in a neurology disorder such as:
Chronic inflammatory demyelinating polyneuropathy (CIDP)
Guillain-Barre syndrome
Paraproteinemic polyneuropathies
Neuromyelitis optica (NMO, NMO spectrum disorders or NMO spectrum diseases), and
Myasthenia gravis.

In embodiment the antibodies and fragments of the disclosure are employed in a dermatology disorder such as:
Bullous pemphigoid
Pemphigus vulgaris
ANCA-associated vasculitis
Dilated cardiomyopathy In embodiment the antibodies and fragments of the disclosure are employed in an Immunology, haematology disorder such as:
Idiopathic thrombocytopenic purpura (ITP)
Thrombotic thrombocytopenic purpura (TTP)
Warm idiopathic haemolytic anaemia
Goodpasture's syndrome
Transplantation donor mismatch due to anti-HLA antibodies In one embodiment the disorder is selected from Myasthenia Gravis, Neuro-myelitis Optica, CIDP, Guillaume-Barre Syndrome, Para-proteinemic Poly neuropathy, Refractory Epilepsy, ITP/TTP, Hemolytic Anemia, Goodpasture's Syndrome, ABO mismatch, Lupus nephritis, Renal Vasculitis, Sclero-derma, Fibrosing alveolitis, Dilated cardiomyopathy, Grave's Disease, Type 1 diabetes, Auto-immune diabetes, Pemphigus, Sclero-derma, Lupus, ANCA vasculitis, Dermato-myositis, Sjogren's Disease and Rheumatoid Arthritis.

In one embodiment the disorder is selected from autoimmune polyendocrine syndrome types 1 (APECED or Whitaker's Syndrome) and 2 (Schmidt's Syndrome); alopecia universalis; myasthenic crisis; thyroid crisis; thyroid associated eye disease; thyroid ophthalmopathy; autoimmune diabetes; autoantibody associated encephalitis and/or encephalopathy; pemphigus foliaceus; epidermolysis bullosa; dermatitis herpetiformis; Sydenham's chorea; acute motor axonal neuropathy (AMAN); Miller-Fisher syndrome; multifocal motor neuropathy (MMN); opsoclonus; inflammatory myopathy; Isaac's syndrome (autoimmune neuromyotonia), Paraneoplastic syndromes and Limbic encephalitis.

The antibodies and fragments according to the present disclosure may be employed in treatment or prophylaxis.

The present invention also provides a method of reducing the concentration of undesired antibodies in an individual comprising the steps of administering to an individual a therapeutically effective dose of an anti-FcRn antibody or binding fragment thereof described herein.

The present invention further provides the use of an antibody molecule according to the present invention in the manufacture of a medicament for the treatment and/or prophylaxis of a pathological disorder described herein such as an autoimmune disease.

In one embodiment the present disclosure comprises use of antibodies or fragments thereof as a reagent for diagnosis, for example conjugated to a reporter molecule. Thus there is provided antibody or fragment according to the disclosure which is labelled. In one aspect there is provided a column comprising an antibody or fragment according to the disclosure.

Thus there is provided an anti-FcRn antibody or binding fragment for use as a reagent for such uses as:
1) purification of FcRn protein (or fragments thereof)—being conjugated to a matrix and used as an affinity column, or (as a modified form of anti-FcRn) as a precipitating agent (e.g. as a form modified with a domain recognised by another molecule, which may be modified by addition of an Fc (or produced as full length IgG), which is optionally precipitated by an anti-Fc reagent)
2) detection and/or quantification of FcRn on cells or in cells, live or fixed (cells in vitro or in vivo in tissue or cell sections). Uses for this may include quantification of FcRn as a biomarker, to follow the effect of anti-FcRn treatment. For these purposes, the candidate might be used in a modified form (e.g. by addition of an Fc domain, as in full length IgG, or some other moiety, as a genetic fusion protein or chemical conjugate, such as addition of a fluorescent tag used for the purposes of detection).
3) purification or sorting of FcRn-bearing cells labeled by binding to candidate modified by ways exemplified in (1) and (2).

Also provided by the present invention is provided an assay suitable for assessing the ability of a test molecule such as an antibody molecule to block FcRn activity and in particular the ability of the cells to recycle IgG. Such an assay may be useful for identifying inhibitors of FcRn activity, such as antibody molecules or small molecules and as such may also be useful as a batch release assay in the production of such an inhibitor.

In one aspect there is provided an assay suitable for assessing the ability of a test molecule such as an antibody molecule to block human FcRn activity and in particular the ability of human FcRn to recycle IgG, wherein the method comprises the steps of:
a) coating onto a surface non-human mammalian cells recombinantly expressing human FcRn alpha chain and human β2 microglobulin (β2M),
b) contacting the cells under mildly acidic conditions such as about pH5.9 with a test molecule and an IgG to be recycled by the cell for a period of time sufficient to allow binding of both the test molecule and the IgG to FcRn, optionally adding the test molecule before the IgG to be recycled and incubating for a period of time sufficient to allow binding of the test molecule to FcRn.
c) washing with a slightly acidic buffer, and
d) detecting the amount of IgG internalised and/or recycled by the cells.

In one aspect there is provided an assay suitable for assessing the ability of a test molecule such as an antibody molecule to block human FcRn activity and in particular the ability of human FcRn to recycle IgG, wherein the method comprises the steps of:
a) coating onto a surface non-human mammalian cells recombinantly expressing human FcRn alpha chain and human β2 microglobulin (β2M),
b) contacting the cells under mildly acidic conditions such as about pH5.9 with a test antibody molecule and an IgG to be recycled by the cell for a period of time sufficient to allow binding of both the test antibody molecule and the IgG to FcRn, optionally adding the test antibody molecule before the IgG to be recycled and incubating for a period of time sufficient to allow binding of the test antibody molecule to FcRn.
c) washing with a slightly acidic buffer to remove unbound IgG and test antibody molecule, and
d) detecting the amount of IgG recycled by the cells.

In one aspect there is provided an assay suitable for assessing the ability of a test molecule such as an antibody molecule to block human FcRn activity and in particular the ability of human FcRn to recycle IgG, wherein the method comprises the steps of:
a) coating onto a surface non-human mammalian cells recombinantly expressing human FcRn alpha chain and human β2 microglobulin (β2M), b) contacting the cells under mildly acidic conditions such as about pH5.9 with a test antibody molecule and an IgG to be recycled by the cell for a period of time sufficient to allow binding of both the test antibody molecule and IgG to FcRn, optionally adding the test antibody molecule before the IgG to be recycled and incubating for a period of time sufficient to allow binding of the test antibody molecule to FcRn.

c) washing with a slightly acidic buffer to remove unbound IgG and test antibody molecule, d) incubating the cells in a neutral buffer such as about pH 7.2 e) detecting the amount of IgG recycled by the cells by determining the amount of IgG released into the supernatant.

Suitable cells include Madin-Darby Canine Kidney (MDCK) II cells. Transfection of MDCKII cells with human FcRn alpha chain and human β2 microglobulin (β2M) has previously been described by Claypool et al., 2002, Journal of Biological Chemistry, 277, 31, 28038-28050. This paper also describes recycling of IgG by these transfected cells.

Media for supporting the cells during testing includes complete media comprising MEM (Gibco #21090-022), 1× non-essential amino acids (Gibco 11140-035), 1× sodium pyruvate (Gibco #11360-039), and L-glutamine (Gibco #25030-024).

Acidic wash can be prepared by taking HBSS+(PAA #H15-008) and adding 1M MES until a pH 5.9+/−0.5 is reached. BSA about 1% may also be added (Sigma #A9647).

A neutral wash can be prepared by taking HBSS+(PAA #H15-008) and adding 10M Hepes pH 7.2+/−0.5 is reached. BSA about 1% may also be added (Sigma #A9647).

Washing the cells with acidic buffer removes the unbound test antibody and unbound IgG and allows further analysis to be performed. Acidic conditions used in step (b) encourage the binding of the IgG to FcRn and internalisation and recycling of the same.

The amount of test antibody or fragment and IgG on only the surface of the cells may be determined by washing the cells with neutral wash and analysing the supernatant/washings to detect the quantity of test antibody or IgG. Importantly a lysis buffer is not employed. To determine the amount of IgG internalised by the cells the antibody may first be removed from the surface of the cell with a neutral wash and the cells lysed by a lysis buffer and then the internal contents analysed. To determine the amount of IgG recycled by the cells the cells are incubated under neutral conditions for a suitable period of time and the surrounding buffer analysed for IgG content. If the surface and internal antibody content of the cell is required then the cell can be washed with acid wash to maintain the antibody presence on the cell surface, followed by cell lysis and analysis of the combined material.

Where it is desired to measure both internalisation and recycling of the IgG samples are run in duplicate and testing for internalisation and recycling conducted separately.

A suitable lysis buffer includes 150 mM NaCl, 20 mM Tris, pH 7.5, 1 mM EDTA, 1 mM EGTA, 1% Triton-X 100, for each 10 ml add protease inhibitors/phosphate inhibitors as described in manufacturer's guidelines.

Typically the IgG to be recycled is labelled, in one example a biotinylated human IgG may be used. The IgG can then be detected employing, for example a streptavidin sulfo-tag detection antibody (such as MSD #r32ad-5) 25 mL at 0.2 ug/mL of MSD blocking buffer. Blocking buffer may comprise 500 mM Tris, pH7.5. 1.5M NaCl and 0.2% Tween-20 and 1.5% BSA.

Alternatively the IgG may be pre-labelled with a fluorophore or similar label.

In one embodiment a suitable surface is a plastic plate or well such as a 96 well plate or similar, a glass slide or a membrane. In one example cells are coated onto the surface at a density that results in the formation of a monolayer.

In one embodiment the assay described herein is not a measurement of transcytosis of an antibody top to bottom across a membrane with a pH gradient there-across, for example acid conditions one side of the membrane and neutral conditions on the underside of the membrane.

In one example the test antibody or fragment and IgG may be incubated with the cells in step (b) for about 1 hour for example at ambient temperature under acidic conditions to allow binding.

In one example the test antibody or fragment may be incubated with the cells in step (b) for about 1 hour for example at ambient temperature under acidic conditions to allow binding before addition of the IgG to be recycled. Subsequently the IgG to be recycled by the cell may be incubated with the cells in step (b) for about 1 hour for example at ambient temperature under acidic conditions to allow binding.

Neutral conditions facilitate release of the IgG into the supernatant.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

The present invention is further described by way of illustration only in the following examples, which refer to the accompanying Figures, in which:

FIG. 1 Shows % hIgG in transgenic mice determined by LC-MS/MS

FIG. 1a shows the effect of 1638 IgG4P format on the concentration of human IVIg in serum of human FcRn-transgenic mice.

FIG. 1b shows the effect of 1638 FabFv and Fab'PEG formats on the concentration of human IVIg in human FcRn-transgenic mice FIG. 1c shows the pharmacokinetics of 1638 IgG4P format in human FcRn-transgenic mice.

FIG. 1d shows the pharmacokinetics of 1638 FabFv and Fab'PEG formats in human FcRn-transgenic mice FIG. 1e The effect of 1638 FabFv and Fab'PEG formats on the concentration of serum albumin in human FcRn-transgenic mice.

FIG. 1f The effect of 1638 IgG4P format on the concentration of serum albumin in human FcRn-transgenic mice.

FIG. 2 shows representative binding curves for CA170_1638.g49 IgG4. The mean $K_D$ values (n=3) were 0.20 nM in neutral buffer, & 0.22 nM in acidic buffer, respectively FIG. 3 shows CA170_1638.g49 IgG4 inhibits IgG recycling in MDCK II clone 15 cells FIG. 4 shows CA170_1638.g49 IgG4 inhibits IgG transcytosis in MDCK II clone 15 cells.

FIG. 5 shows CA170_1638.g49 FabFv inhibits IgG transcytosis in MDCK II clone 15 cells.

FIG. 6 shows representative binding curves for CA170_1638.g49 IgG4. The mean KD values (n=3) were 0.3 in neutral buffer, and 0.43 in acidic buffer, respectively (see Table 2).

FIG. 7 shows CA170_1638 CDR sequences

FIG. 8 Antibody sequences according to the present disclosure

FIG. 9a Humanisation of antibody 1638.g49

FIG. 9b Humanisation of antibody 1638.g49

EXAMPLES

Abbreviations
° C. temperature, degrees centigrade.
ATR FTIR Attenuated Total Reflectance Fourier Transform Infra-Red Spectroscopy
CH2 constant heavy chain region 2
cIEF capillary isoelectric focusing
DSC differential scanning calorimetry
GOF fucosylated aglactosyl biantennary glycan
H chain Heavy chain
HPLC high performance liquid chromatography
IgG immunoglobulin G
L chain Light chain
nLCMS nano-liquid chromatography mass spectrometry
PBS phosphate-buffered saline buffer
pI isoelectric point
SD standard deviation
SEC size exclusion chromatography
ToF time of flight
$T_m$ melting temperature
TCEP Tris(2-carboxyethyl)phosphine
THP Tris(hydroxypropyl)phosphine
Tris tris(hydroxymethyl)aminomethane The following immunizations were performed in order to generate material for B cell culture and antibody screening: Sprague Dawley rats were immunized with three shots of NIH3T3 mouse fibroblasts co-expressing mutant human FcRn (L320A; L321A) (Ober et al., 2001 Int. Immunol. 13, 1551-1559) and mouse β2M with a fourth final boost of human FcRn extracellular domain.

Sera were monitored for both binding to mutant FcRn on HEK-293 cells and for its ability to prevent binding of Alexafluor 488-labelled human IgG. Both methods were performed by flow cytometry. For binding, phycoerythrin (PE)-labelled anti mouse or rat Fc specific secondary reagents were used to reveal binding of IgG in sera.

B cell cultures were prepared using a method similar to that described by Zubler et al. (1985). Briefly, B cells at a density of approximately 5000 cells per well were cultured in bar-coded 96-well tissue culture plates with 200 μl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 2-5% activated rabbit splenocyte culture supernatant and gamma-irradiated EL-4-B5 murine thymoma cells ($5 \times 10^4$/well) for seven days at 37° C. in an atmosphere of 5% $CO_2$.

The presence of FcRn-specific antibodies in B cell culture supernatants was determined using a homogeneous fluorescence-based binding assay using HEK-293 cells transiently transfected with mutant FcRn (surface-stabilised) as a source of target antigen. 10 ul of supernatant was transferred from barcoded 96-well tissue culture plates into barcoded 384-well black-walled assay plates containing 5000 transfected HEK-293 cells per well using a Matrix Platemate liquid handler. Binding was revealed with a goat anti-rat or mouse IgG Fcγ-specific Cy-5 conjugate (Jackson). Plates were read on an Applied Biosystems 8200 cellular detection system. From 3800×96-well culture plates, representing 38 different immunized animals, 9800 anti-human FcRn binders were identified. It was estimated that this represented the screening of approximately 2.5 billion B cells.

Following primary screening, positive supernatants were consolidated on 96-well bar-coded master plates using an Aviso Onyx hit-picking robot and B cells in cell culture plates frozen at −80 C. Master plates were then screened in a Biacore assay in order to identify wells containing antibodies of high affinity and those which inhibited the binding of human IgG to FcRn (see below).

Biomolecular interaction analysis using surface plasmon resonance technology (SPR) was performed on a BIAcore T200 system (GE Healthcare). Goat anti-rat IgG, Fc gamma (Chemicon International Inc.) in 10 mM NaAc, pH 5 buffer was immobilized on a CM5 Sensor Chip via amine coupling chemistry to a capture level of approx. 19500 response units (RU) using HBS-EP+ as the running buffer. 50 mM Phosphate, pH6+150 mM NaCl was used as the running buffer for the affinity and blocking assay. B cell culture supernatants were diluted 1 in 5 in 200 mM Phosphate, pH6+150 mM NaCl. A 600 s injection of diluted B cell supernatant at 5 μl/min was used for capture by the immobilized anti-rat IgG,Fc. Human FcRn at 100 nM was injected over the captured B cell culture supernatant for 180 s at 30 μl/min followed by 360 s dissociation. Human IgG (Jackson ImmunoResearch) was injected over for 60 s with 180 s dissociation at 30 μl/min.

The data was analysed using T200 evaluation software (version 1.0) to determine affinity constants ($K_D$) of antibodies and determine those which blocked IgG binding.

As an alternative assay, master plate supernatants were also screened in a cell-based human IgG blocking assay. 25 ul of B cell culture supernatant from master plates were added to 96 well U-bottomed polypropylene plate. Mutant hFcRn-transfected HEK-293 cells (50,000 cells per well in 25 ul PBS pH6/1% FCS) were then added to each well and incubated for 1 hour at 4° C. Cells were washed twice with 150 ul of PBS media. Cells were then resuspended in 50 ul/well PBS/FCS media containing human IgG labelled with Alexafluor 488 or 649 at 7.5 ug/ml and incubated 1 hour at 4° C. Cells were then washed twice with 150 ul of media and then resuspended in 35 ul/well of PBS/FCS media containing 1% formaldehyde as fixative. Plates were then read on a FACS Canto 2 flow cytometer.

To allow recovery of antibody variable region genes from a selection of wells of interest, a deconvolution step had to be performed to enable identification of the antigen-specific B cells in a given well that contained a heterogeneous population of B cells. This was achieved using the Fluorescent foci method. Briefly, Immunoglobulin-secreting B cells from a positive well were mixed with streptavidin beads (New England Biolabs) coated with biotinylated human FcRn and a 1:1200 final dilution of a goat anti-rat or mouse Fcγ fragment-specific FITC conjugate (Jackson). After static incubation at 37° C. for 1 hour, antigen-specific B cells could be identified due to the presence of a fluorescent halo surrounding that B cell. These individual B cells, identified using an Olympus microscope, were then picked with an Eppendorf micromanipulator and deposited into a PCR tube. Fluorescent foci were generated from 268 selected wells.

Antibody variable region genes were recovered from single cells by reverse transcription polymerase chain reaction (RT)-PCR using heavy and light chain variable region-specific primers. Two rounds of PCR were performed on an Aviso Onyx liquid handling robot, with the nested 2° PCR incorporating restriction sites at the 3' and 5' ends allowing cloning of the variable regions into a mouse γ1 IgG (VH) or mouse kappa (VL) mammalian expression vector. Paired heavy and light chain constructs were co-transfected into HEK-293 cells using Fectin 293 (Invitrogen) and cultured in 48-well plates in a volume of 1 ml. After 5-7 days expression, supernatants were harvested and antibody subjected to further screening.

PCR successfully recovered heavy and light chain cognate pairs from single B cells from 156 of the selected wells. DNA sequence analysis of the cloned variable region genes identified a number of unique families of recombinant antibody. Following expression, transient supernatants were interrogated in both human IgG FACS blocking (described above) and IgG recycling assays. In some cases, purified mouse γ1 IgG was produced and tested (data labeled accordingly).

The recycling assay used MDCK II cells (clone as described in Examples 5, 6 and 7 below) over-expressing human FcRn and beta 2 microglobulin plated out at 25,000 cells per well of a 96 well plate. These were incubated overnight at 37° C., 5% $CO_2$. The cells were washed with HBSS+Ca/Mg pH 7.2+1% BSA and then incubated with 50p of varying concentrations of HEK-293 transient supernatant or purified antibody for 1 hour at 37° C., 5% $CO_2$. The supernatant was removed and 500 ng/ml of biotinylated human IgG (Jackson) in 50 µl of HBSS+Ca/Mg pH 5.9+1% BSA was added to the cells and incubated for 1 hour at 37° C., 5% $CO_2$. The cells were then washed three times in HBSS+Ca/Mg pH 5.9 and 100p of HBSS+Ca/Mg pH 7.2 added to the cells and incubated at 37° C., 5% $CO_2$ for 2 hours. The supernatant was removed from the cells and analysed for total IgG using an MSD assay with an anti-human IgG capture antibody (Jackson) and a streptavidin-sulpho tag reveal antibody (MSD). The inhibition curve was analysed by non-linear regression to determine IC50 values.

Based on performance in these assays a family of antibodies was selected comprising the six CDRs given in SEQ ID NOs 1 to 6. Antibody CA170_01638 had the best activity and was selected for humanisation.

Example 1 Humanisation Method

Antibody CA170_01638 was humanised by grafting the CDRs from the rat antibody V-regions onto human germline antibody V-region frameworks. In order to recover the activity of the antibody, a number of framework residues from the rat V-regions were also retained in the humanised sequence. These residues were selected using the protocol outlined by Adair et al. (1991) (Humanised antibodies WO91/09967). Alignments of the rat antibody (donor) V-region sequences with the human germline (acceptor) V-region sequences are shown in FIGS. 9A and B, together with the designed humanised sequences. The CDRs grafted from the donor to the acceptor sequence are as defined by Kabat (Kabat et al., 1987), with the exception of CDR-H1 where the combined Chothia/Kabat definition is used (see Adair et al., 1991 Humanised antibodies. WO91/09967). Human V-region IGKV1-27 plus JK4 J-region (http://www.imgt.org/) was chosen as the acceptor for the light chain CDRs. Human V-region IGHV3-7 plus JH3 J-region (http://www.imgt.org/) was chosen as the acceptor for the heavy chain CDRs.

Genes encoding a number of variant heavy and light chain V-region sequences were designed and constructed by an automated synthesis approach by Entelechon GmbH. Further variants of both heavy and light chain V-regions were created by modifying the VH and VK genes by oligonucleotide-directed mutagenesis. These genes were cloned into a number of vectors to enable expression of humanised 1638 Fab or IgG4 antibody in *E. coli* and mammalian cells, respectively. The variant chains, and combinations thereof, were assessed for their potency relative to the parent antibody, their biophysical properties and suitability for downstream processing, leading to the selection of the gL7 light chain graft and gH33 heavy chain graft. The final selected gL7 and gH33 graft sequences are shown in FIGS. 9A and B, respectively. This V-region pairing was named 1638.g49.

The light chain framework residues in graft gL7 are all from the human germline gene, with the exception of residues 70 and 71 (Kabat numbering), where the donor residues Histidine (H70) and Tyrosine (T71) were retained, respectively. Retention of these two residues was important for full potency of the humanised antibody or Fab. Residue 56 in CDRL2 of the gL7 graft was mutated from an Aspartic acid (D56) to a Glutamic acid (E56) residue, thus removing a potential Aspartic acid isomerization site from the gL7 sequence. The heavy chain framework residues in graft gH33 are all from the human germline gene, with the exception of residues 48 and 78 (Kabat numbering), where the donor residues Leucine (L48) and Alanine (A78) were retained, respectively. Retention of these two residues was essential for full potency of the humanised antibody or Fab.

For expression of 1638.g49 Fab in *E. coli*, the humanised heavy and light chain V-region genes were cloned into the UCB expression vector pTTOD, which contains DNA encoding the human C-kappa constant region (K1m3 allotype) and the human gamma-1 CH1 region (with or without hinge region) (G1m17 allotype).

For expression of 1638.g49 IgG4 in mammalian cells, the humanised light chain V-region gene was joined to a DNA sequence encoding the human C-kappa constant region (K1m3 allotype), to create a contiguous light chain gene. The humanised heavy chain V-region gene was joined to a DNA sequence encoding the human gamma-4 heavy chain constant region with the hinge stabilising mutation S241P (Angal et al., Mol Immunol. 1993, 30(1):105-8), to create a contiguous heavy chain gene. The heavy and light chain genes were cloned into a mammalian expression vector.

Another earlier graft, 1638.g28 was used in Example 8A described herein below and this contained more donor residues in the heavy chain (gH2) than the 1638.g49 graft (F24, L48, K71, T73, A78 and V93). Also the light chain of this antibody (gL2) contains the unmodified CDRL2 given in SEQ ID NO: 5 rather than the modified CDRL2 of SEQ ID NO: 7 which is used in 1638.g49. Sequences of both sets of antibodies are given in FIG. 8. Antibody 1638.g28 was expressed as a Fab' fragment as described above for 1638.g49.

Example 2 Preparation of 1638.g49 Fab'-PEG Conjugate

Fab' expressed in the periplasm of *E. coli* was extracted from cells by heat extraction. Fab' purified by Protein G affinity purification with an acid elution. Fab' reduced and PEGylated with 40 kDa PEG (SUNBRIGHT GL2-400MA3). PEG is covalently linked via a maleimide group to one or more thiol groups in the antibody fragment. PEGylation efficiency was confirmed by SE-HPLC. Fab'PEG was separated from un-PEGylated Fab' and diFab' by cation exchange chromatography. Fractions analyzed by SE-HPLC and SDS-PAGE. Pooling carried out to minimize levels of impurities. Final sample concentrated and diafiltered into desired buffer.

Example 3 Affinity for hFcRn Binding

Biomolecular interaction analysis using surface plasmon resonance technology (SPR) was performed on a Biacore T200 system (GE Healthcare) and binding to human FcRn extracellular domain determined. Human FcRn extracellular domain was provided as a non-covalent complex between the human FcRn alpha chain extracellular domain (SEQ ID NO: 48) and β2 microglobulin (β2M) (SEQ ID NO: 72). Affinipure F(ab')$_2$ fragment goat anti-human IgG, Fc fragment specific (for IgG4 capture) (Jackson ImmunoResearch Lab, Inc.) at 50 µg/ml in 10 mM NaAc, pH 5 buffer was immobilized on a CM5 Sensor Chip via amine coupling chemistry to a capture level between 5000-6000 response units (RU) using HBS-EP$^+$ (GE Healthcare) as the running buffer.

50 mM Phosphate, pH6+150 mM NaCl+0.05% P20 or HBS-P$^+$, pH7.4 (GE Healthcare) was used as the running buffer for the affinity assay. The antibody, 1638.g49 IgG4P was diluted to 1 µg/ml in running buffer. A 60 s injection of IgG4 at 10β1/min was used for capture by the immobilized anti-human IgG, Fc. Human FcRn extracellular domain was titrated from 20 nM to 1.25 nM over the captured anti-FcRn antibody (IgG4) for 300 s at 30l/min followed by 1200 s dissociation. The surface was regenerated by 2×60 s 50 mM HCl at 10 µl/min for the running buffer at pH6 or by 60 s 40 mM HCl and 30 s 10 mM NaOH for the running buffer at pH7.4.

The data was analysed using T200 evaluation software (version 1.0) using the 1:1 binding model with local Rmax.

TABLE 1

Affinity data for anti-hFcRn 1638.g49 IgG4P at pH 6.0 and pH 7.4

| 1638.g49 IgG4P | Human FcRn | | |
|---|---|---|---|
| | ka (M$^{-1}$s$^{-1}$) | kd (s$^{-1}$) | KD (M) |
| pH 6.0 | | | |
| 1 | 1.10E+06 | 1.43E−04 | 1.29E−10 |
| 2 | 1.10E+06 | 1.39E−04 | 1.26E−10 |
| 3 | 1.11E+06 | 1.40E−04 | 1.27E−10 |
| Mean | 1.10E+06 | 1.41E−04 | 1.27E−10 |
| pH 7.4 | | | |
| 1 | 9.75E+05 | 2.51E−05 | 2.57E−11 |
| 2 | 9.62E+05 | 3.19E−05 | 3.32E−11 |
| 3 | 9.62E+05 | 2.82E−05 | 2.93E−11 |
| Mean | 9.67E+05 | 2.84E−05 | 2.94E−11 |

The affinity of 1638.49 g IgG4 was therefore determined to be 127 pM at pH 6.0 and 29 pM at pH7.4.

Example 4

An IgG4P full length molecule and Fab-dsFv molecule where the 1638.g49 variable region was incorporated into the Fab domain of each format were analysed for biochemical integrity and biophysical stability.

Methods and Results

1. Sequence Confirmation.

i) Protein Sequencing (Edman Chemical Method)

The N-terminal amino acid sequence of both IgG4 and Fab-dsFv samples was obtained using an Applied Biosystems Procise 494 instrument. This was operated as recommended by the instrument manufacturer. Approximately 100 pmoles of each sample was applied to discs of polyvinylidene difluoride (Prosorb, used as per manufacturer's recommendations) and subjected to 18 cycles which included two blank runs and a standard hence resulting in the analysis of the first 15 amino acid residues of the heavy and light chains. Analysis was performed using SequencePro Data Analysis Application V2.0.

For each sample, the observed sequence was a mixture of two, approximately equally-abundant sequences, EVQLVESGGGLVQPG (SEQ ID NO: 67) and DIQMTQSPSSLSASV (SEQ ID NO: 68) consistent with the N-terminal sequences expected from the heavy and light chain gene sequences respectively. The approximately equal abundance suggested equal molar amounts of the 2 chains, with little to no significant N-terminal blockage.

ii) Mass Spectrometry Analysis a) Intact Mass Analysis

Intact mass spectrometry analysis was performed on two batches of the IgG4 and the Fab-dsFv molecule after reduction with 20 mM TCEP for one hour. Masses were measured on an Agilent 6510 mass spectrometer equipped with a chip cube interface and a C8 chip (43 mm Zorbax 300A C8 column+43 nL trap). All samples were diluted to 0.1 mg/ml in 98% water/2% methanol/0.3% formic acid (solvent A) prior to injection and 0.3 µL was loaded onto the system. Proteins were eluted from the chip into the mass spectrometer using a gradient to 40% acetonitrile/0.1% formic at 350 nL/min. ToF-MS data were collected in positive-ion mode between 500 and 5000 m/z and processed using Agilent MassHunter software.

The observed masses for both the light chain and the heavy chain for both formats is shown below (Table 2).

TABLE 2

Observed mass table of two IgG4 batches and Fab-dsFv

| | L-chain | | | H-chain | | |
|---|---|---|---|---|---|---|
| | Expected[1] | Observed | ppm | Expected[1] | Observed | ppm |
| IgG4 Batch#1 | 23503.3 | 23505.8 | 106 | 50764.7 | 50768.9 | 83 |
| IgG4 Batch#2 | | 23505.7 | 102 | | 50768.9 | 83 |

TABLE 2-continued

Observed mass table of two IgG4 batches and Fab-dsFv

|  | L-chain | | | H-chain | | |
|---|---|---|---|---|---|---|
|  | Expected[1] | Observed | ppm | Expected[1] | Observed | ppm |
| FabFv | 36384.4 | [L1] 36385.4 | 27 | 38298.8 | [H1] 38301.1 | 60 |
|  | | [L2] 36387.6 | 88 | | [H2] 38302.6 | 99 |

[1]Expected mass calculated from the amino acid sequence with the addition of IgG4: 2 L- and 4 H- intrachain disulphides, G0F glycosylation and clipping of C-terminal Lys from the H-chain FabFv: 3 L- and 3 H- intrachain disulphides.

The intact mass analysis of the TCEP reduced IgG4 was consistent with the expected sequences with predominantly G0F glycosylation and clipped C-terminal lysine (approximately 90%) on the H-chain which is typical of recombinant IgG.

Similarly the intact mass spectra of the Fab-dsFv chains was consistent with the sequence mass and expected number of disulphides. There was heterogeneity in the observed mass of both chains presumably due to partial reduction of the intra-chain disulphides by TCEP.

b) Disulphide Mapping was Performed on IgG4 Only.

IgG4 (50 ug) were treated with 0.15% Rapigest in Tris-HCl pH7.5 at 50° C. for 15 minutes and any free cysteines alkylated with iodoacetamide. Trypsin (1:25 w/w) was added and proteins were hydrolysed overnight at room temperature and then the reaction quenched by the addition of formic acid (5% v/v) and any precipitate was removed by centrifugation. Samples were stored at −20° C. and diluted 1:1 with water before loading on the LC-MS system. Aliquots (~3-5 ug) were loaded onto a 2.1×150 mm C18 column (Waters BEH1.7u) equilibrated with water containing 0.2% formic acid and eluted with a gradient of acetonitrile/1-propanol into a Waters Xevo mass spectrometer operated in +ve-ion $MS^E$ mode. Data was analysed with MassLynx and BioPharmaLynx software.

The results indicated that all the expected disulphide-linked peptides were observed except the inter H-H-chain peptide T19-SS-T19 species which was only observed with a single disulphide bond and at low intensity. There was no evidence for any scrambled disulphide species or carbamidomethylated cysteine residues.

2. Biochemical Analysis

Size Exclusion Chromatography HPLC (SEC HPLC)

Size exclusion chromatography allowed analysis of monomeric and oligomeric material.

It was performed using a TSK G3000SW (7.7 mm I.D×30.0 cm L) column connected to an Agilent 1100 system. The samples (25 μl/25 pg injection) were eluted isocratically in 0.2 M sodium phosphate, pH 7 at 1.0 ml/min for 30 minutes, 30° C. Elution was monitored by absorption at 280 nm.

The elution profiles showed that the IgG4 and Fab-dsFv were homogeneous and eluted at expected retention times as judged by SEC standards (BioRad 151-1901).

3. Molecular Charge.

Capillary isoelectric focusing (cIEF) was conducted to estimate pI and acidic species content.

IgG4 and Fab-dsFv samples were diluted to 1 mg/ml in HPLC grade water for analysis (non-reduced condition). The samples were also subjected to reduction (2 mM THP/30 minutes) and alkylation (20 mM iodoacetamide/80 minutes) to analyse for cysteine adducts.

Samples were prepared by mixing the following: 30 μl protein sample, 0.35% methylcellulose, 4% pH3-10 ampholytes (Pharmalyte), 1 μl of each synthetic pI marker (4.65 and 9.77) and HPLC grade water to make up the final volume to 100 μl. The mixture was then analysed using iCE280 IEF analyser (Convergent Biosciences), pre-focusing at 1500 V for 1 minute followed by focusing at 3000 V for 6 minutes. The calibrated electropherograms were then integrated using Empower software (from Waters).

The pI was taken to be that of the main species (largest peak).

For the IgG4 format, the main species had a pI of 7.3. This was assumed to be the clipped parent molecule (removal of the C terminal lysine, corroborated by mass spectrum analysis) which is not atypical for IgG molecules. The clipped molecule would be more acidic that the parent molecule (basic peak at 7.4). There was no change to the pI profile pre- and post-reduction and alkylation, indicating that there were no cysteine adducts.

For the Fab-dsFv format, the pI was taken to be that of the main species (largest peak) which was 9.0. A more acidic species (pI 8.8) was also evident which was less prominent post reduction/alkylation indicating the presence of a reducible adduct.

For both formats, minor peaks were present being either acidic (to the left of the main peak) or basic (to the right of the main peak). These species were presumed to be derivatives of the main species, but were not characterised further.

4. Thermal Stability ($T_m$)

When heated, a protein will tend to unfold, and the more stably-folded a protein structure is, the more heat is required to unfold it. Therefore, thermal stability (measured as melting temperature, $T_m$) is a measure of the stability of folding of a protein, or resistance of a molecule to unfolding (denaturation), which may be a prerequisite to aggregate formation. In a temperature gradient, in defined conditions, the temperature at which 50% of molecules are unfolded is $T_m$.

$T_m$ estimations were made by two independent methods i) Thermofluor Assay, measurement of 50% unfolding by binding of a fluorescent dye (Sypro Orange) to exposed hydrophobic surfaces that become exposed upon heat induced unfolding and ii) Differential Scanning Calorimetry (DSC).

Results from the two techniques generally correlate, differing slightly in absolute value because methods employed are different.

i) Thermofluor Assay

Samples were prepared as follows: 5 μl of 30× sypro orange was placed in a 96 well V-bottomed plate. Then, 45 μl of protein sample at 0.1 mg/ml was then added. This mix was pipetted, in 10 μl quadruplicates, into a 384 well plate. The format of the 384 well plate was: sample 1: wells A1, B1, A2, B2; sample 2: wells C1, D1, C2, D2. An inter-assay control was included, being an irrelevant IgG4. This control, at 0.1 mg/ml (in PBS pH 7.4) was added to 5 μl of 30× concentrated dye, 10 µl of this master mix being placed into the 384 well in quadruplicate. The plates were placed in a 7900HT fast real-time PCR system and heated from 20° C. to 99° C. using a ramp rate of 1.1° C./min; a CCD device simultaneously monitors the fluorescence changes in the wells. A modified XE template (IDBS) is used to process the intensity data and take into account multiple transitions.

Two unfolding transitions were evident for both the IgG4 and the Fab-dsFv molecules. The $T_m$ 2 value for both molecules represented the Fab unfolding domain and was shown to be slightly lower for the IgG4 format. The $T_m1$ value represented the CH2 (constant heavy chain) domain and the dsFv domain of the IgG4 and Fab-dsFv molecule respectively. The Fab-dsFv format was shown to be more thermally stable than the IgG format in PBS, pH 7.4.

| Sample | $T_m$ 1 Mean (° C.) | $T_m$ 1 SD | $T_m$ 2 Mean (° C.) | $T_m$ 2 SD |
|---|---|---|---|---|
| IgG4 | 65.4 | 0.1 | 81.1 | 0.4 |
| Fab-dsFv | 73.6 | 0.4 | 83.1 | 0.4 | ii) DSC Method

DSC analysis was performed on the Fab-dsFv molecule only for corroboration of the Thermofluor data and to determine the effect of two different buffer types (PBS pH7.4 and 50 mM sodium acetate/125 mM sodium chloride, pH 5.0) on the thermal stability.

Samples at 1 mg/ml in PBS pH7.4 and 50 mM sodium acetate/125 mM sodium chloride, pH 5.0 with respective reference buffers were loaded onto the MicroCal VP Capillary DSC instrument in triplicate. The system settings included temperature scan from 20° C. to 110° C. and a scan rate of 60° C./hr. The final thermograms were processed using Origin software according to the manufacturer's instructions. The $T_m$ was determined using software's automated $T_m$ detection algorithm (for the main transition) and manually peak picked for any other transitions that was not automatically detected by the software.

Two distinct transitions could be observed in the two buffers tested.

The lower infolding transition ($T_m$ 1) represented the dsFv domain of the Fab-dsFv molecule and the higher transition temperature ($T_m$ 2) represented the Fab domain.

The DSC data was in good agreement with the data obtained from the Thermofluor assay. This technique was capable of being able to discriminate between the two unfolding domains more easily than the Thermofluor assay.

The Fab-dsFv molecule showed a slight increase in thermal stability in the 50 mM sodium acetate/125 mM sodium chloride, pH 5.

| Buffer | $T_{m1\ mean}$ (° C.) | SD | $T_{m2\ mean}$ (° C.) | SD |
|---|---|---|---|---|
| Fab-dsFv (50 mM NaOAc/ 125 mM NaCl, pH 5) | 86.1 | 0 | 73.6 | 0.15 |
| Fab-dsFv (PBS, pH 7.4) | 84.1 | 0.1 | 71.2 | 0.06 |

5. Molecular Structure: Attenuated Total Reflectance Fourier Transform Infra-Red Spectroscopy (ATR FTIR)

This technique was used to compare the extent of interaction between β-sheets within the molecule (intra-β-sheet) and between separate molecules (inter-β-sheet).

The analysis was performed using the Bruker Tensor 27 FTIR spectrometer and the BIOATR 11 cell sampling accessory using a resolution of 4 cm$^{-1}$; 120 scans; aperture setting 6 mm and 20 µL sample volume at 20° C. where the following procedure was performed for the analysis of the Fab-dsFv only.

1. Five air background spectra were measured using the method BIOATR 10 06 10. xpm.
2. 20 µL of sigma PBS pH7.4 was added to the cell and then removed
3. 20 µL of sigma PBS pH7.4 was added to the cell and a spectrum was taken, the buffer was removed and fresh buffer was added and a spectrum taken (in duplicate).
4. 20 µL of sample was added to the cell and a spectrum was taken, the sample was then removed from the cell.
5. 20 µL of sigma PBS pH7.4 was added to the cell and removed
6. 20 µL of sample was added to the cell and a spectrum was taken, the sample was then removed from the cell. (in duplicate)
7. The cell was then cleaned following procedure below:
    a. 20 µL 1% SDS added to cell+cleaned with Q-tip
    b. 20 µL 1% SDS added to cell and removed
    c. 5 times 20 µL H2O added to cell and removed
    d. 20 µL buffer added to cell and removed
8. The data was analysed to produce the final data format in the following way.
    a. Buffer spectrum 1 was subtracted from the Fab-dsFv spectrum 1 and then repeated with buffer spectrum 2 and Fab-ds Fv spectrum 2.
    b. The data was cut to 2200 cm-1 to 1000 cm-1
    c. The duplicate spectra were averaged.
    d. A second derivative was then taken with a 25 point smoothing. This was the final data format shown.

The results of the analysis showed that the Fab-dsFv had the intra-beta sheet characteristics typical of antibody molecules.

Example 5 Cell-Based Potency

Cell-based assays were performed using Madin-Darby Canine Kidney (MDCK) II cells which had been stably transfected with a human FcRn and human β2M double gene vector with a Geneticin selection marker. A stable cell clone was selected that was able to recycle and transcytose human IgG and this was used for all subsequent studies. It will be referred to as MDCK II clone 15.

Cell Based Affinity of CA170_1638.g49 IgG4 for Human FcRn

Quantitative flow cytometry experiments were performed using MDCK II clone 15 cells and AlexaFluor 488-labelled CA170_1638.g49 IgG4. Specific binding of antibody to FcRn across a range of antibody concentrations was used to determine $K_D$. The analyses were performed in both neutral and acidic buffers to determine whether environmental pH comparable to that found in blood plasma (pH7.4) or endosomes (pH6) had any effect on the antibody binding.

FIG. 2 shows representative binding curves for CA170_1638.g49 IgG4 The mean $K_D$ values (n=3) were 0.20 in neutral buffer, and 0.22 in acidic buffer, respectively (see Table 4).

TABLE 4

Mean $K_D$ values (nM) for CA170_1638.g49 IgG4 on MDCK II clone 15 cells.

| Antibody format | Human FcRnpH 7.4 | Human FcRnpH 6.0 |
|---|---|---|
| 1638.g49 IgG4 | 0.20 | 0.22 |

FIG. 2 shows CA170_1638.g49 IgG4 binding on MDCK II clone 15 cells in acidic and neutral pH.

MDCK II clone 15 cells were incubated in Facs buffer (PBS with 0.2% w/v BSA, 0.09% w/v NaN3) for 30 mins prior to the addition of Alexa-fluor 488-labelled CA170_1638.g49 IgG4 for 1 hour in Facs buffer at either pH 7.4 or pH 6. The final antibody concentrations ranged from 400 nM to 0.003 nM. The cells were washed in ice cold Facs buffer then analysed by flow cytometry using a Guava flow cytometer (Millipore, UK). Titration data sets were also produced for isotype control antibodies for each antibody format to determine non-specific binding. The number of moles of bound antibody was calculated using interpolated values from a standard curve generated from beads comprised of differing amounts of fluorescent dye. Geometric mean fluorescence values were determined in the flow cytometric analyses of cells and beads. Non-specific binding was subtracted from the anti-FcRn antibody values and the specific binding curve generated was analysed by non-linear regression using a one-site binding equation (Graphpad Prism®) to determine the $K_D$. Data is representative of 3 experiments. CA170_1638.g49 IgG4 can bind human FcRn expressed on cells at both acidic and neutral pH Example 6 Functional Cell Based Assays FcRn expression is primarily intracellular (Borvak J et al. 1998, Int. Immunol., 10 (9) 1289-98 and Cauza K et al. 2005, J. Invest. Dermatol., 124 (1), 132-139), and associated with endosomal and lysosomal membranes. The Fc portion of IgG binds to FcRn at acidic pH (<6.5), but not at a neutral physiological pH (7.4) (Rhagavan M et al. 1995) and this pH-dependency facilitates the recycling of IgG.

Once it is taken up by pinocytosis and enters the acidic endosome, IgG bound to FcRn will be recycled along with the FcRn to the cell surface, whereas at the physiologically neutral pH the IgG will be released. (Ober R J et al. 2004, The Journal of Immunology, 172, 2021-2029). Any IgG not bound to FcRn will enter the lysosomal degradative pathway.

An in vitro assay was established to examine the ability of CA170_1638.g49 IgG4 to inhibit the IgG recycling capabilities of FcRn. Briefly, MDCK II clone 15 cells were incubated with biotinylated human IgG, in the presence and absence of 1638 IgG4 in an acidic buffer (pH 5.9) to allow binding to FcRn. All excess antibody was removed and the cells incubated in a neutral pH buffer (pH 7.2) which allows release of surface-exposed, bound and internalised IgG into the supernatant. The inhibition of FcRn was followed using an MSD assay to detect the amount of IgG recycled and thus released into the supernatant.

FIG. 3 shows CA170_1638.g49 IgG4 inhibits IgG recycling in MDCK II clone 15 cells. MDCK II clone 15 cells were plated at 15,000 cells per well in a 96 well plate and incubated overnight at 37° C., 5% $CO_2$. The cells were incubated with 1 ug/ml of biotinylated human IgG (Jackson) in the presence and absence of CA170_1638.g49 IgG4 in HBSS$^+$ (Ca/Mg) pH 5.9+1% BSA for 1 hour at 37° C., 5% $CO_2$. The cells were washed with HBSS+pH 5.9 then incubated at 37° C., 5% $CO_2$ for 2 hours in HBSS+pH 7.2. The supernatant was removed from the cells and analysed for total IgG using an MSD assay (using an anti-human IgG capture antibody (Jackson) and a streptavidin-sulpho tag reveal antibody (MSD)). The inhibition curve was analysed by non-linear regression (Graphpad Prism®) to determine the $EC_{50}$. The graph represents combined data from 3 experiments. As shown in FIG. 3 CA170_1638.g49 IgG4 inhibits IgG recycling in a concentration dependent manner with a mean $EC_{50}$ value (n=3) of 0.31 nM.

CA170_1638.g49 IgG4 and FabFv Inhibits the Transcytosis of Human IgG

FcRn can traffic IgG across polarised epithelial cell layers in both the apical to basolateral and basolateral to apical directions and thus plays an important role in permitting IgG to move between the circulation and lumen at mucosal barriers (Claypool et al. 2004 Mol Biol Cell 15(4):1746-59). FcRn can traffic IgG across polarised epithelial cell layers in both the apical to basolateral and basolateral to apical directions and thus plays an important role in permitting IgG to move between the circulation and lumen at mucosal barriers (Claypool et al. 2004 Mol Biol Cell 15(4):1746-59). An in vitro assay was established to examine the ability of CA170_1638.g49 IgG4 and FabFv to inhibit FcRn dependent IgG transcytosis. Briefly, MDCK II clone 15 cells were plated in a 24 well transwell plate and allowed to form monolayers over 3 days. The cells were then incubated with biotinylated human IgG in an acidic buffer which facilitates binding to FcRn, on the apical side, in the presence and absence of CA170_1638.g49 IgG4 or FabFv. The human IgG is transcytosed through the cells from the apical to basolateral side and released into a neutral buffer in the lower chamber. Levels of IgG on the basolateral side were then measured using an MSD assay.

FIGS. 4 and 5 shows CA170_1638.g49 IgG4 and FabFv inhibits apical to basolateral IgG transcytosis in MDCK II clone 15 cells. MDCK II clone 15 cells were plated at 500,000 cells per well of a 24 well transwell plate and incubated for 3 days at 37° C., 5% $CO_2$ until monolayers were formed. The pH of the apical compartment was adjusted to 5.9 and the basolateral side to 7.2 in a HBSS+ (Ca/Mg) buffer+1% BSA. Cells on the apical compartment were incubated with 1p g/ml biotinylated human IgG (Jackson) in the presence and absence of CA170_1638.g49 IgG4 or FabFv at the indicated concentrations for 4 hours at 37° C., 5% $CO_2$. The basolateral medium was then collected and total IgG measured by MSD assay (using an anti-human IgG capture antibody (Jackson) and a streptavidin-sulpho tag reveal antibody (MSD)). The inhibition curve was analysed by non-linear regression (Graphpad Prism®) to determine the $EC_{50}$. The graph represents combined data from 3 experiments.

In summary FIGS. 4 and 5 shows that CA170_1638.g49 IgG4 and FabFv can inhibit the apical to basolateral transcytosis of human IgG in a concentration dependent manner with an $EC_{50}$ value of 2.4 and 0.42 nM respectively (n=3). Summary of In Vitro Effects of CA170_1638.g49 IgG4 and FabFv CA170_1638.g49 IgG4 and FabFv inhibit both IgG recycling and transcytosis. The $EC_{50}$ of 0.31 nM achieved in the IgG recycling assay is comparable to the cell affinity binding data in which $K_D$ values of 0.2 nM in neutral buffer and 0.22 nM in acidic buffer were obtained. In the IgG transcytosis assay, an $EC_{50}$ of 2.4 nM and 0.42 nM was obtained for CA170_1638.g49 IgG4 and FabFv respectively, demonstrating a slight reduction in potency between the IgG4 and the FabFv. However, the data in this section have clearly shown that CA170_1638.g49 IgG4 and FabFv can inhibit human FcRn function.

Example 7 Cross Reactivity of CA170_1638.g49 IgG4 with Non-Human Primate FcRn

To validate the use of CA170_1638.g49 IgG4 in a non-human primate PK/PD study and pre-clinical toxicology, its relative affinity with cynomolgus macaque FcRn was examined. MDCK II cells stably transfected with cynomolgus macaque FcRn and B2M (MDCKII (Clone 40) was used in a cell based assay, alongside the previously described MDCK II cells stably transfected with human FcRn and B2M (MDCK II clone 15).

FIG. 6 shows CA170_1638.g49 IgG4 IgG4 binding on MDCK II clone 40 cells in acidic and neutral pH. Specific binding of antibody to FcRn across a range of antibody concentrations was used to determine $K_D$. The analyses were performed in both neutral and acidic buffers to determine whether environmental pH comparable to that found in blood plasma (pH7.4) or endosomes (pH6) had any effect on the antibody binding.

FIG. 6 shows representative binding curves for CA170_1638.g49 IgG4. The mean $K_D$ values (n=3) were 0.3 in neutral buffer, and 0.43 in acidic buffer, respectively (see Table 5).

TABLE 5

Mean $K_D$ values (nM) for CA170_1638.g49 IgG4 on MDCK II clone 40 cells.

| Antibody format | Cyno FcRnpH 7.4 | Cyno FcRnpH 6.0 |
| --- | --- | --- |
| 1638 IgG4 | 0.30 | 0.43 |

Example 8A Anti-FcRn Treatment Enhances the Clearance of hIgG In Vivo in hFcRn Transgenic Mice The effect of anti-FcRn molecules (CA170_01519.g57 Fab'PEG (described in WO2014/019727) and CA170_01638.g28 Fab'PEG) on the clearance of human IVIG was determined in human FcRn transgenic mice (B6.Cg-Fcgrt$^{tm1Dcr}$ Tg(FCGRT)32Dcr/DcrJ, JAX Mice). Mice were infused intravenously with 500 mg/kg human IgG (Human IgI 10% Gamunex-c, Talecris Biotherapeutics). 24 hours later animals were dosed with vehicle control (PBS) or anti-FcRn intravenously as a single dose (100 mg/kg). Serial tail tip blood samples were taken at −24, 8, 24, 48, 72, 96, 144 and 192 hours relative to anti-FcRn treatment. Serum levels of human IgG in hFcRn mice were determined by LC-MS/MS. Data presented in FIG. 1 are mean±SEM with 5-6 mice per treatment group. Blocking of hFcRn by each of the anti-FcRn molecules tested resulted in accelerated clearance of hIVIG and lower concentrations of total IgG were observed compared to control mice.

Example 8B. Anti-FcRn Treatment Enhances the Clearance of hIgG In Vivo in hFcRn Transgenic Mice The anti-human FcRn antibody discovered bound to and inhibited the binding of human IgG to human FcRn, but did not bind or inhibit murine FcRn. Consequently, the effect of anti-FcRn molecules in IgG4P format (1638.g49), Fab'PEG format (1638.g28), and FabFv format on the clearance of human IVIg was determined in human FcRn transgenic mice (B6.Cg-Fcgrttm1Dcr Tg(FCGRT)32Dcr/DcrJ, JAX Mice). Mice were infused intravenously with 500 mg/kg human IgG (Human IgI 10% Gamunex-c, Talecris Biotherapeutics). 24 hours later animals were dosed with vehicle control (PBS) or anti-FcRn intravenously as a single dose. Doses, sampling times and replicate numbers were as indicated in the FIGS. 1a to 1e. Samples were serial tail tip blood samples. Serum levels of human IgG, endogenous mouse albumin and the anti-FcRn molecule itself were determined by LC-MS/MS, with detection and quantification of peptide sequences unique to each of those analytes. Data presented in FIGS. 1a to 1e are each the Geometric mean and 95% confidence interval.

Blockade of hFcRn by each of the three anti-FcRn molecules tested resulted in clearance of hIVIg that was accelerated compared to that in control mice that were treated with vehicle only, or with a control Fab'PEG (A33, not anti-FcRn, conjugated to 40 kDa PEG, as was 1638 Fab'PEG)—see FIGS. 1a and 1b. The effect was dose-related—larger doses gave more prolonged periods during which free anti-FcRn could be detected in serum (FIGS. 1 c and 1d), this leading to a more prolonged, and more profound clearance of human IVIg from the mice. The 1638 Fab'PEG showed shorter pharmacokinetics (disappeared more rapidly from free solution in serum) than the control A33 Fab'PEG did, suggesting that the 1638 Fab'PEG had undergone target-mediated disposition—disappearing from free solution by binding to FcRn target. Although mouse IgG did not bind to the human FcRn present in these transgenic mice, endogenous mouse albumin did bind and was recycled by the human FcRn. Although binding of anti-human FcRn to human FcRn did not block binding of albumin to the FcRn in in vitro assay, if such inhibition occurred in vivo, it might have led to accelerated clearance of endogenous mouse albumin. Data are shown in FIG. 1e. Since albumin concentration in serum was somewhat variable (from 16.6 to 59.9 mg/mL in a group of 30 mice, prior to injection of anti-FcRn drug), to allow easier comparison of group results, albumin data were normalised and given as a percentage of the serum albumin concentration at time zero in FIG. 1e. A recoverable effect on plasma albumin concentration might have occurred after dosing with Fab'PEG or FabFv formats. Analysis of variance (ANOVA) was carried out for repeated measurements, looking at the treatment differences and the time differences simultaneously. Each measurement of Fab'PEG or FabFv-treated animal compared to the control in the same experiment at the same time point, the controls being irrelevant (non-FcRn-binding) Fab'PEG or vehicle only, respectively. These two formats showed a lowering of albumin concentrations (at 5% level in the ANOVA analysis of data) at around 48 to 72 hours post injection of drug, with levels recovering to pre-dose levels thereafter. The maximum reduction of plasma albumin concentration was about 10% after 100 mg/kg of the Fab'PEG format (at 48 hours), or about 25% after 250 mg/kg FabFv at 144 hours. A similar ANOVA analysis was carried out on data showing the effect of 1638 IgG4P on plasma albumin levels (shown in FIG. 1f). There was no significant difference between treated and control animals, suggesting that treatment with the IgG4P format of 1638 did not affect plasma albumin concentration.

Example 9 Crystal Structure and Analysis of 1638.g49 Fab: FcRn Complex

The 1638.g49 Fab was co-crystalised with hFcRn alpha chain ECD region (SEQ ID NO: 48) and human beta 2 microglobulin (SEQ ID NO: 72). The proteins were in 50 mM Sodium Acetate, 125 mM NaCl pH6.0 and a crystallisation conditions were 0.1M Tris pH8.5, 40% PEG400 and 0.2M LiSO$_4$.H$_2$O at a protein concentration of 10 mg/mL and a drop volume ratio of 0.4 µL protein to 0.4 µL reservoir in a sitting drop, vapour diffusion experiment. Crystals were allowed to grow for 8-21 days, followed by harvesting from the drop, transfer to well buffer (since it already contained 40% PEG400) and flash-frozen in liquid nitrogen (−180° C.) within 10 seconds. X-ray data was collected at SOLEIL, using the oscillation method. The cell dimensions of the crystals were a=101.49 Å, b=210.4 Å, c=101.49 Å; alpha=90 degrees, beta=90 degrees and gamma=90 degrees. The space group was determined to be $P2_12_12$. The molecular packing was determined using Phaser, and refinement was carried out with Refmac, using data between 30 and 2.7 Å, to give a final R factor of 21.8% and Rfree of 27.2%. The results are shown below:

The residues interacting with 1638.49 Fab' were all in the FcRn α chain (not β2M) and are indicated below in bold in the FcRn extracellular domain sequence

```
                                          (SEQ ID NO: 48)
AESHLSLLYHLTAVSSPAPG TPAFWVSGWL GPQQYLSYNS

LRGEAEPCGA WVWENQVSWY WEKETTDLRI KEKLFLEAFK

ALGGKGPYTL QGLLGCELGPDNTSVPTAKFALNGEEFMNFDLK

QGTWGGDWPEALAISQR WQQQDKAANK ELTFLLFSCP

HRLREHLERG RGNLEWKEPPSMRLKARPSSPGFSVLTCSA

FSFYPPELQL RFLRNGLAAG TGQGDFGPNSDGSFHASSSLTV

KSGDEHHYCCIVQHAGLAQPLRVELESPAKSS.
```

The residues underlined are those known to be critical for the interaction of human FcRn with the Fc region of human IgG. Those in bold are residues involved in binding the 1638.49 Fab' antibody at 4 Å. Residues in italic are those involved in binding the same antibody at 5 Å.

The epitope defined by antibody residues closer than 4 Å was: A81, G83, G84, K85, G86, P87, N113, E115, W131, P132, E133, L135, A136, Q139.

The epitope defined by antibody residues closer than 5 Å was: A81, G83, G84, K85, G86, P87, N113, E115, W131, P132, E133, L135, A136, Q139, L82, Y88, L112, D130.

The ASCII text file named "CELL0018-371-DIV-1 Sequence Listing," created on Mar. 12, 2019, comprising 91 kilobytes, is hereby incorporated by reference in its entirety.

We claim:

1. An isolated DNA molecule or a pair of isolated DNA molecules encoding the heavy and light chains of an anti-FcRn antibody or FcRn-binding fragment thereof, wherein
the heavy chain comprises three CDRs, wherein CDR H1 has the sequence given in SEQ ID NO: 1, CDR H2 has the sequence given in SEQ ID NO: 2, and CDR H3 has the sequence given in SEQ ID NO: 3, and
the light chain comprises three CDRs, wherein CDR L1 has the sequence given in SEQ ID NO: 4, CDR L2 has the sequence given in SEQ ID NO: 5 or SEQ ID NO: 7 and CDR L3 has the sequence given in SEQ ID NO: 6.

2. The isolated DNA molecule or pair of isolated DNA molecules according to claim 1, wherein the anti-FcRn antibody or FcRn-binding fragment thereof has a heavy chain comprising the sequence given in SEQ ID NO:12 and a light chain comprising the sequence given in SEQ ID NO: 8.

3. The isolated DNA molecule or pair of isolated DNA molecules according to claim 1, wherein the antibody is humanized.

4. The isolated DNA molecule or pair of isolated DNA molecules according to claim 1, wherein the heavy chain comprises the sequence given in SEQ ID NO: 25 and the light chain comprises the sequence given in SEQ ID NO: 16.

5. The isolated DNA molecule or pair of isolated DNA molecules according to claim 1, wherein the heavy chain comprises the sequence given in SEQ ID NO: 59 and the light chain comprises the sequence given in SEQ ID NO: 51.

6. The isolated DNA molecule or pair of isolated DNA molecules according to claim 1, wherein the heavy chain comprises a sequence having at least 80% identity to the sequence given in SEQ ID NO: 25 and wherein the light chain comprises a sequence having at least 80% identity to the sequence given in SEQ ID NO: 16.

7. The isolated DNA molecule or pair of isolated DNA molecules according to claim 1, wherein the FcRn-binding fragment is a scFv, Fv, Fab or Fab' fragment.

8. The isolated DNA molecule or pair of isolated DNA molecules according to claim 7, wherein the FcRn-binding fragment is a Fab' fragment having a heavy chain comprising the sequence given in SEQ ID NO: 33 and a light chain comprising the sequence given in SEQ ID NO: 20.

9. The isolated DNA molecule or pair of isolated DNA molecules according to claim 7, wherein the FcRn-binding fragment is a Fab fragment having a heavy chain comprising the sequence given in SEQ ID NO: 29 and a light chain comprising the sequence given in SEQ ID NO: 20.

10. The isolated DNA molecule or pair of isolated DNA molecules according to claim 7, wherein the FcRn-binding fragment is a Fab' fragment having a heavy chain comprising the sequence given in SEQ ID NO: 63 and a light chain comprising the sequence given in SEQ ID NO: 55.

11. The isolated DNA molecule or pair of isolated DNA molecules according to claim 1, encoding a Fab-dsFv having a heavy chain comprising the sequence given in SEQ ID NO: 42 and a light chain comprising the sequence given in SEQ ID NO: 40.

12. The isolated DNA molecule or pair of isolated DNA molecules according to claim 1, wherein the anti-FcRn antibody is a full length antibody.

13. The isolated DNA molecule or pair of isolated DNA molecules according to claim 12, wherein the full length antibody is selected from the group consisting of an IgG1, IgG4 and IgG4P.

14. The isolated DNA molecule or pair of isolated DNA molecules according to claim 13, wherein the antibody has a heavy chain comprising the sequence given in SEQ ID NO: 37, SEQ ID NO:39 or SEQ ID NO:73 and a light chain comprising the sequence given in SEQ ID NO: 20.

15. A cloning or expression vector or a pair of cloning or expression vectors encoding the heavy and light chains of an anti-FcRn antibody or FcRn-binding fragment thereof, wherein
the heavy chain comprises three CDRs, wherein CDR H1 has the sequence given in SEQ ID NO: 1, CDR H2 has the sequence given in SEQ ID NO: 2, and CDR H3 has the sequence given in SEQ ID NO: 3, and
the light chain comprises three CDRs, wherein CDR L1 has the sequence given in SEQ ID NO: 4, CDR L2 has the sequence given in SEQ ID NO: 5 or SEQ ID NO: 7 and CDR L3 has the sequence given in SEQ ID NO: 6.

16. The cloning or expression vector or pair of cloning or expression vectors according to claim 15, wherein the antibody is humanized.

17. The cloning or expression vector or pair of cloning or expression vectors according to claim 15, wherein the heavy chain comprises the sequence given in SEQ ID NO: 25 and the light chain comprises the sequence given in SEQ ID NO: 16.

18. The cloning or expression vector or pair of cloning or expression vectors according to claim 15, wherein the heavy chain comprises a sequence having at least 80% identity to the sequence given in SEQ ID NO: 25 and wherein the light chain comprises a sequence having at least 80% identity to the sequence given in SEQ ID NO: 16.

19. The cloning or expression vector or pair of cloning or expression vectors according to claim 15, wherein the FcRn-binding fragment is a scFv, Fv, Fab or Fab' fragment.

20. The cloning or expression vector or pair of cloning or expression vectors according to claim 19, wherein the FcRn-binding fragment is a Fab' fragment having a heavy chain comprising the sequence given in SEQ ID NO: 33 and a light chain comprising the sequence given in SEQ ID NO: 20.

21. The cloning or expression vector or pair of cloning or expression vectors according to claim 19, wherein the FcRn-binding fragment is a Fab fragment having a heavy chain comprising the sequence given in SEQ ID NO: 29 and a light chain comprising the sequence given in SEQ ID NO: 20.

22. The cloning or expression vector or pair of cloning or expression vectors according to claim 15, encoding a FabdsFv having a heavy chain comprising the sequence given in SEQ ID NO: 42 and a light chain comprising the sequence given in SEQ ID NO: 40.

23. The cloning or expression vector or pair of cloning or expression vectors according to claim 15, wherein the anti-FcRn antibody is a full length antibody.

24. The cloning or expression vector or pair of cloning or expression vectors according to claim 23, wherein the full length antibody is selected from the group consisting of an IgG1, IgG4 and IgG4P.

25. The cloning or expression vector or pair of cloning or expression vectors according to claim 24, wherein the antibody has a heavy chain comprising the sequence given in SEQ ID NO: 37, SEQ ID NO:39 or SEQ ID NO:73 and a light chain comprising the sequence given in SEQ ID NO: 20.

26. The cloning or expression vector or pair of cloning or expression vectors according to claim 15, which comprises (i) the sequence given in SEQ ID NO: 30, 32, 34 or 36 and the sequence given in SEQ ID NO: 21 or 24 or (ii) the sequence given in SEQ ID NO: 38 and the sequence given in SEQ ID NO: 22, or (iii) the sequence given in SEQ ID NO: 74 and the sequence given in SEQ ID NO: 22 or (iv) the sequence given in SEQ ID NO: 41 and the sequence given in SEQ ID NO: 43.

27. A host cell comprising a cloning or expression vector or a pair of cloning or expression vectors encoding the heavy and light chains of an anti-FcRn antibody or FcRn-binding fragment thereof, wherein
the heavy chain comprises three CDRs, wherein CDR H1 has the sequence given in SEQ ID NO: 1, CDR H2 has the sequence given in SEQ ID NO: 2, and CDR H3 has the sequence given in SEQ ID NO: 3, and
the light chain comprises three CDRs, wherein CDR L1 has the sequence given in SEQ ID NO: 4, CDR L2 has the sequence given in SEQ ID NO: 5 or SEQ ID NO: 7 and CDR L3 has the sequence given in SEQ ID NO: 6.

28. The host cell according to claim 27, wherein the antibody is humanized.

29. The host cell according to claim 27, wherein the heavy chain comprises the sequence given in SEQ ID NO: 25 and the light chain comprises the sequence given in SEQ ID NO: 16.

30. The host cell according to claim 27, wherein the heavy chain comprises a sequence having at least 80% identity to the sequence given in SEQ ID NO: 25 and wherein the light chain comprises a sequence having at least 80% identity to the sequence given in SEQ ID NO: 16.

31. The host cell according to claim 27, wherein the FcRn-binding fragment is a scFv, Fv, Fab or Fab' fragment.

32. The host cell according to claim 31, wherein the FcRn-binding fragment is a Fab' fragment having a heavy chain comprising the sequence given in SEQ ID NO: 33 and a light chain comprising the sequence given in SEQ ID NO: 20.

33. The host cell according to claim 31, wherein the FcRn-binding fragment is a Fab fragment having a heavy chain comprising the sequence given in SEQ ID NO: 29 and a light chain comprising the sequence given in SEQ ID NO: 20.

34. The host cell according to claim 27, wherein the vector or pair of vectors encode a Fab-dsFv having a heavy chain comprising the sequence given in SEQ ID NO: 42 and a light chain comprising the sequence given in SEQ ID NO: 40.

35. The host cell according to claim 27, wherein the anti-FcRn antibody is a full length antibody.

36. The host cell according to claim 35, wherein the full length antibody is selected from the group consisting of an IgG1, IgG4 and IgG4P.

37. The host cell according to claim 36, wherein the anti-FcRn antibody has a heavy chain comprising the sequence given in SEQ ID NO: 37, SEQ ID NO:39 or SEQ ID NO:73 and a light chain comprising the sequence given in SEQ ID NO: 20.

38. A process for the production of an anti-FcRn antibody or FcRn-binding fragment thereof, the process comprising culturing a host cell that comprises a cloning or expression vector or a pair of cloning or expression vectors encoding the heavy and light chains of an anti-FcRn antibody or FcRn-binding fragment thereof and isolating said antibody or fragment, wherein
the heavy chain comprises three CDRs, wherein CDR H1 has the sequence given in SEQ ID NO: 1, CDR H2 has the sequence given in SEQ ID NO: 2, and CDR H3 has the sequence given in SEQ ID NO: 3, and
the light chain comprises three CDRs, wherein CDR L1 has the sequence given in SEQ ID NO: 4, CDR L2 has the sequence given in SEQ ID NO: 5 or SEQ ID NO: 7 and CDR L3 has the sequence given in SEQ ID NO: 6.

39. The process of claim 38, wherein the antibody is humanized.

40. The process of claim 38, wherein the heavy chain comprises the sequence given in SEQ ID NO: 25 and the light chain comprises the sequence given in SEQ ID NO: 16.

41. The process of claim 38, wherein the heavy chain comprises a sequence having at least 80% identity to the sequence given in SEQ ID NO: 25 and wherein the light chain comprises a sequence having at least 80% identity to the sequence given in SEQ ID NO: 16.

42. The process of claim 38, wherein the FcRn-binding fragment is a scFv, Fv, Fab or Fab' fragment.

43. The process of claim 42, wherein the FcRn-binding fragment is a Fab' fragment having a heavy chain comprising the sequence given in SEQ ID NO: 33 and a light chain comprising the sequence given in SEQ ID NO: 20.

44. The process of claim 42, wherein the FcRn-binding fragment is a Fab fragment having a heavy chain comprising the sequence given in SEQ ID NO: 29 and a light chain comprising the sequence given in SEQ ID NO: 20.

45. The process of claim 38, wherein vector or pair of vectors encode a Fab-dsFv having a heavy chain comprising the sequence given in SEQ ID NO: 42 and a light chain comprising the sequence given in SEQ ID NO: 40.

46. The process of claim 38, wherein the anti-FcRn antibody is a full length antibody.

47. The process of claim 46, wherein the full length antibody is selected from the group consisting of an IgG1, IgG4 and IgG4P.

48. The process of claim 47, wherein the anti-FcRn antibody has a heavy chain comprising the sequence given in SEQ ID NO: 37, SEQ ID NO:39 or SEQ ID NO:73 and a light chain comprising the sequence given in SEQ ID NO: 20.

49. The isolated DNA molecule or pair of isolated DNA molecules according to claim 1, wherein the sequence encoding the heavy chain comprises the sequence given in SEQ ID NO: 26 and the sequence encoding the light chain comprises the sequence given in SEQ ID NO: 17.

50. The cloning or expression vector or pair of cloning or expression vectors according to claim 15, wherein the sequence encoding the heavy chain comprises the sequence given in SEQ ID NO: 26 and the sequence encoding the light chain comprises the sequence given in SEQ ID NO: 17.

51. The host cell according to claim 27, wherein the sequence encoding the heavy chain comprises the sequence given in SEQ ID NO: 26 and the sequence encoding the light chain comprises the sequence given in SEQ ID NO: 17.

52. The process of claim 38, wherein the sequence encoding the heavy chain comprises the sequence given in SEQ ID NO: 26 and the sequence encoding the light chain comprises the sequence given in SEQ ID NO: 17.

* * * * *

SEQUENCE LISTING

```
<160> NUMBER OF SEQ ID NOS: 74

<210> SEQ ID NO 1
<211> LENGTH: 12
<212> TYPE: PRT
<213> ORGANISM: Artificial Sequence
<220> FEATURE:
<223> OTHER INFORMATION: CDRH1

<400> SEQUENCE: 1

Gly Phe Ser Leu Ser Thr Tyr Gly Val Gly Val Gly
1               5                   10

<210> SEQ ID NO 2
<211> LENGTH: 16
<212> TYPE: PRT
<213> ORGANISM: Artificial Sequence
<220> FEATURE:
<223> OTHER INFORMATION: CDRH2

<400> SEQUENCE: 2

Asn Ile Trp Trp Asp Asp Asp Lys Arg Tyr Asn Pro Ser Leu Glu Asn
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: CDRH3

<400> SEQUENCE: 3

Thr Pro Ala Tyr Tyr Gly Ser His Pro Pro Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDRL1

<400> SEQUENCE: 4
```

Arg Thr Ser Glu Asp Ile Tyr Thr Asn Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDRL2

<400> SEQUENCE: 5

Val Ala Lys Thr Leu Gln Asp
1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3

<400> SEQUENCE: 6

Leu Gln Gly Phe Lys Phe Pro Trp Thr
1               5

<210> SEQ ID NO 7
<211> LENGTH: 7
<212> TYPE: PRT
<213> ORGANISM: Artificial Sequence
<220> FEATURE:
<223> OTHER INFORMATION: CDRL2 VARIANT

<400> SEQUENCE: 7

Val Ala Lys Thr Leu Gln Glu
1               5

<210> SEQ ID NO 8
<211> LENGTH: 107
<212> TYPE: PRT
<213> ORGANISM: Artificial Sequence
<220> FEATURE:
<223> OTHER INFORMATION: Rat Ab 1638 VL region

<400> SEQUENCE: 8

Asp Ile Leu Met Thr Gln Ser Pro Ala Ser Leu Ser Ala Ser Leu Gly
1               5                   10                  15

Glu Thr Ile Ser Ile Glu Cys Arg Thr Ser Glu Asp Ile Tyr Thr Asn
            20                  25                  30

Leu Ala Trp Tyr Gln Gln Lys Ser Gly Lys Ser Pro Gln Leu Leu Ile
        35                  40                  45

Tyr Val Ala Lys Thr Leu Gln Asp Gly Val Pro Ser Arg Phe Ser Gly
    50                  55                  60

Ser Gly Ser Gly Thr His Tyr Ser Leu Lys Ile Ser Gly Met Gln Pro
65                  70                  75                  80

Glu Asp Glu Gly Asp Tyr Phe Cys Leu Gln Gly Phe Lys Phe Pro Trp
                85                  90                  95

Thr Phe Gly Gly Gly Thr Lys Leu Glu Leu Lys
            100                 105

<210> SEQ ID NO 9
<211> LENGTH: 321
<212> TYPE: DNA
<213> ORGANISM: Artificial Sequence
<220> FEATURE:

<223> OTHER INFORMATION: Rat Ab 1638 VL region

<400> SEQUENCE: 9

```
gacatcctga tgacacagtc tccagcttcc ctgtctgcat ctctgggaga aactatctcc      60
atcgaatgtc gaacaagtga agacatttac actaatttag cgtggtacca gcagaagtca     120
gggaaatctc ctcaactcct gatctatgtt gcaaagacgt tgcaagatgg ggtcccatca     180
cggttcagtg gcagtggatc tggcacgcat tattctctca agatcagcgg catgcaacct     240
gaagatgaag gggattattt ctgtctgcag ggtttcaagt ttccgtggac gttcggtgga     300
ggcaccaagc tggaactgaa a                                               321
```

<210> SEQ ID NO 10
<211> LENGTH: 127
<212> TYPE: PRT
<213> ORGANISM: Artificial Sequence
<220> FEATURE:
<223> OTHER INFORMATION: Rat Ab 1638 VL region with signal sequence underlined and italicised

<400> SEQUENCE: 10

```
Met Asn Val Pro Thr Gln Phe Leu Gly Leu Leu Leu Leu Trp Ile Thr
 1               5                  10                  15

Asp Gly Ile Cys Asp Ile Leu Met Thr Gln Ser Pro Ala Ser Leu Ser
            20                  25                  30

Ala Ser Leu Gly Glu Thr Ile Ser Ile Glu Cys Arg Thr Ser Glu Asp
        35                  40                  45

Ile Tyr Thr Asn Leu Ala Trp Tyr Gln Gln Lys Ser Gly Lys Ser Pro
    50                  55                  60

Gln Leu Leu Ile Tyr Val Ala Lys Thr Leu Gln Asp Gly Val Pro Ser
65                  70                  75                  80

Arg Phe Ser Gly Ser Gly Ser Gly Thr His Tyr Ser Leu Lys Ile Ser
                85                  90                  95

Gly Met Gln Pro Glu Asp Glu Gly Asp Tyr Phe Cys Leu Gln Gly Phe
            100                 105                 110

Lys Phe Pro Trp Thr Phe Gly Gly Gly Thr Lys Leu Glu Leu Lys
        115                 120                 125
```

<210> SEQ ID NO 11
<211> LENGTH: 381
<212> TYPE: DNA
<213> ORGANISM: Artificial Sequence
<220> FEATURE:
<223> OTHER INFORMATION: Rat Ab 1638 VL region with signal sequence underlined and italicised

<400> SEQUENCE: 11

```
atgaatgtgc ccactcaatt ccttgggttg ttgctgctgt ggataacaga tggcatatgc      60
gacatcctga tgacacagtc tccagcttcc ctgtctgcat ctctgggaga aactatctcc     120
atcgaatgtc gaacaagtga agacatttac actaatttag cgtggtacca gcagaagtca     180
gggaaatctc ctcaactcct gatctatgtt gcaaagacgt tgcaagatgg ggtcccatca     240
cggttcagtg gcagtggatc tggcacgcat tattctctca agatcagcgg catgcaacct     300
gaagatgaag gggattattt ctgtctgcag ggtttcaagt ttccgtggac gttcggtgga     360
ggcaccaagc tggaactgaa a                                               381
```

<210> SEQ ID NO 12
<211> LENGTH: 122

<212> TYPE: PRT
<213> ORGANISM: Artificial Sequence
<220> FEATURE:
<223> OTHER INFORMATION: Rat Ab 1638 VH region

<400> SEQUENCE: 12

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Tyr
            20                  25                  30

Gly Val Gly Val Gly Trp Ile Arg Gln Pro Ser Gly Lys Gly Leu Glu
        35                  40                  45

Trp Leu Ala Asn Ile Trp Trp Asp Asp Lys Arg Tyr Asn Pro Ser
    50                  55                  60

Leu Glu Asn Arg Leu Thr Ile Ser Lys Asp Thr Ser Asn Asn Gln Ala
65                  70                  75                  80

Phe Leu Lys Ile Thr Asn Val Asp Thr Ala Asp Ser Ala Thr Tyr Phe
                85                  90                  95

Cys Val Arg Thr Pro Ala Tyr Tyr Gly Ser His Pro Pro Phe Asp Tyr
            100                 105                 110

Trp Gly Gln Gly Val Met Val Thr Val Ser
        115                 120

<210> SEQ ID NO 13
<211> LENGTH: 366
<212> TYPE: DNA
<213> ORGANISM: Artificial Sequence
<220> FEATURE:
<223> OTHER INFORMATION: Rat Ab 1638 VH region

<400> SEQUENCE: 13
caggttactc tgaaagagtc tggccctggg atattgcagc cctcccagac cctcagtctg      60
acttgcactt tctctgggtt ttcactgagt acttatggtg tgggtgtggg ctggattcgt     120
cagccttcag ggaagggtct ggagtggctg gcaaacattt ggtgggatga tgataagcgc     180
tacaatccat ctctggaaaa ccgactcact atctccaagg acacctccaa caaccaagca     240
ttcctcaaga tcaccaatgt ggacactgca gatagcgcca catacttctg tgttcggacc     300
ccggcttact atggcagcca tccccctttt gactactggg ccaaggagt catggtcaca     360
gtctcg                                                                366

<210> SEQ ID NO 14
<211> LENGTH: 141
<212> TYPE: PRT
<213> ORGANISM: Artificial Sequence
<220> FEATURE:
<223> OTHER INFORMATION: Rat Ab 1638 VH region with signal sequence
      underlined and italicised

<400> SEQUENCE: 14

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Thr Phe Ser Gly Phe Ser Leu
        35                  40                  45

Ser Thr Tyr Gly Val Gly Val Gly Trp Ile Arg Gln Pro Ser Gly Lys
    50                  55                  60

Gly Leu Glu Trp Leu Ala Asn Ile Trp Trp Asp Asp Lys Arg Tyr

```
                    65                  70                  75                  80
Asn Pro Ser Leu Glu Asn Arg Leu Thr Ile Ser Lys Asp Thr Ser Asn
                85                  90                  95

Asn Gln Ala Phe Leu Lys Ile Thr Asn Val Asp Thr Ala Asp Ser Ala
            100                 105                 110

Thr Tyr Phe Cys Val Arg Thr Pro Ala Tyr Tyr Gly Ser His Pro Pro
        115                 120                 125

Phe Asp Tyr Trp Gly Gln Gly Val Met Val Thr Val Ser
    130                 135                 140
```

<210> SEQ ID NO 15
<211> LENGTH: 423
<212> TYPE: DNA
<213> ORGANISM: Artificial Sequence
<220> FEATURE:
<223> OTHER INFORMATION: Rat Ab 1638 VH region with signal sequence
      underlined and italicised

<400> SEQUENCE: 15

```
atggacaggc taacttcctc attcctactg ctgattgtcc ctgcatatgt cctgtctcag     60
gttactctga aagagtctgg ccctgggata ttgcagccct cccagaccct cagtctgact    120
tgcactttct ctgggttttc actgagtact tatggtgtgg gtgtgggctg gattcgtcag    180
ccttcaggga agggtctgga gtggctggca aacatttggt gggatgatga taagcgctac    240
aatccatctc tggaaaaccg actcactatc tccaaggaca cctccaacaa ccaagcattc    300
ctcaagatca ccaatgtgga cactgcagat agcgccacat acttctgtgt cggaccccg     360
gcttactatg gcagccatcc cccttttgac tactggggcc aaggagtcat ggtcacagtc    420
tcg                                                                   423
```

<210> SEQ ID NO 16
<211> LENGTH: 107
<212> TYPE: PRT
<213> ORGANISM: Artificial Sequence
<220> FEATURE:
<223> OTHER INFORMATION: 1638 gL7 V-region

<400> SEQUENCE: 16

```
Asp Ile Gln Met Thr Gln Ser Pro Ser Ser Leu Ser Ala Ser Val Gly
1               5                  10                  15

Asp Arg Val Thr Ile Thr Cys Arg Thr Ser Glu Asp Ile Tyr Thr Asn
                20                  25                  30

Leu Ala Trp Tyr Gln Gln Lys Pro Gly Lys Val Pro Lys Leu Leu Ile
            35                  40                  45

Tyr Val Ala Lys Thr Leu Gln Glu Gly Val Pro Ser Arg Phe Ser Gly
        50                  55                  60

Ser Gly Ser Gly Thr His Tyr Thr Leu Thr Ile Ser Ser Leu Gln Pro
65                  70                  75                  80

Glu Asp Val Ala Thr Tyr Tyr Cys Leu Gln Gly Phe Lys Phe Pro Trp
                85                  90                  95

Thr Phe Gly Gly Gly Thr Lys Val Glu Ile Lys
            100                 105
```

<210> SEQ ID NO 17
<211> LENGTH: 321
<212> TYPE: DNA
<213> ORGANISM: Artificial Sequence
<220> FEATURE:
<223> OTHER INFORMATION: 1638 gL7 V-region

<400> SEQUENCE: 17

```
gatatccaga tgacccagag tccaagcagt ctctccgcca gcgtaggcga tcgtgtgact      60
attacctgtc gcactagcga ggacatctac accaacctgg cgtggtatca gcagaaacca     120
ggcaaagtgc cgaaactgct gatctacgtc gcgaaaaccc tccaggaagg tgtaccgtct     180
cgcttttccg gctctggtag cggtactcac tacaccctga ccatctcttc cctccagccg     240
gaagatgttg ctacctacta ttgcctccag ggcttcaaat cccgtggac tttcggtggc      300
ggcacgaaag tggaaatcaa a                                                321
```

<210> SEQ ID NO 18
<211> LENGTH: 128
<212> TYPE: PRT
<213> ORGANISM: Artificial Sequence
<220> FEATURE:
<223> OTHER INFORMATION: 1638 gL7 V-region (E. coli expression)

<400> SEQUENCE: 18

```
Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Arg Thr Ser Glu
        35                  40                  45

Asp Ile Tyr Thr Asn Leu Ala Trp Tyr Gln Gln Lys Pro Gly Lys Val
    50                  55                  60

Pro Lys Leu Leu Ile Tyr Val Ala Lys Thr Leu Gln Glu Gly Val Pro
65                  70                  75                  80

Ser Arg Phe Ser Gly Ser Gly Ser Gly Thr His Tyr Thr Leu Thr Ile
                85                  90                  95

Ser Ser Leu Gln Pro Glu Asp Val Ala Thr Tyr Tyr Cys Leu Gln Gly
            100                 105                 110

Phe Lys Phe Pro Trp Thr Phe Gly Gly Gly Thr Lys Val Glu Ile Lys
        115                 120                 125
```

<210> SEQ ID NO 19
<211> LENGTH: 384
<212> TYPE: DNA
<213> ORGANISM: Artificial Sequence
<220> FEATURE:
<223> OTHER INFORMATION: 1638 gL7 V-region (E. coli expression)

<400> SEQUENCE: 19

```
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattaccT gtcgcactag cgaggacatc taccaaacc tggcgtggta tcagcagaaa      180
ccaggcaaag tgccgaaact gctgatctac gtcgcgaaaa ccctccagga aggtgtaccg     240
tctcgctttt ccggctctgg tagcggtact cactacaccc tgaccatctc ttccctccag     300
ccggaagatg ttgctaccta ctattgcctc cagggcttca aattcccgtg gactttcggt     360
ggcggcacga aagtggaaat caaa                                             384
```

<210> SEQ ID NO 20
<211> LENGTH: 214
<212> TYPE: PRT
<213> ORGANISM: Artificial Sequence
<220> FEATURE:

<223> OTHER INFORMATION: 1638 gL7 light chain (V + constant)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Tyr Thr Asn
            20                  25                  30

Leu Ala Trp Tyr Gln Gln Lys Pro Gly Lys Val Pro Lys Leu Leu Ile
        35                  40                  45

Tyr Val Ala Lys Thr Leu Gln Glu Gly Val Pro Ser Arg Phe Ser Gly
50                  55                  60

Ser Gly Ser Gly Thr His Tyr Thr Leu Thr Ile Ser Ser Leu Gln Pro
65                  70                  75                  80

Glu Asp Val Ala Thr Tyr Tyr Cys Leu Gln Gly Phe Lys Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 642
<212> TYPE: DNA
<213> ORGANISM: Artificial Sequence
<220> FEATURE:
<223> OTHER INFORMATION: 1638 gL7 light chain (V + constant, E. coli
      expression)

<400> SEQUENCE: 21
gatatccaga tgacccagag tccaagcagt ctctccgcca gcgtaggcga tcgtgtgact      60
attacctgtc gcactagcga ggacatctac accaacctgg cgtggtatca gcagaaacca    120
ggcaaagtgc cgaaactgct gatctacgtc gcgaaaaccc tccaggaagg tgtaccgtct    180
cgcttttccg gctctggtag cggtactcac tacaccctga ccatctcttc cctccagccg    240
gaagatgttg ctacctacta ttgcctccag ggcttcaaat tcccgtggac tttcggtggc    300
ggcacgaaag tggaaatcaa acgtacggta gcggccccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcac cagtaacaaa aagttttaat agaggggagt gt                      642

<210> SEQ ID NO 22
<211> LENGTH: 642
<212> TYPE: DNA
<213> ORGANISM: Artificial Sequence
<220> FEATURE:
<223> OTHER INFORMATION: 1638 gL7 light chain (V + constant, mammalian expression)

<400> SEQUENCE: 22

```
gatatccaga tgacccagag tccaagcagt ctctccgcca gcgtaggcga tcgtgtgact    60
attacctgtc gcactagcga ggacatctac accaacctgg cgtggtatca gcagaaacca   120
ggcaaagtgc cgaaactgct gatctacgtc gcgaaacccc tccaggaagg tgtaccgtct   180
cgcttttccg gctctggtag cggtactcac tacaccctga ccatctcttc cctccagccg   240
gaagatgttg ctacctacta ttgcctccag ggcttcaaat tcccgtggac tttcggtggc   300
ggcacgaaag tggaaatcaa acggaccgtg gccgctccct ccgtgttcat cttcccaccc   360
tccgacgagc agctgaagtc cggcaccgcc tccgtcgtgt gcctgctgaa caacttctac   420
ccccgcgagg ccaaggtgca gtggaaggtg gacaacgccc tgcagtccgg caactcccag   480
gaatccgtca ccgagcagga ctccaaggac agcacctact ccctgtcctc caccctgacc   540
ctgtccaagg ccgactacga gaagcacaag gtgtacgcct gcgaagtgac ccaccagggc   600
ctgtccagcc ccgtgaccaa gtccttcaac cggggcgagt gc                      642
```

<210> SEQ ID NO 23
<211> LENGTH: 235
<212> TYPE: PRT
<213> ORGANISM: Artificial Sequence
<220> FEATURE:
<223> OTHER INFORMATION: 1638 gL7 light chain (E. coli expression)

<400> SEQUENCE: 23

Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Arg Thr Ser Glu
        35                  40                  45

Asp Ile Tyr Thr Asn Leu Ala Trp Tyr Gln Gln Lys Pro Gly Lys Val
    50                  55                  60

Pro Lys Leu Leu Ile Tyr Val Ala Lys Thr Leu Gln Glu Gly Val Pro
65                  70                  75                  80

Ser Arg Phe Ser Gly Ser Gly Ser Gly Thr His Tyr Thr Leu Thr Ile
                85                  90                  95

Ser Ser Leu Gln Pro Glu Asp Val Ala Thr Tyr Tyr Cys Leu Gln Gly
            100                 105                 110

Phe Lys Phe Pro Trp Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 24
<211> LENGTH: 705
<212> TYPE: DNA
<213> ORGANISM: Artificial Sequence
<220> FEATURE:
<223> OTHER INFORMATION: 1638 gL7 light chain (E. coli expression)

<400> SEQUENCE: 24

```
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtcgcactag cgaggacatc tacaccaacc tggcgtggta tcagcagaaa     180
ccaggcaaag tgccgaaact gctgatctac gtcgcgaaaa ccctccagga aggtgtaccg     240
tctcgctttt ccggctctgg tagcggtact cactacaccc tgaccatctc ttccctccag     300
ccggaagatg ttgctaccta ctattgcctc cagggcttca aattcccgtg gactttcggt     360
ggcggcacga aagtggaaat caaacgtacg gtagcggccc catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcccctg      600
acgctgagca agcagactac cgagaaacac aaagtctacg cctgcgaagt cacccatcag     660
ggcctgagct caccagtaac aaaaagtttt aatagagggg agtgt                     705
```

<210> SEQ ID NO 25
<211> LENGTH: 122
<212> TYPE: PRT
<213> ORGANISM: Artificial Sequence
<220> FEATURE:
<223> OTHER INFORMATION: 1638 gH33 V-region

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Gly Val Gly Val Gly Trp Val Arg Gln Ala Pro Gly Lys Gly Leu Glu
        35                  40                  45

Trp Leu Ala Asn Ile Trp Trp Asp Asp Lys Arg Tyr Asn Pro Ser
    50                  55                  60

Leu Glu Asn Arg Phe Thr Ile Ser Arg Asp Asn Ala Lys Asn Ser Ala
65                  70                  75                  80

Tyr Leu Gln Met Asn Ser Leu Arg Ala Glu Asp Thr Ala Val Tyr Tyr
                85                  90                  95

Cys Ala Arg Thr Pro Ala Tyr Tyr Gly Ser His Pro Pro Phe Asp Tyr
            100                 105                 110

Trp Gly Gln Gly Thr Met Val Thr Val Ser
        115                 120

<210> SEQ ID NO 26

<211> LENGTH: 366
<212> TYPE: DNA
<213> ORGANISM: Artificial Sequence
<220> FEATURE:
<223> OTHER INFORMATION: 1638 gH33 V-region

<400> SEQUENCE: 26

```
gaggttcagc tggtcgagtc tggaggcggg cttgtccagc ctggaggag cctgcgtctc      60
tcttgtgcag cgtccggctt ctctctgtct acctacggcg ttggtgttgg ttgggtacgt    120
caggctccag gtaaaggtct ggaatggctc gcaaacatct ggtgggacga cgataaacgc    180
tacaacccgt ccctggagaa ccgcttcacc attagccgtg ataacgcgaa aaactccgcg    240
tatctccaga tgaactccct gcgtgccgaa gacacggctg tgtactattg cgcgcgcact    300
ccggcgtact atggctctca cccaccgttt gattactggg gtcagggtac aatggttacc    360
gtctcg                                                                366
```

<210> SEQ ID NO 27
<211> LENGTH: 143
<212> TYPE: PRT
<213> ORGANISM: Artificial Sequence
<220> FEATURE:
<223> OTHER INFORMATION: 1638 gH33 V-region (E. coli expression)

<400> SEQUENCE: 27

```
Met Lys Lys Thr Ala Ile Ala Ile Ala Val Ala Leu Ala Gly Phe Ala
 1               5                  10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Ser Leu Ser Thr Tyr Gly Val Gly Val Gly Trp Val Arg Gln Ala Pro
    50                  55                  60

Gly Lys Gly Leu Glu Trp Leu Ala Asn Ile Trp Trp Asp Asp Asp Lys
65                  70                  75                  80

Arg Tyr Asn Pro Ser Leu Glu Asn Arg Phe Thr Ile Ser Arg Asp Asn
                85                  90                  95

Ala Lys Asn Ser Ala Tyr Leu Gln Met Asn Ser Leu Arg Ala Glu Asp
            100                 105                 110

Thr Ala Val Tyr Tyr Cys Ala Arg Thr Pro Ala Tyr Tyr Gly Ser His
        115                 120                 125

Pro Pro Phe Asp Tyr Trp Gly Gln Gly Thr Met Val Thr Val Ser
    130                 135                 140
```

<210> SEQ ID NO 28
<211> LENGTH: 429
<212> TYPE: DNA
<213> ORGANISM: Artificial Sequence
<220> FEATURE:
<223> OTHER INFORMATION: 1638 gH33 V-region (E.coli expression)

<400> SEQUENCE: 28

```
atgaagaaga ctgctatagc aattgcagtg gcgctagctg gtttcgccac cgtggcgcaa      60
gctgaggttc agctggtcga gtctggaggc gggcttgtcc agcctggagg agcctgcgt     120
ctctcttgtg cagcgtccgg cttctctctg tctacctacg gcgttggtgt tggttgggta    180
cgtcaggctc caggtaaagg tctggaatgg ctcgcaaaca tctggtggga cgacgataaa    240
cgctacaacc cgtccctgga gaaccgcttc accattagcc gtgataacgc gaaaaactcc    300
```

```
gcgtatctcc agatgaactc cctgcgtgcc gaagacacgg ctgtgtacta ttgcgcgcgc    360
actccggcgt actatggctc tcacccaccg tttgattact ggggtcaggg taccatggtt    420
accgtctcg                                                            429
```

<210> SEQ ID NO 29
<211> LENGTH: 226
<212> TYPE: PRT
<213> ORGANISM: Artificial Sequence
<220> FEATURE:
<223> OTHER INFORMATION: 1638 gH33 Fab heavy chain (V + human gamma-1 CH1)

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Gly Val Gly Val Gly Trp Val Arg Gln Ala Pro Gly Lys Gly Leu Glu
        35                  40                  45

Trp Leu Ala Asn Ile Trp Trp Asp Asp Lys Arg Tyr Asn Pro Ser
    50                  55                  60

Leu Glu Asn Arg Phe Thr Ile Ser Arg Asp Asn Ala Lys Asn Ser Ala
65                  70                  75                  80

Tyr Leu Gln Met Asn Ser Leu Arg Ala Glu Asp Thr Ala Val Tyr Tyr
                85                  90                  95

Cys Ala Arg Thr Pro Ala Tyr Tyr Gly Ser His Pro Pro Phe Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225
```

<210> SEQ ID NO 30
<211> LENGTH: 678
<212> TYPE: DNA
<213> ORGANISM: Artificial Sequence
<220> FEATURE:
<223> OTHER INFORMATION: 1638 gH33 Fab heavy chain (V + human gamma-1 CH1)

<400> SEQUENCE: 30

```
gaggttcagc tggtcgagtc tggaggcggg cttgtccagc ctggagggag cctgcgtctc    60
tcttgtgcag cgtccggctt ctctctgtct acctacggcg ttggtgttgg ttgggtacgt    120
caggctccag gtaaaggtct ggaatggctc gcaaacatct ggtgggacga cgataaacgc    180
```

```
tacaacccgt ccctggagaa ccgcttcacc attagccgtg ataacgcgaa aaactccgcg    240
tatctccaga tgaactccct gcgtgccgaa gacacggctg tgtactattg cgcgcgcact    300
ccggcgtact atggctctca cccaccgttt gattactggg gtcagggtac catggttacc    360
gtctcgagcg cttctacaaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt cgacaagaaa    660
gttgagccca aatcttgt                                                  678
```

<210> SEQ ID NO 31
<211> LENGTH: 247
<212> TYPE: PRT
<213> ORGANISM: Artificial Sequence
<220> FEATURE:
<223> OTHER INFORMATION: 1638 gH33 Fab heavy chain with (E. coli expression)

<400> SEQUENCE: 31

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Ser Leu Ser Thr Tyr Gly Val Gly Val Gly Trp Val Arg Gln Ala Pro
    50                  55                  60

Gly Lys Gly Leu Glu Trp Leu Ala Asn Ile Trp Trp Asp Asp Asp Lys
65                  70                  75                  80

Arg Tyr Asn Pro Ser Leu Glu Asn Arg Phe Thr Ile Ser Arg Asp Asn
                85                  90                  95

Ala Lys Asn Ser Ala Tyr Leu Gln Met Asn Ser Leu Arg Ala Glu Asp
            100                 105                 110

Thr Ala Val Tyr Tyr Cys Ala Arg Thr Pro Ala Tyr Tyr Gly Ser His
        115                 120                 125

Pro Pro Phe Asp Tyr Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys
                245
```

<210> SEQ ID NO 32

<211> LENGTH: 741
<212> TYPE: DNA
<213> ORGANISM: Artificial Sequence
<220> FEATURE:
<223> OTHER INFORMATION: 1638 gH33 Fab heavy chain (E. coli expression)

<400> SEQUENCE: 32

```
atgaagaaga ctgctatagc aattgcagtg gcgctagctg gtttcgccac cgtggcgcaa      60
gctgaggttc agctggtcga gtctggaggc gggcttgtcc agcctggagg gagcctgcgt     120
ctctcttgtg cagcgtccgg cttctctctg tctacctacg gcgttggtgt tggttgggta     180
cgtcaggctc caggtaaagg tctggaatgg ctcgcaaaca tctggtggga cgacgataaa     240
cgctacaacc cgtccctgga gaaccgcttc accattagcc gtgataacgc gaaaaactcc     300
gcgtatctcc agatgaactc cctgcgtgcc gaagacacgg ctgtgtacta ttgcgcgcgc     360
actccggcgt actatggctc tcacccaccg tttgattact ggggtcaggg taccatggtt     420
accgtctcga gcgcttctac aaagggccca tcggtcttcc ccctggcacc ctcctccaag     480
agcacctctg gggcacagc ggccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc cagcagcttg     660
ggcacccaga cctacatctg caacgtgaat cacaagccca gcaacaccaa ggtcgacaag     720
aaagttgagc ccaaatcttg t                                                741
```

<210> SEQ ID NO 33
<211> LENGTH: 234
<212> TYPE: PRT
<213> ORGANISM: Artificial Sequence
<220> FEATURE:
<223> OTHER INFORMATION: 1638 gH33 Fab' heavy chain (V + human gamma-1
      CH1 + hinge)

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Gly Val Gly Val Gly Trp Val Arg Gln Ala Pro Gly Lys Gly Leu Glu
        35                  40                  45

Trp Leu Ala Asn Ile Trp Trp Asp Asp Lys Arg Tyr Asn Pro Ser
    50                  55                  60

Leu Glu Asn Arg Phe Thr Ile Ser Arg Asp Asn Ala Lys Asn Ser Ala
65                  70                  75                  80

Tyr Leu Gln Met Asn Ser Leu Arg Ala Glu Asp Thr Ala Val Tyr Tyr
                85                  90                  95

Cys Ala Arg Thr Pro Ala Tyr Tyr Gly Ser His Pro Pro Phe Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                180               185                190
Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
        210                 215                 220

Ser Cys Asp Lys Thr His Thr Cys Ala Ala
225                 230
```

```
<210> SEQ ID NO 34
<211> LENGTH: 702
<212> TYPE: DNA
<213> ORGANISM: Artificial Sequence
<220> FEATURE:
<223> OTHER INFORMATION: 1638 gH33 Fab' heavy chain (V + human gamma-1
      CH1 + hinge)

<400> SEQUENCE: 34
```

```
gaggttcagc tggtcgagtc tggaggcggg cttgtccagc ctggagggag cctgcgtctc      60
tcttgtgcag cgtccggctt ctctctgtct acctacggcg ttggtgttgg ttgggtacgt     120
caggctccag gtaaaggtct ggaatggctc gcaaacatct ggtgggacga cgataaacgc     180
tacaacccgt ccctggagaa ccgcttcacc attagccgtg ataacgcgaa aaactccgcg     240
tatctccaga tgaactccct gcgtgccgaa gacacggctg tgtactattg cgcgcgcact     300
ccggcgtact atggctctca cccaccgttt gattactggg gtcagggtac catggttacc     360
gtctcgagcg cttctacaaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt cgacaagaaa     660
gttgagccca atcttgtga caaaactcac acatgcgccg cg                         702
```

```
<210> SEQ ID NO 35
<211> LENGTH: 255
<212> TYPE: PRT
<213> ORGANISM: Artificial Sequence
<220> FEATURE:
<223> OTHER INFORMATION: 1638 gH33 Fab' heavy chain (E. coli expression)

<400> SEQUENCE: 35
```

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Ser Leu Ser Thr Tyr Gly Val Gly Val Gly Trp Val Arg Gln Ala Pro
    50                  55                  60

Gly Lys Gly Leu Glu Trp Leu Ala Asn Ile Trp Trp Asp Asp Asp Lys
65                  70                  75                  80

Arg Tyr Asn Pro Ser Leu Glu Asn Arg Phe Thr Ile Ser Arg Asp Asn
                85                  90                  95

Ala Lys Asn Ser Ala Tyr Leu Gln Met Asn Ser Leu Arg Ala Glu Asp
            100                 105                 110

Thr Ala Val Tyr Tyr Cys Ala Arg Thr Pro Ala Tyr Tyr Gly Ser His
        115                 120                 125
```

```
Pro Pro Phe Asp Tyr Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Ala Ala
                245                 250                 255
```

<210> SEQ ID NO 36
<211> LENGTH: 765
<212> TYPE: DNA
<213> ORGANISM: Artificial Sequence
<220> FEATURE:
<223> OTHER INFORMATION: 1638 gH33 Fab' heavy chain (E. coli expression)

<400> SEQUENCE: 36

```
atgaagaaga ctgctatagc aattgcagtg gcgctagctg gtttcgccac cgtggcgcaa    60
gctgaggttc agctggtcga gtctggaggc gggcttgtcc agcctggagg gagcctgcgt   120
ctctcttgtg cagcgtccgg cttctctctg tctacctacg gcgttggtgt tggttgggta   180
cgtcaggctc caggtaaagg tctggaatgg ctcgcaaaca tctggtggga cgacgataaa   240
cgctacaacc cgtccctgga gaaccgcttc accattagcc gtgataacgc gaaaaactcc   300
gcgtatctcc agatgaactc cctgcgtgcc gaagacacgg ctgtgtacta ttgcgcgcgc   360
actccggcgt actatggctc tcacccaccg tttgattact ggggtcaggg taccatggtt   420
accgtctcga gcgcttctac aaagggccca tcggtcttcc cctggcacc ctcctccaag    480 agcacctctg gggcacagc ggccctgggc tgcctggtca aggactactt ccccgaaccg   540
gtgacggtgt cgtggaactc aggcgccctg accagcggcg tgcacacctt cccggctgtc   600
ctacagtcct caggactcta ctccctcagc agcgtggtga ccgtgccctc agcagcttg    660 ggcacccaga cctacatctg caacgtgaat cacaagccca gcaacaccaa ggtcgacaag   720
aaagttgagc ccaaatcttg tgacaaaact cacacatgcg ccgcg                   765
```

<210> SEQ ID NO 37
<211> LENGTH: 450
<212> TYPE: PRT
<213> ORGANISM: Artificial Sequence
<220> FEATURE:
<223> OTHER INFORMATION: 1638 gH33 IgG4 heavy chain (V + human gamma-4P
      constant)

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Gly Val Gly Val Gly Trp Val Arg Gln Ala Pro Gly Lys Gly Leu Glu
```

```
              35                  40                  45
Trp Leu Ala Asn Ile Trp Trp Asp Asp Lys Arg Tyr Asn Pro Ser
 50                  55                  60

Leu Glu Asn Arg Phe Thr Ile Ser Arg Asp Asn Ala Lys Asn Ser Ala
 65                  70                  75                  80

Tyr Leu Gln Met Asn Ser Leu Arg Ala Glu Asp Thr Ala Val Tyr Tyr
                 85                  90                  95

Cys Ala Arg Thr Pro Ala Tyr Tyr Gly Ser His Pro Pro Phe Asp Tyr
                100                 105                 110

Trp Gly Gln Gly Thr Met Val Thr Val Ser Ser Ala Ser Thr Lys Gly
                115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
450
```

<210> SEQ ID NO 38
<211> LENGTH: 1350
<212> TYPE: DNA
<213> ORGANISM: Artificial Sequence
<220> FEATURE:
<223> OTHER INFORMATION: 1638 gH33 IgG4 heavy chain (V + human gamma-4P constant)

<400> SEQUENCE: 38

```
gaggttcagc tggtcgagtc tggaggcggg cttgtccagc tggagggag cctgcgtctc      60
tcttgtgcag cgtccggctt ctctctgtct acctacggcg ttggtgttgg ttgggtacgt    120
caggctccag gtaaaggtct ggaatggctc gcaaacatct ggtgggacga cgataaacgc    180
tacaacccgt ccctggagaa ccgcttcacc attagccgtg ataacgcgaa aaactccgcg    240
tatctccaga tgaactccct gcgtgccgaa gacacggctg tgtactattg cgcgcgcact    300
ccggcgtact atggctctca cccaccgttt gattactggg gtcagggtac aatggttacc    360
gtctcgtctg cctccaccaa gggccccctcc gtgttccctc tggccccttg ctcccggtcc    420
acctccgagt ctaccgccgc tctgggctgc ctggtcaagg actacttccc cgagcccgtg    480
acagtgtcct ggaactctgg cgccctgacc tccggcgtgc acaccttccc tgccgtgctg    540
cagtcctccg gcctgtactc cctgtcctcc gtcgtgaccg tgccctcctc agcctgggc     600
accaagacct acacctgtaa cgtggaccac aagccctcca acaccaaggt ggacaagcgg    660
gtggaatcta agtacggccc tccctgcccc cctgccctg ccctgaattt ctgggcgga     720
ccttccgtgt tcctgttccc cccaaagccc aaggacaccc tgatgatctc ccggaccccc    780
gaagtgacct gcgtggtggt ggacgtgtcc aggaagatc ccgaggtcca gttcaattgg    840
tacgtggacg gcgtggaagt gcacaatgcc aagaccaagc ccagagagga acagttcaac    900
tccacctacc gggtggtgtc cgtgctgacc gtgctgcacc aggactggct gaacggcaaa    960
gagtacaagt gcaaggtgtc caacaagggc ctgccctcca gcatcgaaaa gaccatctcc   1020
aaggccaagg gccagccccg cgagcccag gtgtacaccc tgcccctag ccaggaagag   1080
atgaccaaga accaggtgtc cctgacctgt ctggtcaagg gcttctaccc ctccgacatt   1140
gccgtggaat gggagtccaa cggccagccc gagaacaact acaagaccac ccccctgtg   1200
ctggacagcg acggctcctt cttcctgtac tctcggctga ccgtggacaa gtcccggtgg   1260
caggaaggca acgtcttctc ctgctccgtg atgcacgagg ccctgcacaa ccactacacc   1320
cagaagtccc tgtccctgag cctgggcaag                                    1350
```

<210> SEQ ID NO 39
<211> LENGTH: 449
<212> TYPE: PRT
<213> ORGANISM: Artificial Sequence
<220> FEATURE:
<223> OTHER INFORMATION: 1638 gH33 IgG4 heavy chain (V + human gamma-4P constant mammalian, no c-terminal lys)

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Gly Val Gly Val Gly Trp Val Arg Gln Ala Pro Gly Lys Gly Leu Glu
        35                  40                  45

Trp Leu Ala Asn Ile Trp Trp Asp Asp Asp Lys Arg Tyr Asn Pro Ser
```

```
                50                  55                  60
Leu Glu Asn Arg Phe Thr Ile Ser Arg Asp Asn Ala Lys Asn Ser Ala
 65                  70                  75                  80

Tyr Leu Gln Met Asn Ser Leu Arg Ala Glu Asp Thr Ala Val Tyr Tyr
                 85                  90                  95

Cys Ala Arg Thr Pro Ala Tyr Tyr Gly Ser His Pro Pro Phe Asp Tyr
                100                 105                 110

Trp Gly Gln Gly Thr Met Val Thr Val Ser Ser Ala Ser Thr Lys Gly
                115                 120                 125

Pro Ser Val Phe Pro Leu Ala Pro Cys Ser Arg Ser Thr Ser Glu Ser
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly

<210> SEQ ID NO 40
<211> LENGTH: 341
```

```
<212> TYPE: PRT
<213> ORGANISM: Artificial Sequence
<220> FEATURE:
<223> OTHER INFORMATION: 1638 gL7 FabFv light chain

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Tyr Thr Asn
            20                  25                  30

Leu Ala Trp Tyr Gln Gln Lys Pro Gly Lys Val Pro Lys Leu Leu Ile
        35                  40                  45

Tyr Val Ala Lys Thr Leu Gln Glu Gly Val Pro Ser Arg Phe Ser Gly
    50                  55                  60

Ser Gly Ser Gly Thr His Tyr Thr Leu Thr Ile Ser Ser Leu Gln Pro
65                  70                  75                  80

Glu Asp Val Ala Thr Tyr Tyr Cys Leu Gln Gly Phe Lys Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Asp Ile Gln Met Thr Gln Ser Pro Ser Ser Val
225                 230                 235                 240

Ser Ala Ser Val Gly Asp Arg Val Thr Ile Thr Cys Gln Ser Ser Pro
                245                 250                 255

Ser Val Trp Ser Asn Phe Leu Ser Trp Tyr Gln Gln Lys Pro Gly Lys
            260                 265                 270

Ala Pro Lys Leu Leu Ile Tyr Glu Ala Ser Lys Leu Thr Ser Gly Val
        275                 280                 285

Pro Ser Arg Phe Ser Gly Ser Gly Ser Gly Thr Asp Phe Thr Leu Thr
290                 295                 300

Ile Ser Ser Leu Gln Pro Glu Asp Phe Ala Thr Tyr Tyr Cys Gly Gly
305                 310                 315                 320

Gly Tyr Ser Ser Ile Ser Asp Thr Thr Phe Gly Cys Gly Thr Lys Val
                325                 330                 335

Glu Ile Lys Arg Thr
            340

<210> SEQ ID NO 41
<211> LENGTH: 1023
<212> TYPE: DNA
<213> ORGANISM: Artificial Sequence
<220> FEATURE:
```

<223> OTHER INFORMATION: 1638 gL7 FabFv light chain

<400> SEQUENCE: 41

```
gatatccaga tgacccagag tccaagcagt ctctccgcca gcgtaggcga tcgtgtgact      60
attacctgtc gcactagcga ggacatctac accaacctgg cgtggtatca gcagaaacca     120
ggcaaagtgc cgaaactgct gatctacgtc gcgaaaaccc tccaggaagg tgtaccgtct     180
cgcttttccg gctctggtag cggtactcac tacaccctga ccatctcttc cctccagccg     240
gaagatgttg ctacctacta ttgcctccag ggcttcaaat tcccgtggac tttcggtggc     300
ggcacgaaag tggaaatcaa acgtacggta gcggccccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc     600
ctgagctcgc ccgtcacaaa gagcttcaac aggggagagt gtggtggagg tggctctggc     660
ggtggtggct ccggaggcgg aggaagcgac atccagatga cccagagccc ttcctctgta     720
agcgccagtg tcggagacag agtgactatt acctgccaaa gctcccttc agtctggtcc      780
aattttctat cctggtatca gcaaaagccc ggaaaggctc ctaaattgct gatctacgaa     840
gcaagcaaac tcaccagcgg cgtgcccagc aggttcagcg cagtgggtc tggaactgac      900
tttaccctga caatctcctc actccagccc gaggacttcg ccacctatta ctgcggtgga    960
ggttacagta gcataagtga tacgacattt ggatgcggca ctaaagtgga aatcaagcgt   1020
acc                                                                 1023
```

<210> SEQ ID NO 42
<211> LENGTH: 363
<212> TYPE: PRT
<213> ORGANISM: Artificial Sequence
<220> FEATURE:
<223> OTHER INFORMATION: 1638 gH33 FabFv heavy chain

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Gly Val Gly Val Gly Trp Val Arg Gln Ala Pro Gly Lys Gly Leu Glu
        35                  40                  45

Trp Leu Ala Asn Ile Trp Trp Asp Asp Lys Arg Tyr Asn Pro Ser
    50                  55                  60

Leu Glu Asn Arg Phe Thr Ile Ser Arg Asp Asn Ala Lys Asn Ser Ala
65                  70                  75                  80

Tyr Leu Gln Met Asn Ser Leu Arg Ala Glu Asp Thr Ala Val Tyr Tyr
                85                  90                  95

Cys Ala Arg Thr Pro Ala Tyr Tyr Gly Ser His Pro Pro Phe Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
            165                 170                 175
Pro Ala Val Leu Gln Ser Ser Gly Leu Tyr Ser Leu Ser Ser Val Val
        180                 185                 190
Thr Val Pro Ser Ser Ser Leu Gly Thr Gln Thr Tyr Ile Cys Asn Val
    195                 200                 205
Asn His Lys Pro Ser Asn Thr Lys Val Asp Lys Lys Val Glu Pro Lys
210                 215                 220
Ser Cys Ser Gly Gly Gly Gly Ser Gly Gly Gly Gly Thr Gly Gly Gly
225                 230                 235                 240
Gly Ser Glu Val Gln Leu Leu Glu Ser Gly Gly Gly Leu Val Gln Pro
            245                 250                 255
Gly Gly Ser Leu Arg Leu Ser Cys Ala Val Ser Gly Ile Asp Leu Ser
        260                 265                 270
Asn Tyr Ala Ile Asn Trp Val Arg Gln Ala Pro Gly Lys Cys Leu Glu
    275                 280                 285
Trp Ile Gly Ile Ile Trp Ala Ser Gly Thr Thr Phe Tyr Ala Thr Trp
290                 295                 300
Ala Lys Gly Arg Phe Thr Ile Ser Arg Asp Asn Ser Lys Asn Thr Val
305                 310                 315                 320
Tyr Leu Gln Met Asn Ser Leu Arg Ala Glu Asp Thr Ala Val Tyr Tyr
            325                 330                 335
Cys Ala Arg Thr Val Pro Gly Tyr Ser Thr Ala Pro Tyr Phe Asp Leu
        340                 345                 350
Trp Gly Gln Gly Thr Leu Val Thr Val Ser Ser
    355                 360

<210> SEQ ID NO 43
<211> LENGTH: 1089
<212> TYPE: DNA
<213> ORGANISM: Artificial Sequence
<220> FEATURE:
<223> OTHER INFORMATION: 1638 gH33 FabFv heavy chain

<400> SEQUENCE: 43
gaggttcagc tggtcgagtc tggaggcggg cttgtccagc ctggaggag cctgcgtctc      60 tcttgtgcag cgtccggctt ctctctgtct acctacggcg ttggtgttgg ttgggtacgt    120
caggctccag gtaaaggtct ggaatggctc gcaaacatct ggtgggacga cgataaacgc    180
tacaacccgt ccctggagaa ccgcttcacc attagccgtg ataacgcgaa aaactccgcg    240
tatctccaga tgaactccct gcgtgccgaa gacacggctg tgtactattg cgcgcgcact    300
ccggcgtact atggctctca cccaccgttt gattactggg gtcagggtac aatggttacc    360
gtctcgtccg cttctacaaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctctg gactctactc cctcagcagc gtggtgaccg tgccctccag cagcttgggc    600
acccagacct acatctgcaa cgtgaatcac aagcccagca acaccaaggt ggacaagaaa    660
gttgagccca atcttgttc ggaggtggc ggttccggag gtggcggtac aggtggcggt    720
gggtccgaag tccagctgct tgaatccgga ggcggactcg tgcagcccgg aggcagtctt    780
cgcttgtcct gcgctgtatc tggaatcgac ctgagcaatt acgccatcaa ctgggtgaga    840
caggcacctg ggaaatgcct cgaatggatc ggcattatat gggctagtgg gacgaccttt    900
```

| tatgctacat gggcgaaggg tagattcaca atctcacggg ataatagtaa gaacacagtg | 960 |
| tacctgcaga tgaactccct gcgagcagag ataccgccg tttactattg tgctcgcact | 1020 |
| gtcccaggtt atagcactgc accctacttt gatctgtggg gcagggcac tctggtcacc | 1080 |
| gtctcgtcc | 1089 |

<210> SEQ ID NO 44
<211> LENGTH: 107
<212> TYPE: PRT
<213> ORGANISM: Artificial Sequence
<220> FEATURE:
<223> OTHER INFORMATION: Human IGKV1-27 JK4 acceptor framework

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 45
<211> LENGTH: 321
<212> TYPE: DNA
<213> ORGANISM: Artificial Sequence
<220> FEATURE:
<223> OTHER INFORMATION: Human IGKV1-27 JK4 acceptor framework

<400> SEQUENCE: 45

| gacatccaga tgacccagtc tccatcctcc ctgtctgcat ctgtaggaga cagagtcacc | 60 |
| atcacttgcc gggcgagtca gggcattagc aattatttag cctggtatca gcagaaacca | 120 |
| gggaaagttc ctaagctcct gatctatgct gcatccactt tgcaatcagg ggtcccatct | 180 |
| cggttcagtg gcagtggatc tgggacagat ttcactctca ccatcagcag cctgcagcct | 240 |
| gaagatgttg caacttatta ctgtcaaaag tataacagtg cccctctcac tttcggcgga | 300 |
| gggaccaagg tggagatcaa a | 321 |

<210> SEQ ID NO 46
<211> LENGTH: 114
<212> TYPE: PRT
<213> ORGANISM: Artificial Sequence
<220> FEATURE:
<223> OTHER INFORMATION: Human IGHV3-7 JH3 acceptor framework

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val

```
                          35                  40                  45
Ala Asn Ile Lys Gln Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Phe Asp Val Trp Gly Gln Gly Thr Met Val Thr Val
            100                 105                 110

Ser Ser

<210> SEQ ID NO 47
<211> LENGTH: 342
<212> TYPE: DNA
<213> ORGANISM: Artificial Sequence
<220> FEATURE:
<223> OTHER INFORMATION: Human IGHV3-7 JH3 acceptor framework

<400> SEQUENCE: 47
gaggtgcagc tggtggagtc tgggggaggc ttggtccagc ctggggggtc cctgagactc      60
tcctgtgcag cctctggatt cacctttagt agctattgga tgagctgggt ccgccaggct     120
ccagggaagg ggctggagtg ggtggccaac ataaagcaag atggaagtga aaatactat      180 gtggactctg tgaagggccg attcaccatc tccagagaca cgccaagaa ctcactgtat      240 ctgcaaatga acagcctgag agccgaggac acggctgtgt attactgtgc gagagatgct     300
tttgatgtct ggggccaagg gacaatggtc accgtctctt ca                         342

<210> SEQ ID NO 48
<211> LENGTH: 274
<212> TYPE: PRT
<213> ORGANISM: Artificial Sequence
<220> FEATURE:
<223> OTHER INFORMATION: Human FcRn alpha chain extracellular sequence

<400> SEQUENCE: 48

Ala Glu Ser His Leu Ser Leu Leu Tyr His Leu Thr Ala Val Ser Ser
 1               5                  10                  15

Pro Ala Pro Gly Thr Pro Ala Phe Trp Val Ser Gly Trp Leu Gly Pro
             20                  25                  30

Gln Gln Tyr Leu Ser Tyr Asn Ser Leu Arg Gly Glu Ala Glu Pro Cys
         35                  40                  45

Gly Ala Trp Val Trp Glu Asn Gln Val Ser Trp Tyr Trp Glu Lys Glu
     50                  55                  60

Thr Thr Asp Leu Arg Ile Lys Glu Lys Leu Phe Leu Glu Ala Phe Lys
 65                  70                  75                  80

Ala Leu Gly Gly Lys Gly Pro Tyr Thr Leu Gln Gly Leu Leu Gly Cys
                 85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
```

165                 170                 175
Lys Glu Pro Pro Ser Met Arg Leu Lys Ala Arg Pro Ser Ser Pro Gly
                 180                 185                 190

Phe Ser Val Leu Thr Cys Ser Ala Phe Ser Phe Tyr Pro Pro Glu Leu
             195                 200                 205

Gln Leu Arg Phe Leu Arg Asn Gly Leu Ala Ala Gly Thr Gly Gln Gly
         210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
             245                 250                 255

Ala Gly Leu Ala Gln Pro Leu Arg Val Glu Leu Glu Ser Pro Ala Lys
         260                 265                 270

Ser Ser

<210> SEQ ID NO 49
<211> LENGTH: 99
<212> TYPE: PRT
<213> ORGANISM: Artificial Sequence
<220> FEATURE:
<223> OTHER INFORMATION: Rat ?2M

<400> SEQUENCE: 49

Ile Gln Lys Thr Pro Gln Ile Gln Val Tyr Ser Arg His Pro Pro Glu
1               5                   10                  15

Asn Gly Lys Pro Asn Phe Leu Asn Cys Tyr Val Ser Gln Phe His Pro
             20                  25                  30

Pro Gln Ile Glu Ile Glu Leu Leu Lys Asn Gly Lys Lys Ile Pro Asn
         35                  40                  45

Ile Glu Met Ser Asp Leu Ser Phe Ser Lys Asp Trp Ser Phe Tyr Ile
     50                  55                  60

Leu Ala His Thr Glu Phe Thr Pro Thr Glu Thr Asp Val Tyr Ala Cys
65                  70                  75                  80

Arg Val Lys His Val Thr Leu Lys Glu Pro Lys Thr Val Thr Trp Asp
                 85                  90                  95

Arg Asp Met

<210> SEQ ID NO 50
<211> LENGTH: 119
<212> TYPE: PRT
<213> ORGANISM: Artificial Sequence
<220> FEATURE:
<223> OTHER INFORMATION: Human ?2M including signal sequence

<400> SEQUENCE: 50

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
             20                  25                  30

His Pro Ala Glu Asn Gly Lys Ser Asn Phe Leu Asn Cys Tyr Val Ser
         35                  40                  45

Gly Phe His Pro Ser Asp Ile Glu Val Asp Leu Leu Lys Asn Gly Glu
     50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                 85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 51
<211> LENGTH: 107
<212> TYPE: PRT
<213> ORGANISM: Artificial Sequence
<220> FEATURE:
<223> OTHER INFORMATION: 1638gL2 V-region

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Tyr Thr Asn
            20                  25                  30

Leu Ala Trp Tyr Gln Gln Lys Pro Gly Lys Val Pro Lys Leu Leu Ile
        35                  40                  45

Tyr Val Ala Lys Thr Leu Gln Asp Gly Val Pro Ser Arg Phe Ser Gly
    50                  55                  60

Ser Gly Ser Gly Thr His Tyr Thr Leu Thr Ile Ser Ser Leu Gln Pro
65                  70                  75                  80

Glu Asp Val Ala Thr Tyr Tyr Cys Leu Gln Gly Phe Lys Phe Pro Trp
                85                  90                  95

Thr Phe Gly Gly Gly Thr Lys Val Glu Ile Lys
            100                 105

<210> SEQ ID NO 52
<211> LENGTH: 321
<212> TYPE: DNA
<213> ORGANISM: Artificial Sequence
<220> FEATURE:
<223> OTHER INFORMATION: 1638gL2 V-region

<400> SEQUENCE: 52
gatatccaga tgacccagag tccaagcagt ctctccgcca gcgtaggcga tcgtgtgact      60
attacctgtc gcactagcga ggacatctac accaacctgg cgtggtatca gcagaaacca     120
ggcaaagtgc cgaaactgct gatctacgtc gcgaaaaccc tccaggacgg tgtaccgtct     180
cgcttttccg gctctggtag cggtactcac tacaccctga ccatctcttc cctccagccg     240
gaagatgttg ctacctacta ttgcctccag ggcttcaaat tcccgtggac tttcggtggc     300
ggcacgaaag tggaaatcaa a                                               321

<210> SEQ ID NO 53
<211> LENGTH: 128
<212> TYPE: PRT
<213> ORGANISM: Artificial Sequence
<220> FEATURE:
<223> OTHER INFORMATION: 1638 gL2 V-region (E. coli expression)

<400> SEQUENCE: 53

Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Arg Thr Ser Glu
        35                  40                  45

```
Asp Ile Tyr Thr Asn Leu Ala Trp Tyr Gln Gln Lys Pro Gly Lys Val
 50                  55                  60

Pro Lys Leu Leu Ile Tyr Val Ala Lys Thr Leu Gln Asp Gly Val Pro
 65                  70                  75                  80

Ser Arg Phe Ser Gly Ser Gly Ser Gly Thr His Tyr Thr Leu Thr Ile
                 85                  90                  95

Ser Ser Leu Gln Pro Glu Asp Val Ala Thr Tyr Tyr Cys Leu Gln Gly
                100                 105                 110

Phe Lys Phe Pro Trp Thr Phe Gly Gly Gly Thr Lys Val Glu Ile Lys
                115                 120                 125

<210> SEQ ID NO 54
<211> LENGTH: 384
<212> TYPE: DNA
<213> ORGANISM: Artificial Sequence
<220> FEATURE:
<223> OTHER INFORMATION: 1638 gL2 V-region (E. coli expression)

<400> SEQUENCE: 54
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtcgcactag cgaggacatc tacaccaacc tggcgtggta tcagcagaaa     180
ccaggcaaag tgccgaaact gctgatctac gtcgcgaaaa ccctccagga cggtgtaccg     240
tctcgctttt ccggctctgg tagcggtact cactacaccc tgaccatctc ttccctccag     300
ccggaagatg ttgctaccta ctattgcctc cagggcttca aattcccgtg gactttcggt     360
ggcggcacga aagtggaaat caaa                                            384

<210> SEQ ID NO 55
<211> LENGTH: 214
<212> TYPE: PRT
<213> ORGANISM: Artificial Sequence
<220> FEATURE:
<223> OTHER INFORMATION: 1638 gL2 light chain (V + constant)

<400> SEQUENCE: 55

Asp Ile Gln Met Thr Gln Ser Pro Ser Ser Leu Ser Ala Ser Val Gly
  1               5                  10                  15

Asp Arg Val Thr Ile Thr Cys Arg Thr Ser Glu Asp Ile Tyr Thr Asn
                 20                  25                  30

Leu Ala Trp Tyr Gln Gln Lys Pro Gly Lys Val Pro Lys Leu Leu Ile
             35                  40                  45

Tyr Val Ala Lys Thr Leu Gln Asp Gly Val Pro Ser Arg Phe Ser Gly
 50                  55                  60

Ser Gly Ser Gly Thr His Tyr Thr Leu Thr Ile Ser Ser Leu Gln Pro
 65                  70                  75                  80

Glu Asp Val Ala Thr Tyr Tyr Cys Leu Gln Gly Phe Lys Phe Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 56
<211> LENGTH: 642
<212> TYPE: DNA
<213> ORGANISM: Artificial Sequence
<220> FEATURE:
<223> OTHER INFORMATION: 1638 gL2 light chain (V + constant, codon
      optimized for E. coli expression)

<400> SEQUENCE: 56

```
gatatccaga tgacccagag tccaagcagt ctctccgcca gcgtaggcga tcgtgtgact    60
attacctgtc gcactagcga ggacatctac accaacctgg cgtggtatca gcagaaacca   120
ggcaaagtgc cgaaactgct gatctacgtc gcgaaaaccc tccaggacgg tgtaccgtct   180
cgcttttccg gctctggtag cggtactcac tacaccctga ccatctcttc cctccagccg   240
gaagatgttg ctacctacta ttgcctccag ggcttcaaat tcccgtggac tttcggtggc   300
ggcacgaaag tggaaatcaa acgtacggta gcggccccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcac cagtaacaaa aagtttttaat agaggggagt gt                     642
```

<210> SEQ ID NO 57
<211> LENGTH: 235
<212> TYPE: PRT
<213> ORGANISM: Artificial Sequence
<220> FEATURE:
<223> OTHER INFORMATION: 1638 gL2 light chain (E. coli expression)

<400> SEQUENCE: 57

```
Met Lys Lys Thr Ala Ile Ala Ile Ala Val Ala Leu Ala Gly Phe Ala
1               5                   10                  15
Thr Val Ala Gln Ala Asp Ile Gln Met Thr Gln Ser Pro Ser Ser Leu
            20                  25                  30
Ser Ala Ser Val Gly Asp Arg Val Thr Ile Thr Cys Arg Thr Ser Glu
        35                  40                  45
Asp Ile Tyr Thr Asn Leu Ala Trp Tyr Gln Gln Lys Pro Gly Lys Val
    50                  55                  60
Pro Lys Leu Leu Ile Tyr Val Ala Lys Thr Leu Gln Asp Gly Val Pro
65                  70                  75                  80
Ser Arg Phe Ser Gly Ser Gly Ser Gly Thr His Tyr Thr Leu Thr Ile
                85                  90                  95
Ser Ser Leu Gln Pro Glu Asp Val Ala Thr Tyr Tyr Cys Leu Gln Gly
            100                 105                 110
Phe Lys Phe Pro Trp Thr Phe Gly Gly Gly Thr Lys Val Glu Ile Lys
        115                 120                 125
```

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 58
<211> LENGTH: 705
<212> TYPE: DNA
<213> ORGANISM: Artificial Sequence
<220> FEATURE:
<223> OTHER INFORMATION: 1638 gL2 light chain (E. coli expression)

<400> SEQUENCE: 58
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtcgcactag cgaggacatc tacaccaacc tggcgtggta tcagcagaaa     180
ccaggcaaag tgccgaaact gctgatctac gtcgcgaaaa ccctccagga cggtgtaccg     240
tctcgctttt ccggctctgg tagcggtact cactacaccc tgaccatctc ttccctccag     300
ccggaagatg ttgctaccta ctattgcctc cagggcttca aattcccgtg gactttcggt     360
ggcggcacga aagtggaaat caaacgtacg gtagcggccc catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct caccagtaac aaaaagtttt aatagagggg agtgt                    705

<210> SEQ ID NO 59
<211> LENGTH: 122
<212> TYPE: PRT
<213> ORGANISM: Artificial Sequence
<220> FEATURE:
<223> OTHER INFORMATION: 1638gH2 V-region

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Phe Ser Gly Phe Ser Leu Ser Thr Tyr
            20                  25                  30

Gly Val Gly Val Gly Trp Val Arg Gln Ala Pro Gly Lys Gly Leu Glu
        35                  40                  45

Trp Leu Ala Asn Ile Trp Trp Asp Asp Lys Arg Tyr Asn Pro Ser
    50                  55                  60

Leu Glu Asn Arg Phe Thr Ile Ser Lys Asp Thr Ala Lys Asn Ser Ala
65                  70                  75                  80

Tyr Leu Gln Met Asn Ser Leu Arg Ala Glu Asp Thr Ala Val Tyr Tyr
                85                  90                  95

Cys Val Arg Thr Pro Ala Tyr Tyr Gly Ser His Pro Pro Phe Asp Tyr
            100                 105                 110

Trp Gly Gln Gly Thr Met Val Thr Val Ser
        115                 120

<210> SEQ ID NO 60
<211> LENGTH: 366
<212> TYPE: DNA
<213> ORGANISM: Artificial Sequence
<220> FEATURE:
<223> OTHER INFORMATION: 1638gH2 V-region

<400> SEQUENCE: 60
gaggttcagc tggtcgagtc tggaggcggg cttgtccagc ctggagggag cctgcgtctc    60
tcttgtgcat tctccggctt ctctctgtct acctacggcg ttggtgttgg ttgggtacgt   120
caggctccag gtaaaggtct ggaatggctc gcaaacatct ggtgggacga cgataaacgc   180
tacaacccgt ccctggagaa ccgcttcacc attagcaaag ataccgcgaa aaactccgcg   240
tatctccaga tgaactccct gcgtgccgaa gacacggctg tgtactattg cgttcgcact   300
ccggcgtact atggctctca cccaccgttt gattactggg gtcagggtac catggttacc   360
gtctcg                                                             366

<210> SEQ ID NO 61
<211> LENGTH: 143
<212> TYPE: PRT
<213> ORGANISM: Artificial Sequence
<220> FEATURE:
<223> OTHER INFORMATION: 1638 gH2 V-region with signal sequence
      underlined and italicized (E. coli expression)

<400> SEQUENCE: 61

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Phe Ser Gly Phe
        35                  40                  45

Ser Leu Ser Thr Tyr Gly Val Gly Val Gly Trp Val Arg Gln Ala Pro
    50                  55                  60

Gly Lys Gly Leu Glu Trp Leu Ala Asn Ile Trp Trp Asp Asp Asp Lys
65                  70                  75                  80

Arg Tyr Asn Pro Ser Leu Glu Asn Arg Phe Thr Ile Ser Lys Asp Thr
                85                  90                  95

Ala Lys Asn Ser Ala Tyr Leu Gln Met Asn Ser Leu Arg Ala Glu Asp
            100                 105                 110

Thr Ala Val Tyr Tyr Cys Val Arg Thr Pro Ala Tyr Tyr Gly Ser His
        115                 120                 125

Pro Pro Phe Asp Tyr Trp Gly Gln Gly Thr Met Val Thr Val Ser
    130                 135                 140

<210> SEQ ID NO 62
<211> LENGTH: 429
<212> TYPE: DNA
<213> ORGANISM: Artificial Sequence
<220> FEATURE:
<223> OTHER INFORMATION: 1638 gH2 V-region with signal sequence underlined and italicized (E. coli expression)

<400> SEQUENCE: 62

```
atgaagaaga ctgctatagc aattgcagtg gcgctagctg gtttcgccac cgtggcgcaa    60
gctgaggttc agctggtcga gtctggaggc gggcttgtcc agcctggagg gagcctgcgt   120
ctctcttgtg cattctccgg cttctctctg tctacctacg gcgttggtgt tggttgggta   180
cgtcaggctc caggtaaagg tctggaatgg ctcgcaaaca tctggtggga cgacgataaa   240
cgctacaacc cgtccctgga gaaccgcttc accattagca agataccgc gaaaaactcc    300
gcgtatctcc agatgaactc cctgcgtgcc gaagacacgg ctgtgtacta ttgcgttcgc   360
actccggcgt actatggctc tcacccaccg tttgattact ggggtcaggg taccatggtt   420
accgtctcg                                                           429
```

<210> SEQ ID NO 63
<211> LENGTH: 234
<212> TYPE: PRT
<213> ORGANISM: Artificial Sequence
<220> FEATURE:
<223> OTHER INFORMATION: 1638 gH2 Fab' heavy chain (V + human gamma-1 CH1 + hinge)

<400> SEQUENCE: 63

```
Glu Val Gln Leu Val Glu Ser Gly Gly Gly Leu Val Gln Pro Gly Gly
 1               5                  10                  15

Ser Leu Arg Leu Ser Cys Ala Phe Ser Gly Phe Ser Leu Ser Thr Tyr
            20                  25                  30

Gly Val Gly Val Gly Trp Val Arg Gln Ala Pro Gly Lys Gly Leu Glu
        35                  40                  45

Trp Leu Ala Asn Ile Trp Trp Asp Asp Asp Lys Arg Tyr Asn Pro Ser
    50                  55                  60

Leu Glu Asn Arg Phe Thr Ile Ser Lys Asp Thr Ala Lys Asn Ser Ala
65                  70                  75                  80

Tyr Leu Gln Met Asn Ser Leu Arg Ala Glu Asp Thr Ala Val Tyr Tyr
                85                  90                  95

Cys Val Arg Thr Pro Ala Tyr Tyr Gly Ser His Pro Pro Phe Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Ala Ala
225                 230
```

<210> SEQ ID NO 64
<211> LENGTH: 702

```
<212> TYPE: DNA
<213> ORGANISM: Artificial Sequence
<220> FEATURE:
<223> OTHER INFORMATION: 1638 gH2 Fab' heavy chain (V + human gamma-1
      CH1 + hinge)

<400> SEQUENCE: 64
gaggttcagc tggtcgagtc tggaggcggg cttgtccagc ctggagggag cctgcgtctc      60
tcttgtgcat ctccggcttc tctctgtct acctacggcg ttggtgttgg ttgggtacgt     120
caggctccag gtaaaggtct ggaatggctc gcaaacatct ggtgggacga cgataaacgc     180
tacaacccgt ccctggagaa ccgcttcacc attagcaaag ataccgcgaa aaactccgcg     240
tatctccaga tgaactccct gcgtgccgaa gacacggctg tgtactattg cgttcgcact     300
ccggcgtact atggctctca cccaccgttt gattactggg gtcagggtac catggttacc     360
gtctcgagcg cttctacaaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt cgacaagaaa     660
gttgagccca atcttgtga caaaactcac acatgcgccg cg                        702

<210> SEQ ID NO 65
<211> LENGTH: 255
<212> TYPE: PRT
<213> ORGANISM: Artificial Sequence
<220> FEATURE:
<223> OTHER INFORMATION: 1638 gH2 Fab' heavy chain (E. coli expression)

<400> SEQUENCE: 65

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Phe Ser Gly Phe
        35                  40                  45

Ser Leu Ser Thr Tyr Gly Val Gly Val Gly Trp Val Arg Gln Ala Pro
    50                  55                  60

Gly Lys Gly Leu Glu Trp Leu Ala Asn Ile Trp Trp Asp Asp Asp Lys
65                  70                  75                  80

Arg Tyr Asn Pro Ser Leu Glu Asn Arg Phe Thr Ile Ser Lys Asp Thr
                85                  90                  95

Ala Lys Asn Ser Ala Tyr Leu Gln Met Asn Ser Leu Arg Ala Glu Asp
            100                 105                 110

Thr Ala Val Tyr Tyr Cys Val Arg Thr Pro Ala Tyr Tyr Gly Ser His
        115                 120                 125

Pro Pro Phe Asp Tyr Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
```

-continued

```
                195                 200                 205
Leu Ser Ser Val Val Thr Val Pro Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Ala Ala
                245                 250                 255
```

<210> SEQ ID NO 66
<211> LENGTH: 765
<212> TYPE: DNA
<213> ORGANISM: Artificial Sequence
<220> FEATURE:
<223> OTHER INFORMATION: 1638 gH2 Fab' heavy chain d (E. coli expression)

<400> SEQUENCE: 66

```
atgaagaaga ctgctatagc aattgcagtg gcgctagctg gtttcgccac cgtggcgcaa    60
gctgaggttc agctggtcga gtctggaggc gggcttgtcc agcctggagg gagcctgcgt   120
ctctcttgtg cattctccgg cttctctctg tctacctacg gcgttggtgt tggttgggta   180
cgtcaggctc caggtaaagg tctggaatgg ctcgcaaaca tctggtggga cgacgataaa   240
cgctacaacc cgtccctgga gaaccgcttc accattagca agatacgcg gaaaaactcc    300
gcgtatctcc agatgaactc cctgcgtgcc gaagacacgg ctgtgtacta ttgcgttcgc   360
actccggcgt actatggctc tcacccaccg tttgattact ggggtcaggg taccatggtt   420
accgtctcga gcgcttctac aaagggccca tcggtcttcc cctggcacc ctcctccaag    480
agcacctctg ggggcacagc ggccctgggc tgcctggtca aggactactt ccccgaaccg   540
gtgacggtgt cgtggaactc aggcgccctg accagcggcg tgcacacctt cccggctgtc   600
ctacagtcct caggactcta ctccctcagc agcgtggtga ccgtgccctc agcagcttg   660
ggcacccaga cctacatctg caacgtgaat cacaagccca gcaacaccaa ggtcgacaag   720
aaagttgagc ccaaatcttg tgacaaaact cacacatgcg ccgcg                    765
```

<210> SEQ ID NO 67
<211> LENGTH: 15
<212> TYPE: PRT
<213> ORGANISM: Artificial Sequence
<220> FEATURE:
<223> OTHER INFORMATION: N-termial sequence Heavy chain

<400> SEQUENCE: 67

```
Glu Val Gln Leu Val Glu Ser Gly Gly Gly Leu Val Gln Pro Gly
1               5                   10                  15
```

<210> SEQ ID NO 68
<211> LENGTH: 15
<212> TYPE: PRT
<213> ORGANISM: Artificial Sequence
<220> FEATURE:
<223> OTHER INFORMATION: N-terminal sequence Light chain

<400> SEQUENCE: 68

```
Asp Ile Gln Met Thr Gln Ser Pro Ser Ser Leu Ser Ala Ser Val
1               5                   10                  15
```

<210> SEQ ID NO 69
<211> LENGTH: 15
<212> TYPE: PRT
<213> ORGANISM: Artificial Sequence

```
<220> FEATURE:
<223> OTHER INFORMATION: human JH3

<400> SEQUENCE: 69

Asp Ala Phe Asp Val Trp Gly Gln Gly Thr Met Val Thr Val Ser
1               5                   10                  15

<210> SEQ ID NO 70
<211> LENGTH: 5
<212> TYPE: PRT
<213> ORGANISM: Artificial Sequence
<220> FEATURE:
<223> OTHER INFORMATION: part of CDR-H3

<400> SEQUENCE: 70

Asp Ala Phe Asp Val
1               5

<210> SEQ ID NO 71
<211> LENGTH: 12
<212> TYPE: PRT
<213> ORGANISM: Artificial Sequence
<220> FEATURE:
<223> OTHER INFORMATION: JK4 sequence

<400> SEQUENCE: 71

Leu Thr Phe Gly Gly Gly Thr Lys Val Glu Ile Lys
1               5                   10

<210> SEQ ID NO 72
<211> LENGTH: 99
<212> TYPE: PRT
<213> ORGANISM: Artificial Sequence
<220> FEATURE:
<223> OTHER INFORMATION: Human ?2-microglobulin

<400> SEQUENCE: 72

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
        50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 73
<211> LENGTH: 453
<212> TYPE: PRT
<213> ORGANISM: Artificial Sequence
<220> FEATURE:
<223> OTHER INFORMATION: 1638gH33 IgG1 heavy chain (V + human gamma-1
      constant)

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
```

```
                    20                  25                  30
            Gly Val Gly Val Gly Trp Val Arg Gln Ala Pro Gly Lys Gly Leu Glu
                            35                  40                  45

Trp Leu Ala Asn Ile Trp Trp Asp Asp Lys Arg Tyr Asn Pro Ser
             50                  55                  60

Leu Glu Asn Arg Phe Thr Ile Ser Arg Asp Asn Ala Lys Asn Ser Ala
             65                  70                  75                  80

Tyr Leu Gln Met Asn Ser Leu Arg Ala Glu Asp Thr Ala Val Tyr Tyr
                            85                  90                  95

Cys Ala Arg Thr Pro Ala Tyr Tyr Gly Ser His Pro Pro Phe Asp Tyr
                        100                 105                 110

Trp Gly Gln Gly Thr Met Val Thr Val Ser Ser Ala Ser Thr Lys Gly
                        115                 120                 125

Pro Ser Val Phe Pro Leu Ala Pro Ser Ser Lys Ser Thr Ser Gly Gly
                        130                 135                 140

Thr Ala Ala Leu Gly Cys Leu Val Lys Asp Tyr Phe Pro Glu Pro Val
            145                 150                 155                 160

Thr Val Ser Trp Asn Ser Gly Ala Leu Thr Ser Gly Val His Thr Phe
                            165                 170                 175

Pro Ala Val Leu Gln Ser Ser Gly Leu Tyr Ser Leu Ser Ser Val Val
                        180                 185                 190

Thr Val Pro Ser Ser Ser Leu Gly Thr Gln Thr Tyr Ile Cys Asn Val
                        195                 200                 205

Asn His Lys Pro Ser Asn Thr Lys Val Asp Lys Lys Val Glu Pro Lys
                        210                 215                 220

Ser Cys Asp Lys Thr His Thr Cys Pro Pro Cys Pro Ala Pro Glu Leu
            225                 230                 235                 240

Leu Gly Gly Pro Ser Val Phe Leu Phe Pro Pro Lys Pro Lys Asp Thr
                            245                 250                 255

Leu Met Ile Ser Arg Thr Pro Glu Val Thr Cys Val Val Val Asp Val
                        260                 265                 270

Ser His Glu Asp Pro Glu Val Lys Phe Asn Trp Tyr Val Asp Gly Val
                        275                 280                 285

Glu Val His Asn Ala Lys Thr Lys Pro Arg Glu Glu Gln Tyr Asn Ser
                        290                 295                 300

Thr Tyr Arg Val Val Ser Val Leu Thr Val Leu His Gln Asp Trp Leu
            305                 310                 315                 320

Asn Gly Lys Glu Tyr Lys Cys Lys Val Ser Asn Lys Ala Leu Pro Ala
                            325                 330                 335

Pro Ile Glu Lys Thr Ile Ser Lys Ala Lys Gly Gln Pro Arg Glu Pro
                        340                 345                 350

Gln Val Tyr Thr Leu Pro Pro Ser Arg Asp Glu Leu Thr Lys Asn Gln
                        355                 360                 365

Val Ser Leu Thr Cys Leu Val Lys Gly Phe Tyr Pro Ser Asp Ile Ala
                        370                 375                 380

Val Glu Trp Glu Ser Asn Gly Gln Pro Glu Asn Asn Tyr Lys Thr Thr
            385                 390                 395                 400

Pro Pro Val Leu Asp Ser Asp Gly Ser Phe Phe Leu Tyr Ser Lys Leu
                            405                 410                 415

Thr Val Asp Lys Ser Arg Trp Gln Gln Gly Asn Val Phe Ser Cys Ser
                        420                 425                 430

Val Met His Glu Ala Leu His Asn His Tyr Thr Gln Lys Ser Leu Ser
                        435                 440                 445
```

Leu Ser Pro Gly Lys
    450

<210> SEQ ID NO 74
<211> LENGTH: 1965
<212> TYPE: DNA
<213> ORGANISM: Artificial Sequence
<220> FEATURE:
<223> OTHER INFORMATION: 1638gH33 IgG1 heavy chain (V + human gamma-1
      constant, exons underlined)

<400> SEQUENCE: 74

| | |
|---|---:|
| gaggttcagc tggtcgagtc tggaggcggg cttgtccagc ctggagggag cctgcgtctc | 60 |
| tcttgtgcag cgtccggctt ctctctgtct acctacggcg ttggtgttgg ttgggtacgt | 120 |
| caggctccag gtaaaggtct ggaatggctc gcaaacatct ggtgggacga cgataaacgc | 180 |
| tacaacccgt ccctggagaa ccgcttcacc attagccgtg ataacgcgaa aaactccgcg | 240 |
| tatctccaga tgaactccct gcgtgccgaa gacacggctg tgtactattg cgcgcgcact | 300 |
| ccggcgtact atggctctca cccaccgttt gattactggg gtcagggtac aatggttacc | 360 |
| gtctcgagcg cttctacaaa gggcccatcg gtcttccccc tggcaccctc ctccaagagc | 420 |
| acctctgggg gcacagcggc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acccagacct acatctgcaa cgtgaatcac aagcccagca caccaaggt cgacaagaaa | 660 |
| gttggtgaga ggccagcaca gggagggagg tgtctgctg gaagccaggc tcagcgctcc | 720 |
| tgcctggacg catcccggct atgcagcccc agtccagggc agcaaggcag gccccgtctg | 780 |
| cctcttcacc cggaggcctc tgcccgcccc actcatgctc agggagaggg tcttctggct | 840 |
| ttttccccag gctctgggca ggcacaggct aggtgcccct aacccaggcc ctgcacacaa | 900 |
| aggggcaggt gctgggctca gacctgccaa gagccatatc cggaggaccc tgccccctga | 960 |
| cctaagccca ccccaaaggc caaactctcc actccctcag ctcggacacc ttctctcctc | 1020 |
| ccagatctga gtaactccca atcttctctc tgcagagccc aaatcttgtg acaaaactca | 1080 |
| cacatgccca ccgtgcccag gtaagccagc ccaggcctcg ccctccagct caaggcggga | 1140 |
| caggtgccct agagtagcct gcatccaggg acaggcccca gccgggtgct gacacgtcca | 1200 |
| cctccatctc ttcctcagca cctgaactcc tgggggggacc gtcagtcttc ctcttccccc | 1260 |
| caaaacccaa ggacaccctc atgatctccc ggacccctga ggtcacatgc gtggtggtgg | 1320 |
| acgtgagcca cgaagaccct gaggtcaagt tcaactggta cgtggacggc gtggaggtgc | 1380 |
| ataatgccaa gacaaagccg cggaggagc agtacaacag cacgtaccgt gtggtcagcg | 1440 |
| tcctcaccgt cctgcaccag gactggctga atggcaagga gtacaagtgc aaggtctcca | 1500 |
| acaaagccct cccagccccc atcgagaaaa ccatctccaa agccaaaggt gggaccgtg | 1560 |
| gggtgcgagg gccacatgga cagaggccgg ctcggcccac cctctgccct gagagtgacc | 1620 |
| gctgtaccaa cctctgtccc tacagggcag ccccagagaac cacaggtgta cccctgccc | 1680 |
| ccatcccggg atgagctgac caagaaccag gtcagcctga cctgcctggt caaaggcttc | 1740 |
| tatcccagcg acatcgccgt ggagtgggag agcaatgggc agccggagaa caactacaag | 1800 |

-continued

```
accacgcctc ccgtgctgga ctccgacggc tccttcttcc tctacagcaa gctcaccgtg    1860
gacaagagca ggtggcagca ggggaacgtc ttctcatgct ccgtgatgca tgaggctctg    1920
cacaaccact acacgcagaa gagcctctcc ctgtctccgg gtaaa                    1965
```

UNITED STATES PATENT AND TRADEMARK OFFICE
CERTIFICATE OF CORRECTION

| | | |
|---|---|---|
| PATENT NO. | : 11,220,547 B2 | |
| APPLICATION NO. | : 16/299407 | |
| DATED | : January 11, 2022 | |
| INVENTOR(S) | : Atherfold et al. | |

It is certified that error appears in the above-identified patent and that said Letters Patent is hereby corrected as shown below:

On the Title Page

On page four, second Column, item (56) Line 69 should read -- Co-Pending U.S. Appl. No. 16/622,658, filed Dec. 13, 2019 --.

Signed and Sealed this
Nineteenth Day of April, 2022

*Katherine Kelly Vidal*

Katherine Kelly Vidal
*Director of the United States Patent and Trademark Office*